United States Patent
Smirnov et al.

(10) Patent No.: US 10,077,447 B2
(45) Date of Patent: Sep. 18, 2018

(54) CORYNEFORM BACTERIUM AND METHOD FOR PRODUCING HETEROLOGOUS FUSION PROTEINS

(71) Applicant: AJINOMOTO CO., INC., Tokyo (JP)

(72) Inventors: Sergey Vasilievich Smirnov, Moscow (RU); Veronika Aleksandrovna Kotliarova, Moscow (RU); Hidemi Fujii, Kanagawa (JP); Masakazu Sugiyama, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 188 days.

(21) Appl. No.: 14/924,201

(22) Filed: Oct. 27, 2015

(65) Prior Publication Data

US 2016/0060640 A1    Mar. 3, 2016

Related U.S. Application Data

(63) Continuation of application No. PCT/JP2014/062292, filed on Apr. 28, 2014.

(30) Foreign Application Priority Data

Apr. 29, 2013 (RU) .................. 2013119826

(51) Int. Cl.
| | |
|---|---|
| *C12N 15/77* | (2006.01) |
| *C07K 14/605* | (2006.01) |
| *C07K 1/107* | (2006.01) |
| *C07K 16/32* | (2006.01) |
| *C07K 14/34* | (2006.01) |
| *C12P 21/02* | (2006.01) |
| *C12P 21/06* | (2006.01) |
| *C12N 15/62* | (2006.01) |
| *C07K 1/00* | (2006.01) |

(52) U.S. Cl.
CPC ............. *C12N 15/77* (2013.01); *C07K 1/003* (2013.01); *C07K 1/107* (2013.01); *C07K 14/34* (2013.01); *C07K 14/605* (2013.01); *C07K 16/32* (2013.01); *C12N 15/62* (2013.01); *C12P 21/02* (2013.01); *C12P 21/06* (2013.01); *C07K 2317/21* (2013.01); *C07K 2317/24* (2013.01); *C07K 2317/52* (2013.01); *C07K 2317/54* (2013.01); *C07K 2317/55* (2013.01); *C07K 2317/622* (2013.01); *C07K 2319/00* (2013.01); *C07K 2319/02* (2013.01); *C07K 2319/20* (2013.01); *C07K 2319/21* (2013.01); *C07K 2319/30* (2013.01); *C07K 2319/92* (2013.01)

(58) Field of Classification Search
None
See application file for complete search history.

(56) References Cited

U.S. PATENT DOCUMENTS

| | | | |
|---|---|---|---|
| 6,399,368 | B1 | 6/2002 | Ward |
| 6,849,428 | B1 | 2/2005 | Evans et al. |
| 7,491,528 | B2 | 2/2009 | Lee et al. |
| 8,273,562 | B2 | 9/2012 | Kodera et al. |
| 8,367,381 | B2 | 2/2013 | Kodera et al. |
| 8,367,382 | B2 | 2/2013 | Kodera et al. |
| 8,372,607 | B2 | 2/2013 | Kuroda et al. |
| 8,524,476 | B2 | 9/2013 | Smirnov et al. |
| 9,051,591 | B2 | 6/2015 | Kuvaeva et al. |
| 2015/0203881 | A1 | 7/2015 | Ptitsyn et al. |

FOREIGN PATENT DOCUMENTS

| | | |
|---|---|---|
| EP | 1219713 A1 | 7/2002 |
| EP | 1748077 A1 | 1/2007 |
| EP | 2108047 B1 | 10/2012 |
| WO | WO01/23591 A1 | 4/2001 |
| WO | WO2013/065869 A1 | 5/2013 |

OTHER PUBLICATIONS

Perler, F.B., "InBase: The Intein Database", Nucleic Acid Research, 2002, vol. 30, No. 1, pp. 383-384.*
International Preliminary Report on Patentability for PCT Patent App. No. PCT/JP2014/062292 (dated Nov. 3, 2015).
Cottingham, I. R., et al., "A method for the amidation of recombinant peptides expressed as intein fusion proteins in *Escherichia coli*," Nat. Biotechnol. 2001;19:974-977.
Date, M., et al., "High level expression of Streptomyces mobaraensis transglutaminase in Corynebacterium glutamicum using a chimeric pro-region from Streptomyces cinnamoneus transglutaminase," J. Biotechnol. 2004;110:219-226.
Elleuche, S., et al., "Inteins, valuable genetic elements in molecular biology and biotechnology," Appl. Microbiol. Biotechnol. 2010;87:479-489.
Evans, T. C., et al., "The in Vitro Ligation of Bacterially Expressed Proteins Using an Intein from Methanobacterium thermoautotrophicum," J. Biol. Chem. 1999;274(7):3923-3926.
International Search Report for PCT Patent App. No. PCT/JP2014/062292 (dated Sep. 22, 2014).
Möhlmann, S., et al., "Site-specific modification of ED-B-targeting antibody using intein-fusion technology," BMC Biotechnol. 2011;11:76.
Muir, T. W., et al., "Expressed protein ligation: A general method for protein engineering," Proc. Natl. Acad. Sci. USA 1998;95:6705-6710.

(Continued)

*Primary Examiner* — Suzanne M Noakes
(74) *Attorney, Agent, or Firm* — Cermak Nakajima & McGowan LLP; Shelly Guest Cermak

(57) ABSTRACT

The present invention provides a coryneform bacterium having an ability to produce a heterologous fusion protein by secretory production, which has been modified to express a genetic construct for secretory production of the heterologous fusion protein encoding at least a heterologous fusion protein comprising an extein and an intein having an activity of acyl rearrangement. The method for producing proteins modified at the C-terminus is also provided.

37 Claims, 33 Drawing Sheets

Specification includes a Sequence Listing.

(56) References Cited

OTHER PUBLICATIONS

Myscofski, D. M., et al., "Cleavage and Purification of Intein Fusion Proteins Using the *Streptococcus gordonii* Spex System," Prep. Biochem. & Biotechnol. 2001;31(3):275-290.

Sudheer, P. D. V. N., et al., "Cyclization tag for the detection and facile purification of backbone-cyclized proteins," Analytical Biochem. 2013;436:137-141.

Vila-Perelló, M., et al., "Biological Applications of Protein Splicing," Cell 2010;143:191-200.

Volkmann, G., et al., "Recent progress in intein research: from mechanism to directed evolution and applications," Cell. Mol. Life Sci. 2013;70:1185-1206.

\* cited by examiner

Lanes:
M - Mw-marker of indicated molecular weights;
CB - culture broth;
UB - pooled fractions 1, 2, and 3 unbounded to a column;
7 - 23 – fractions eluted from the column.

The EXI1 fusion protein is marked by rectangles.

Lanes:
M - Mw-marker of indicated molecular weights;
1 - EXI1 eluted in fraction 18 with 50 mM Tris-HCl pH 8.0, incubated at 0 °C for 16 hours;
2 - EXI1 eluted in fraction 18 with 50 mM Tris-HCl pH 8.0 and 100 mM DTT, incubated at 0 °C for 16 hours;
3 - EXI1 eluted in fraction 22 with 50 mM Tris-HCl pH 8.0, incubated at 0 °C for 16 hours;
4 - EXI1 eluted in fraction 22 with 50 mM Tris-HCl pH 8.0 and 100 mM DTT, incubated at 0 °C for 16 hours.

Lanes:
M - Mw-marker of indicated molecular weights;
1 - culture broth of the YDK010[pEXC1] strain;
2 - culture broth of the YDK010[pEXC1-exe-MAG-HT#2] strain;
3 - the same as lane 2, but with addition of 100 mM DTT and incubation of the culture broth at 4 °C for about 16 hours.

The EXI1HT fusion protein is marked by rectangle.

Lanes:
M - Mw-marker of indicated molecular weights;
1 - culture broth;
2 - unbound fraction;
3 - 8 - eluted fractions.

The EXI1HT fusion protein is marked by rectangle.

Reducing (A) and non-reducing (B) SDS-PAGE of fractions 8-13 eluted from HisTrap column (IMAC).

Lanes:
M - Mw-marker of indicated molecular weights;
CB - culture broth of YDK010 strain harboring pEXC1-exe-MAG-HT#2 plasmid;
A - protein preparation applied onto the HisTrap column;
UN - unbound fractions.

FIG. 18

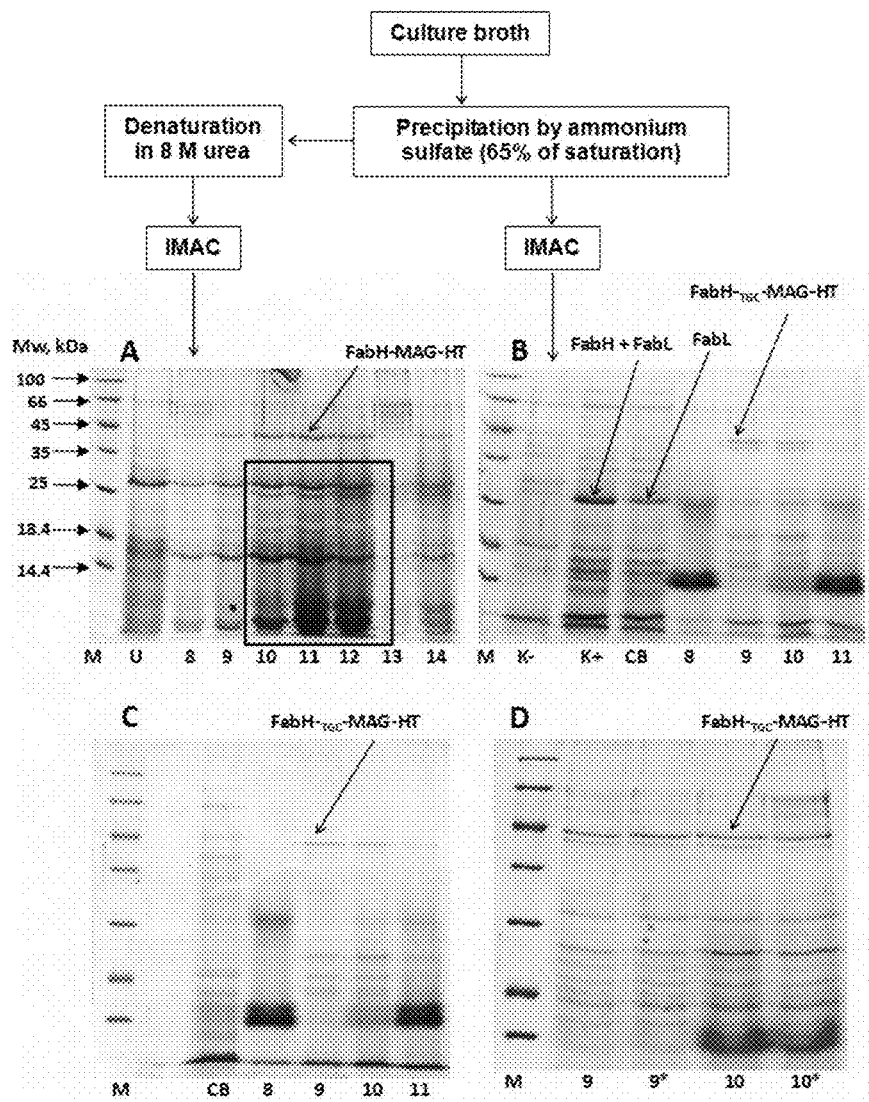

Panel A: lane U - crude protein preparation. Proteolytic fragments of FabH-TGC-MAG-HT are shown in square.

Panels B and C: lanes K-, K+, and CB - protein preparations from culture broths of YDK010ΔPBP1a strain harboring plasmid pEXC1, pPKSherFabHL, or pPKSherFabH-TGC-MAG-HT-FabL respectively.

Panel D: lanes 9, 10 - control reactions without DTT, lanes 9*, 10* - test reactions with addition of 100 mM DTT.

M - Mw-marker of indicated molecular weights.

Lanes:
M - Mw-marker of indicated molecular weights;
1 - pEXC1 (negative control);
2 - pPKSherFabHL (positive control);
3 - pPKSherFabH-FabL-cGc-MAG-HT.

Lanes:
M - Mw-marker of indicated molecular weights;
CB - culture broth of YDK110ΔPBP1a harboring the pPKSherFabH-FabL-cGc-MAG-HT plasmid.

Lanes:
M - Mw-marker of indicated molecular weights;
CB - culture broth without DTT;
8-12 - control reactions without DTT;
m - mixture of equal aliquots of fractions 8-12 without DTT;
CB* - culture broth with 100 mM DTT;
8*-12* - test reactions with 100 mM DTT;
m* - mixture of equal aliquots of fractions 8*-12* with 100 mM DTT.

CB - culture broth of YDK110ΔPBP1a strain harboring the pPK-SherFabH-FabL-$_{CGC}$-MAG-HT plasmid.

FIG. 22
A
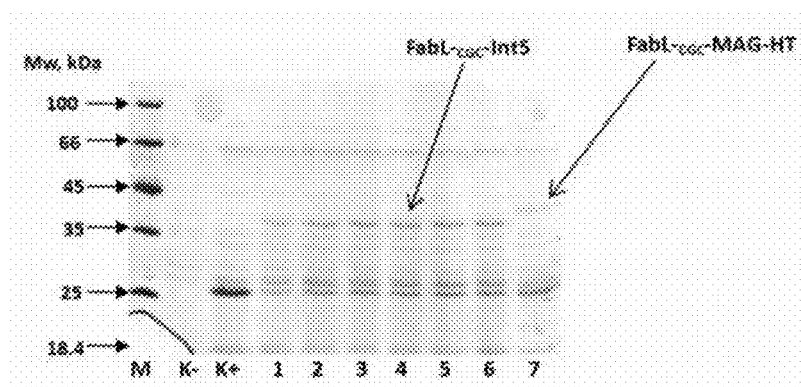
B
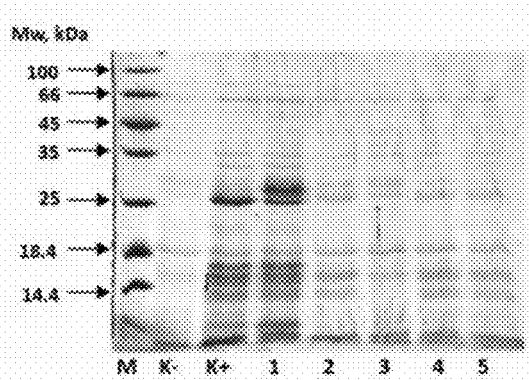
C
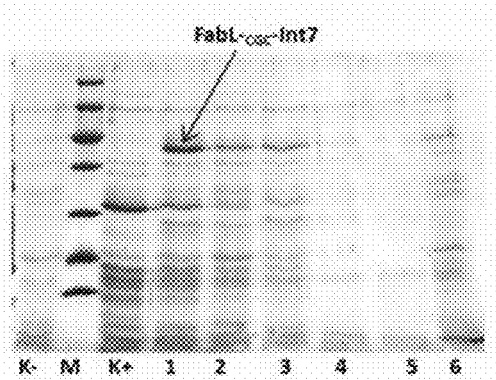
Lanes:
M - Mw-marker of indicated molecular weights;
K- - pEXC1(negative control);
K+ - pPKSherFabHL (positive control);
A7 - pPKSherFabH-FabL-$_{CGC}$-MAG-HT (positive control);
A1-A6 - pPKSherFabH-FabL-$_{CGC}$-Int5#(1-6);
B1-B5 - pPKSherFabH-FabL-$_{CGC}$-Int4#(25-28,30);
C1-C5 - pPKSherFabH-FabL-$_{CGC}$-Int7#(37-42).

Lanes:
M - Mw-marker of indicated molecular weights;
K- - pEXC1(negative control);
K+ - pPKSherFabHL (positive control);
1 - pPKSherFabH-$_{TGC}$-MAG-FabL (positive control);
A2-A6 - pPKSherFabH-$_{TGC}$-Int4-HT-FabL#(41-43, 45, 46);
B2-B6 - pPKSherFabH-$_{TGC}$-Int5-HT-FabL#(51-43, 55, 56);
C2-C7 - pPKSherFabH-$_{TGC}$-Int7-HT-FabL#(71-76).

Lanes:
M - Mw-marker of indicated molecular weights;
K- - pEXC1(negative control);
K+ - pPKSherFabHL (positive control);
1 - pPKSherFabH-$_{TGC}$-Int4-HT-FabL;
2 - pPKSherFabH-$_{TGC}$-Int5-HT-FabL;
3 - pPKSherFabH-$_{TGC}$-Int7-HT-FabL.

Lanes:
M - Mw-marker of indicated molecular weights;
1 - FabH-$_{TGC}$-Int4-HT, without DTT;
2 - FabH-$_{TGC}$-Int4-HT, with 100 mM DTT;
3 - FabH-$_{TGC}$-Int5-HT, without DTT;
4 - FabH-$_{TGC}$-Int5-HT, with 100 mM DTT;
5 - FabH-$_{TGC}$-Int7-HT, without DTT;
6 - FabH-$_{TGC}$-Int7-HT, with 100 mM DTT.

The protein bands corresponding to cleaved His6-tagged inteins are shown by arrows.

Lanes:
M - Mw-marker of indicated molecular weights;
A1-A6 - FabH-$_{TGC}$-Int18-HT#1-3;
B1-B6 - FabH-$_{TGC}$-Int19-HT#3-5;
A1, A3, A5, B1, B3, B5 - without DTT;
A2, A4, A6, B2, B4, B6 - with 100 mM DTT.

The protein bands corresponding to cleaved His6-tagged inteins are shown by lower sloping arrow. Disappearance of bands corresponding to fused proteins FabH-$_{TGC}$-IntX-HT, X = 18 or 19 is shown by upper sloping arrows.

Lanes:
M - Mw-marker of indicated molecular weights;
1 – control reaction, without 50 mM DTT;
2 – test reaction, with 50 mM DTT;
3 – proteins bound to Chitin Resin but not eluted upon addition of DTT Lanes:
M - Mw-marker of indicated molecular weights;
1 - pEXC1 (negative control);
2 - pEXC1-BLA-exe-MAG-CBD (positive control).

Lanes:
M – Mw-marker of indicated molecular weights;
1 – control reaction, without 50 mM DTT;
2 – test reaction, with 50 mM DTT.

FIG. 38

Boc-Lys(2-ClZ)-NH$_2$

↓ 1)Pd/H$_2$
       2)Biotin/WSCD/HOBt

Boc-Lys((Biot)-NH$_2$

↓ 1)TFA
       2)Boc-Cys(Trt)-OH/WSCD/HOBt

Boc-Cys(Trt)-Lys(Biot)-NH$_2$

↓ TFA/Triisopropylsilane/H$_2$O

Cys-Lys(Biot)-NH$_2$

WSCD: Water-Soluble Carbodiimide,
    1-Ethyl-3-(3-Dimethylaminopropyl)-Carbodiimide HOBt: 1-Hydroxybenzotriazole

CORYNEFORM BACTERIUM AND METHOD FOR PRODUCING HETEROLOGOUS FUSION PROTEINS

This application is a Continuation of, and claims priority under 35 U.S.C. § 120 to, International Application No. PCT/JP2014/062292, filed Apr. 28, 2014, and claims priority therethrough under 35 U.S.C. § 119 to Russian Patent Application No. 2013119826, filed Apr. 29, 2013, the entireties of which are incorporated by reference herein. Also, the Sequence Listing filed electronically herewith is hereby incorporated by reference (File name: 2015-10-27T_US-538_Seq_List; File size: 74 KB; Date recorded: Oct. 27, 2015).

BACKGROUND OF THE INVENTION

Field of the Invention

The present invention relates to the microbiological industry, and specifically to a coryneform bacterium which efficiently produces a heterologous fusion protein by secretory production and a method for secretory production of a heterologous fusion protein using the modified coryneform bacterium.

Brief Description of the Related Art

Inteins are proteins which are capable of catalyzing their own excision from a precursor protein with the concomitant joining of the flanking protein sequences, known as exteins (Vila-Perelló M. and Muir T. W., Biological applications of protein splicing, *Cell*, 2010, 143(2):191-200). An intermediate forms during the intein-mediated protein splicing, which can be further modified chemically to obtain a recombinant protein or a peptide. In particular, the intermediate can be modified to produce proteins which are ligated, circularized, or conjugated with radioisotopes or chemical drugs. Antibodies can also be site-specifically modified using intein-mediated protein splicing. Various kinds of post-translational modifications of antibodies such as conjugation with polyethylene glycol (PEG), toxins, or radioisotopes have been investigated for the purpose of enhancing the efficacy of the antibody drugs, or adding novel functions to the antibody drugs. For example, certolizumab pegol (Cimzia, UCB), a tumor-necrosis factor blocker which is a Fab-PEG conjugate, was approved by the FDA in 2008 for the treatment of adult patients with moderate-to-severe Crohn's disease. Conjugation with PEG may enhance plasma half-life. Another example of modification of antibodies is a conjugation of an antibody or an antibody-related molecule with a toxin moiety (so called antibody-drug conjugates, ADC).

A method for protein engineering known as "expressed protein ligation" has been developed which is suitable for modification of the C-terminus of a target protein of any size by a nucleophilic group-containing compounds (Muir T. W. et al., Expressed protein ligation: A general method for protein engineering, *Proc. Natl. Acad. Sci. USA*, 1998, 95:6705-6710). The method of "expressed protein ligation" was successfully applied to modification of the protein tyrosine kinase C-terminal Src kinase (Csk) at the C-terminus through the expression of a fusion protein and replacement of the intein with a synthetic phosphotyrosine peptide under thiolysis conditions. The method for ligation of the expressed proteins has been disclosed, which utilizes inteins such as the R1R1 intein from *Methanobacterium thermotrophicum* (U.S. Pat. No. 6,849,428 B1; Evans T. C. Jr. et al., The in vitro ligation of bacterially expressed proteins using an intein from *Methanobacterium thermoautotrophicum*, *J. Biol. Chem.*, 1999, 274(7):3923-3926). The method for amidation of recombinant peptides expressed as fusion proteins containing inteins has also been disclosed (Cottingham I. R. et al., A method for the amidation of recombinant peptides expressed as intein fusion proteins in *Escherichia coli*, *Nat. Biotechnol.*, 2001, 19:974-977). Most of the commercial pharmaceutical peptides are amidated at their C-terminus to prolong the half-life in vivo. The peptide amidation technology utilizing a combination of expression of the recombinant fusion proteins and intein-mediated amidation reaction is also an important technology for obtaining C-terminal amidated peptides. The intein-mediated modifications can also be used for conjugation of proteins with labeled compounds such as radioisotopes or fluorescent compounds, biotin, etc. (Mohlmann S. et al., Site-specific modification of ED-B-targeting antibody using intein-fusion technology, *BMC Biotechnol.*, 2011, 11:76) and circularization of proteins (Sudheer P. D. et at., Cyclization tag for the detection and facile purification of backbone-cyclized proteins, *Anal. Biochem.*, 2013, 436:137-141).

To facilitate intein-mediated protein modification, the target protein may be expressed as a fusion protein with an appropriate intein. In general, the target protein-intein fusion proteins are expressed in *Escherichia coli*. The IMPACT system from New England Biolabs (catalog No. N6951S) utilizing the pTWIN vector is the most published commercial intein system in *E. coli*. Formation of an insoluble inclusion body often occurs when the target protein-intein fusion protein is expressed in *E. coli*. Therefore, a refolding process may be necessary to obtain the active form of the target protein-intein fusion protein recovered from the insoluble fraction. Expression of a target protein-intein fusion protein into a culture medium is more favorable due to the convenience for recovering the folded target protein-intein fusion protein from the culture medium. Expression of a target protein-intein fusion protein into culture media has been demonstrated using a mammalian cell expression system (Mohlmann S. et al., Site-specific modification of ED-B-targeting antibody using intein-fusion technology, *BMC Biotechnol.*, 2011, 11:76).

Methods for obtaining fused target proteins from the culture supernatant using bacterial expression systems are known. For, example, a method for expression and secretion of the $V_\alpha$, $V_\beta$ and single chain $V_\alpha$-$V_\beta$ fragments of murine T-cell receptors fused with a signal peptide was reported for Gram-negative bacteria cells (U.S. Pat. No. 6,399,368 B1). A chimeric pro-region from *Streptomyces cinnamoneus* transglutaminase was used to attain high level expression of *Streptomyces mobaraensis* transglutaminase as a fusion protein in *Corynebacterium glutamicum* (Date M. et al., *J. Biotechnol.*, 2004, 110(3):219-226). A method for the extracellular production of target proteins fused with an outer membrane protein OmpF and an oligopeptide for cleavage by a proteolytic enzyme utilizing *E. coli* as an expression host is known (U.S. Pat. No. 7,491,528 B2). Signal sequences from genes of *Pseudomonas fluorescens* and *Bacillus coagulans* for efficient secretion of correctly folded proteins from Gram-negative bacteria as expression hosts have been described (EP 2108047 B1). Also, a process for the secretory production of an exogenous protein by using a coryneform bacterium has been disclosed (WO 2001023591 A1). A target exogenous protein was expressed and excreted by a coryneform bacterium to a culture medium as a fusion protein with a signal peptide. The target protein was obtained by treating the extracellularly released fusion protein with a protease to cleave and eliminate the pro-part (WO 2001023591 A1).

Data demonstrating secretory production of the target protein-intein fusion proteins (also referred to as the heterologous fusion proteins as described in the present invention) using a coryneform bacterium has not been previously reported.

SUMMARY OF THE INVENTION

An object of the present invention is to develop a novel technique for secretory production of a heterologous fusion protein by a coryneform bacterium, and thereby provide a coryneform bacterium that produces a heterologous fusion protein by secretory production and a method for secretory production of a heterologous fusion protein using the bacterium.

It has been found that, in a method for producing a heterologous fusion protein utilizing a coryneform bacterium as an expression host, an ability of the coryneform bacterium to produce a heterologous fusion protein by secretory production could be imparted to the bacterium by expressing a nucleic acid sequence encoding the heterologous fusion protein, and a method for producing a modified protein using the heterologous fusion protein.

An aspect of the present invention is to provide a coryneform bacterium having an ability to produce a heterologous fusion protein by secretory production, wherein said bacterium has been modified to express a genetic construct that allows for secretory production of the heterologous fusion protein, wherein said genetic construct comprises a DNA encoding at least a heterologous fusion protein, wherein the heterologous fusion protein comprises an extein and an intein having an activity of acyl rearrangement.

It is a further aspect of the present invention to provide the coryneform bacterium as described above, wherein the extein further comprises a target protein.

It is a further aspect of the present invention to provide the coryneform bacterium as described above, wherein the extein further comprises a linker, which is linked to the C-terminus of the target protein and is in between the target protein and the intein.

It is a further aspect of the present invention to provide the coryneform bacterium as described above, wherein the linker comprises a sequence of one or more amino acid residues.

It is a further aspect of the present invention to provide the coryneform bacterium as described above, wherein the linker has a —NH—CH(R1)—CO—NH—CH(R2)-CO— motif at the C-terminus, where R1 and R2 are a side-chain group of a proteinogenic L-amino acid of the same or different kinds.

It is a further aspect of the present invention to provide the coryneform bacterium as described above, wherein the R1 is the side-chain group of any proteinogenic L-amino acid or hydrogen, and R2 is the side-chain group of L-cysteine.

It is a further aspect of the present invention to provide the coryneform bacterium as described above, wherein the target protein is a heterologous protein for the coryneform bacterium.

It is a further aspect of the present invention to provide the coryneform bacterium as described above, wherein the target protein is selected from the group consisting of a bioactive protein, a receptor protein, an antigenic protein, and an enzyme.

It is a further aspect of the present invention to provide the coryneform bacterium as described above, wherein the bioactive protein is selected from the group consisting of a growth factor, a hormone, a cytokine, and an antibody-related molecule.

It is a further aspect of the present invention to provide the coryneform bacterium as described above, wherein the bioactive protein is an exenatide selected from the group consisting of:

(A) a protein having the amino acid sequence of SEQ ID NO: 34, and (B) a protein having the amino acid sequence of SEQ ID NO: 34, but which includes substitution, deletion, insertion, or addition of one or several amino acid residues and has activity according to the amino acid sequence of SEQ ID NO: 34.

It is a further aspect of the present invention to provide the coryneform bacterium as described above, wherein the antibody-related molecule is a protein selected from the group consisting of Fab, F(ab')$_2$, an Fc-fusion protein, scFv, and combinations thereof.

It is a further aspect of the present invention to provide the coryneform bacterium as described above, wherein the Fab is a trastuzumab Fab having a heavy chain selected from the group consisting of:

(C) a protein having the amino acid sequence of SEQ ID NO: 35, and (D) a protein having the amino acid sequence of SEQ ID NO: 35, but which includes substitution, deletion, insertion, or addition of one or several amino acid residues and has activity according to the amino acid sequence of SEQ ID NO: 35;

and trastuzumab Fasb has a light chain selected from the group consisting of:

(E) a protein having the amino acid sequence of SEQ ID NO: 36, and (F) a protein having the amino acid sequence of SEQ ID NO: 36, but which includes substitution, deletion, insertion, or addition of one or several amino acid residues and has activity according to the amino acid sequence of SEQ ID NO: 36.

It is a further aspect of the present invention to provide the coryneform bacterium as described above, wherein the intein is selected from the group consisting of):

(G) an amino acid sequence of SEQ ID NO: 37, and (H) a amino acid sequence of SEQ ID NO: 37, but which includes substitution, deletion, insertion, or addition of one or several amino acid residues and has activity of acyl rearrangement.

It is a further aspect of the present invention to provide the coryneform bacterium as described above, wherein the intein is selected from the group consisting of:

an amino acid sequence of SEQ ID NO: 38, 40, 41 or 42, and a amino acid sequence of SEQ ID NO: 38, 40, 41 or 42, but which includes substitution, deletion, insertion, or addition of one or several amino acid residues and has activity of acyl rearrangement.

It is a further aspect of the present invention to provide the coryneform bacterium as described above, wherein the intein is selected from the group consisting of:

an amino acid sequence of SEQ ID NO: 37, and a amino acid sequence of SEQ ID NO: 37, but which includes substitution, deletion, insertion, or addition of one or several amino acid residues and has activity of acyl rearrangement.

It is a further aspect of the present invention to provide the coryneform bacterium as described above, wherein the bacterium has been modified further so that activity of a penicillin-binding protein is reduced.

It is a further aspect of the present invention to provide the coryneform bacterium as described above, wherein the activity of the penicillin-binding protein is reduced by attenuating expression of a gene encoding the penicillin-binding protein or disrupting the gene.

It is a further aspect of the present invention to provide the coryneform bacterium as described above, wherein the penicillin-binding protein is PBP1a or PBP1b.

It is a further aspect of the present invention to provide the coryneform bacterium as described above, wherein the penicillin-binding protein is selected from the group consisting of:

an amino acid sequence of SEQ ID NO: 44 or 46, and
a protein having the amino acid sequence of SEQ ID NO: 44 or 46, but which includes substitution, deletion, insertion, or addition of one or several amino acid residues and has activity that if the activity thereof is reduced in the coryneform bacterium, amount of the heterologous fusion protein produced by secretory production is increased compared with that observed for a non-modified strain.

It is a further aspect of the present invention to provide the coryneform bacterium as described above, wherein the bacterium has been modified further so that activity of a cell surface layer protein is reduced.

It is a further aspect of the present invention to provide the coryneform bacterium as described above, wherein the activity of the cell surface layer protein is reduced by attenuating expression of a gene encoding the cell surface layer protein or disrupting the gene.

It is a further aspect of the present invention to provide the coryneform bacterium as described above, wherein the cell surface layer protein is PS1, CspB, or CspA.

It is a further aspect of the present invention to provide the coryneform bacterium as described above, wherein the cell surface layer protein is selected from the group consisting of:

an amino acid sequence of SEQ ID NO: 56, 57 or 58, and
a protein having the amino acid sequence of SEQ ID NO: 56, 57 or 58, but which includes substitution, deletion, insertion, or addition of one or several amino acid residues and has activity that if the activity thereof is reduced in the coryneform bacterium, amount of the heterologous fusion protein produced by secretory production is increased compared with that observed for a non-modified strain.

It is a further aspect of the present invention to provide the coryneform bacterium as described above, wherein the genetic construct for secretory production of the heterologous fusion protein further comprises a promoter that functions in the coryneform bacterium.

It is a further aspect of the present invention to provide the coryneform bacterium as described above, wherein the genetic construct for secretory production of the heterologous fusion protein further comprises a signal peptide that functions in the coryneform bacterium.

It is a further aspect of the present invention to provide the coryneform bacterium as described above, wherein the bacterium belongs to the genus *Corynebacterium* or *Brevibacterium*.

It is a further aspect of the present invention to provide the coryneform bacterium as described above, wherein the bacterium is *Corynebacterium glutamicum*.

It is an aspect of the present invention to provide a method for producing a heterologous fusion protein by secretory production comprising:

cultivating the bacterium of as described above in a culture medium; and
collecting the heterologous fusion protein produced by secretory production.

It is an aspect of the present invention to provide a method for producing a protein ligated to a substance, comprising:

producing a heterologous fusion protein by the method as described above, and
reacting the heterologous fusion protein with a reactant, wherein the reactant comprises the substance, or the method further comprises modifying the reactant with the substance.

It is a further aspect of the present invention to provide the method as described above, wherein the heterologous fusion protein comprises a thioester or an ester bond in between the extein and the intein, and the thioester or the ester bond is cleaved by reacting the heterologous fusion protein with a reactant comprising a nucleophilic group selected from amino group, thiol group and hydroxyl group.

It is a further aspect of the present invention to provide the method as described above, wherein the heterologous fusion protein comprises a thioester bond in between the extein and the intein, and the thioester bond is cleaved by reacting the heterologous fusion protein with the reactant comprising thiol group.

It is a further aspect of the present invention to provide the method as described above, wherein the heterologous fusion protein is reacted with the reactant in the presence of 2-mercaptoethansulfonic acid.

It is a further aspect of the present invention to provide the method as described above, wherein the reactant comprises a toxin.

It is a further aspect of the present invention to provide the method as described above, wherein the reactant comprises a drug.

It is a further aspect of the present invention to provide the method as described above, wherein the reactant comprises a polyethylene glycol, a radioisotope-labeled compound, or a second polypeptide.

It is an aspect of the present invention to provide a method for producing a protein, which is amidated at the C-terminus, comprising:

producing a heterologous fusion protein by the method as described above, and
reacting the heterologous fusion protein with ammonia or a salt thereof.

It is a further aspect of the present invention to provide the method for producing a protein, which is amidated at the C-terminus, wherein the heterologous fusion protein is reacted with ammonia or a salt thereof, in the presence of a compound containing a nucleophilic thiol group.

The present invention is described in detail hereafter.

BRIEF DESCRIPTION OF THE DRAWINGS

FIG. 18 shows the SDS-PAGE analysis of purification and activity of FabH-$_{TGC}$-MAG-HT (photograph).

FIG. 22 shows the SDS-PAGE analysis of crude cell lysates of the YDK010ΔPBP1a strain harboring pPKSher-FabH-FabL-$_{CGC}$-IntX, X=4, 5 or 7 (photograph).

FIG. 38 shows the scheme for synthesis of Cys-Lys (Biotin).

DESCRIPTION OF SEQUENCES

Figure 1:
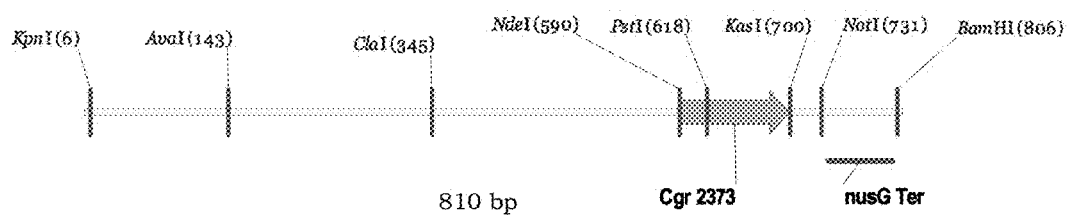
FIG. 1 shows the structure of the EXC1 DNA-fragment.

SEQ ID NO: 1 shows the EXC1 DNA-fragment
SEQ ID NO: 2 shows the MAG DNA-fragment
SEQ ID NO: 3 shows the primer P1
SEQ ID NO: 4 shows the primer P2
SEQ ID NO: 5 shows the Int4 DNA-fragment
SEQ ID NO: 6 shows the Int5 DNA-fragment
SEQ ID NO: 7 shows the Int1 DNA-fragment
SEQ ID NO: 8 shows the Int18 DNA-fragment
SEQ ID NO: 9 shows the Int19 DNA-fragment
SEQ ID NO: 10 shows the primer P3
SEQ ID NO: 11 shows the primer P4
SEQ ID NO: 12 shows the primer P5
SEQ ID NO: 13 shows the primer P6
SEQ ID NO: 14 shows the primer P7
SEQ ID NO: 15 shows the primer P8
SEQ ID NO: 16 shows the primer P9
SEQ ID NO: 17 shows the primer P10
SEQ ID NO: 18 shows the primer P11
SEQ ID NO: 19 shows the primer P12
SEQ ID NO: 20 shows the primer P13
SEQ ID NO: 21 shows the primer P14
SEQ ID NO: 22 shows the primer P15
SEQ ID NO: 23 shows the primer P16
SEQ ID NO: 24 shows the primer P17
SEQ ID NO: 25 shows the primer P18
SEQ ID NO: 26 shows the primer P19
SEQ ID NO: 27 shows the primer P20
SEQ ID NO: 28 shows the primer P21
SEQ ID NO: 29 shows the primer P22
SEQ ID NO: 30 shows the primer P23
SEQ ID NO: 31 shows the primer P24
SEQ ID NO: 32 shows the primer P25
SEQ ID NO: 33 shows the primer P26
SEQ ID NO: 34 shows the exenatide, protein
SEQ ID NO: 35 shows the trastuzumab, heavy chain, protein
SEQ ID NO: 36 shows the trastuzumab, light chain, protein
SEQ ID NO: 37 shows the intein MAG, protein
SEQ ID NO: 38 shows the intein Int4, protein
SEQ ID NO: 39 shows the intein Int5, protein
SEQ ID NO: 40 shows the intein Int1, protein
SEQ ID NO: 41 shows the intein Int18, protein
SEQ ID NO: 42 shows the intein Int19, protein
SEQ ID NO: 43 shows the Cgl0278, gene
SEQ ID NO: 44 shows the Cgl0278, protein
SEQ ID NO: 45 shows the mrcB, gene
SEQ ID NO: 46 shows the MrcB, protein
SEQ ID NO: 47 shows the intein MAG, gene
SEQ ID NO: 48 shows the intein Int4, gene
SEQ ID NO: 49 shows the intein Int5, gene
SEQ ID NO: 50 shows the intein Int1, gene
SEQ ID NO: 51 shows the intein Int18, gene
SEQ ID NO: 52 shows the intein Int19, gene
SEQ ID NO: 53 shows the exenatide, gene SEQ ID NO: 54 shows the trastuzumab, heavy chain, gene
SEQ ID NO: 55 shows the trastuzumab, light chain, gene
SEQ ID NO: 56 shows the PS1, protein
SEQ ID NO: 57 shows the PS2 (CspB), protein
SEQ ID NO: 58 shows the SlpA (CspA), protein
SEQ ID NO: 59 shows the PS2 (CspB), gene
SEQ ID NO: 60 shows the plasmid pPKSherFabHL
SEQ ID NO: 61 shows the primer P27
SEQ ID NO: 62 shows the primer P28
SEQ ID NO: 63 shows the primer P29
SEQ ID NO: 64 shows the primer P30
SEQ ID NO: 65 shows the CBD DNA-fragment
SEQ ID NO: 66 shows the chitin binding domain, protein
SEQ ID NO: 67 shows the primer P31
SEQ ID NO: 68 shows the primer P32
SEQ ID NO: 69 shows the primer P33
SEQ ID NO: 70 shows the primer P34
SEQ ID NO: 71 shows the primer P35
SEQ ID NO: 72 shows the primer P36
SEQ ID NO: 73 shows the primer P37
SEQ ID NO: 74 shows the pEXC1-CspB(50)-exe-MAG-CBD
SEQ ID NO: 75 shows the leader peptide of beta-lactamase

DESCRIPTION OF THE PREFERRED EMBODIMENTS

1. Coryneform Bacterium

The present invention provides a coryneform bacterium having an ability to produce a heterologous fusion protein by secretory production, which has been modified to express the nucleic acid sequence encoding a heterologous fusion protein (henceforth also referred to as the «bacterium of the present invention» or the «coryneform bacterium of the present invention»).

In the present invention, the secretory production of a heterologous fusion protein means that the protein is synthesized by the bacterial cell and transported out of the bacterial cell into an extracellular environment, for example, a culture medium. In such a sense, the heterologous fusion protein is extracellularly transported by the bacterial cell. The secretory production of heterologous fusion proteins can also include a case where the molecules of the fusion proteins eventually exist in the medium in completely free forms, a case where the molecules of the fusion proteins exist in the cell surface layer, and a case where a part of the molecules of the fusion proteins exist in the medium and the reminder part of the molecules exist in the cell surface layer.

Therefore, the «ability to produce a heterologous fusion protein by secretory production» refers to an ability of the bacterium to synthesize the heterologous fusion protein, secrete it into the medium and/or the cell surface layer, and accumulate it in the medium and/or the cell surface layer to such an extent that the heterologous fusion protein can be collected from the medium and/or the cell surface layer, when the bacterium is cultured in the medium. As for the accumulation amount, for example, the accumulation amount in the medium may be 10 µg/L or more, 1 mg/L or more, 100 mg/L or more, or 1 g/L or more. Also, as for the accumulation amount, for example, the accumulation amount in the cell surface layer may be to such an extent that if the heterologous protein in the cell surface layer is collected and suspended in the same volume of liquid as the medium, the concentration of the heterologous protein in the suspension is 10 µg/L or more, 1 mg/L or more, or 100 mg/L or more.

Coryneform Bacteria

In the present invention, the coryneform bacteria are aerobic gram-positive bacilli, and include *Corynebacterium* bacteria, *Brevibacterium* bacteria, *Microbacterium* bacteria, and so forth. The coryneform bacteria include bacteria which have previously been classified into the genus *Brevibacterium* but are presently united into the genus *Corynebacterium* (Liebl W. et al., *Int. J. Syst. Bacteriol.*, 1991, 41:255-260). The coryneform bacteria also include bacteria which have previously been classified into *Corynebacterium ammoniagenes* but are presently reclassified into *Corynebacterium stationis* by nucleotide sequence analysis of 16S rRNA and so forth (Bernard K. A. et al., *Int. J. Syst. Evol. Microbiol.*, 2010, 60:874-879). Advantages of use of the coryneform bacteria include the fact that they inherently secrete an extremely smaller amount of proteins in the outside of cells compared with fungi, yeasts, and *Bacillus* bacteria, which are conventionally used for secretory production of proteins, and therefore purification process of a heterologous fusion protein produced by secretory production can be simplified or eliminated, the fact that they can grow well in a simple medium containing a saccharide, ammonia, mineral salts, etc., and therefore they are excellent in view of cost of medium, culture method, and culture productivity, and so forth.

Specific examples of such coryneform bacteria include the following species:
*Corynebacterium acetoacidophilum*
*Corynebacterium acetoglutamicum*
*Corynebacterium alkanolyticum*
*Corynebacterium ammoniagenes* (*Corynebacterium stationis*)
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium album*
*Brevibacterium cerinum*
*Microbacterium ammoniaphilum*

Specific examples of such coryneform bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium ammoniagenes* (*Corynebacterium stationis*) ATCC 6871, ATCC 6872
*Corynebacterium callunae* ATCC 15991
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium thermoaminogenes* AJ12340 (FERM BP-1539)

*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869
*Brevibacterium roseum* ATCC 13825
*Brevibacterium saccharolyticum* ATCC 14066
*Brevibacterium thiogenitalis* ATCC 19240
*Brevibacterium album* ATCC 15111
*Brevibacterium cerinum* ATCC 15112
*Microbacterium ammoniaphilum* ATCC 15354

These strains are available from, for example, the American Type Culture Collection (ATCC) (Address: P.O. Box 1549, Manassas, Va. 20108, United States of America). That is, each strain is given a unique registration number (www.atcc.org), and can be ordered by using this registration number. The registration number of each strain is listed in the catalogue of the ATCC.

In particular, the *C. glutamicum* AJ12036 strain (FERM BP-734), which was isolated from the wild-type strain, *C. glutamicum* ATCC 13869, as a streptomycin (Sm) resistant mutant strain, is predicted to have a mutation in the functional gene responsible for secretion of proteins, and shows an extremely high secretory production ability for proteins as high as about 2 to 3 times in terms of accumulated amount of proteins under optimum culture conditions, compared with the parent strain (wild-type strain), and therefore it is preferred as a host bacterium. The AJ12036 strain (FERM BP-734) was originally deposited at the National Institute of Bioscience and Human-Technology, Agency of Industrial Science and Technology (Currently, the incorporated administrative agency, National Institute of Technology and Evaluation, International Patent Organism Depositary, AIST Tsukuba Central 6, 1-1, Higashi 1-Chome, Tsukuba-shi, Ibaraki-ken, 305-8566, Japan) on Mar. 26, 1984 as an international deposit, and assigned an accession number of FERM BP-734.

Moreover, a strain having an enhanced ability to produce a heterologous fusion protein by secretory production may be selected from coryneform bacteria obtained from such coryneform bacteria as mentioned above as a parent strain by using a mutagenesis method or a genetic recombination method, and used as a host. For example, after a parent strain is treated with ultraviolet irradiation or a chemical mutation agent such as N-methyl-N'-nitrosoguanidine, a strain having an enhanced ability to produce a protein by secretory production can be selected.

Furthermore, if a strain obtained by modifying such a strain as mentioned above so that it does not produce a cell surface layer protein as the host, purification of the heterologous fusion protein secreted in the medium becomes easy, and therefore it is particularly preferred. Such modification can be carried out by introducing a mutation into a coding region of the cell surface layer protein or an expression control region thereof on a chromosome by mutagenesis or genetic recombination. Examples of coryneform bacterium modified so that it does not produce a cell surface layer protein include the *C. glutamicum* YDK010 strain (WO2004/029254), which is a cell surface layer protein PS2 deficient strain of the *C. glutamicum* AJ12036 strain (FERM BP-734).

The coryneform bacterium having an ability to produce a heterologous fusion protein by secretory production can be obtained by introducing a genetic construct for secretory expression of the heterologous fusion protein into such a coryneform bacterium as mentioned above so that the construct is harbored by the bacterium. That is, the bacterium of the present invention has a genetic construct for secretory expression of a heterologous fusion protein. The «genetic construct» for secretory expression of a heterologous protein and a method for introducing it will be explained later.

The bacterium can be obtained by modifying a coryneform bacterium having an ability to produce a heterologous fusion protein by secretory production so that activity of a penicillin-binding protein and activity of a cell surface layer protein are reduced. Alternatively, the bacterium can also be obtained by modifying a coryneform bacterium so that activity of a penicillin-binding protein and activity of a cell surface layer protein are reduced, and then imparting an ability to produce a heterologous fusion protein by secretory production to it. Furthermore, the bacterium can also be obtained by modifying a coryneform bacterium of which activity of a cell surface layer protein has been intrinsically reduced so that the bacterium has an ability to produce a heterologous fusion protein and activity of a penicillin-binding protein is reduced. In the present invention, the modification and impartation of the ability for constructing the bacterium can be carried out in an arbitrary order. The bacterium may be obtained from a bacterium that can produce a heterologous fusion protein by secretory production before it is modified so that activity of a penicillin-binding protein and/or activity of a cell surface layer protein are reduced. In addition, the bacterium may also be obtained from a bacterium that cannot produce a heterologous fusion protein by secretory production even when it has a genetic construct for secretory expression of a heterologous fusion protein before it is modified so that activity of a penicillin-binding protein and/or activity of a cell surface layer protein are reduced, which comes to be able to produce the heterologous fusion protein by secretory production as a result of such modification that the activity of the penicillin-binding protein and/or activity of a cell surface layer protein are reduced. In addition, the bacterium may be further modified so that expression of a gene encoding a protease or a gene encoding a protein having a region homologous to a motif of a protease is increased.

Protein

The phrase protein produced by secretory production refers to a concept of protein including a peptide such as oligopeptide or polypeptide. For example, an oligopeptide can be a peptide consisting of between 2 and about 20 amino acid residues and may include dipeptides, tripeptides, tetrapeptides, pentapeptides, etc.; and polypeptide can be a peptide consisting of more than about 20 amino acid residues. The phrases «protein» and «peptide» are those concepts which can be unambiguously understood by the person skilled in the art.

Heterologous Protein

The phrase «heterologous protein» refers to an exogenous protein for the coryneform bacterium that synthesizes and secretes that protein. The heterologous protein may be, for example, a protein derived from a microorganism, a protein derived from a plant, a protein derived from an animal, a protein derived from a virus, or even a protein of which amino acid sequence is artificially designed. In this context, "derived from" is synonymous with "native to". The heterologous protein may be a monomer protein or a multimer protein. The multimer protein refers to a protein that may exist as a multimer consisting of two or more subunits. In the multimer, the subunits may be linked by covalent bonds such as disulfide bonds or by non-covalent bonds such as hydrogen bonds, ionic bonds, van der Waals forces, and hydrophobic interactions, or linked by a combination of these. The multimer may include one or more intermolecular disulfide bonds. The multimer may be a homo-multimer consisting of a single kind of subunit, or may be a hetero-multimer consisting of two or more kinds of subunits. In the case where the multimer is a hetero-multimer, it is sufficient that at least one subunit selected from the subunits constituting the hetero-multimer is a heterologous protein. That is, all the subunits may be heterologous, or only a part of the subunits may be heterologous. It is also possible that a part of a naturally endogenous protein for the coryneform bacterium is artificially designed thus constituting a heterologous part of the protein. A naturally endogenous protein for the coryneform bacterium or a part of that can be covalently linked through the peptide bond to a heterologous protein or a part of that, or an artificially designed amino acid sequence. Such complex protein also contributes to the phrase «heterologous protein». The heterologous protein to be produced may consist of a single kind of protein, or two or more kinds of proteins. Moreover, when the heterologous protein is a hetero-multimer, only one kind of subunit may be produced, or two or more kinds of subunits may be produced. That is, the secretory production of the heterologous protein includes secretory production of one or all the subunits constituting a desired heterologous protein, as well as secretory production of only a part of the subunits constituting a desired heterologous protein. A specific example of the heterologous protein is a heterologous fusion protein.

Fusion Protein

The phrase «fusion protein» refers to a protein expressed from a fusion gene, which is created by joining two or more genes. That is, one gene is ligated upstream of another one or more genes encoding the proteins constituting a fusion protein. A fusion protein consisting of two proteins, which when expressed from a common nucleic acid sequence that includes the genes encoding said proteins, is a particular example of the presently disclosed subject-matter. So long as the fusion protein consists of two or more proteins, the terminal proteins of the molecule are referred to as the N-terminal and the C-terminal parts of the fusion protein. That is, the N-terminal part of a fusion protein is the protein located at the N-terminus of the amino acid sequence constituting the fusion protein; and the C-terminal part of a fusion protein is the protein located at the C-terminus of the amino acid sequence constituting the fusion protein. It is generally accepted that the N-terminus of the amino acid sequence is counted from the terminal amino group ($H_2N—$) of the sequence. Contrary, the C-terminus of the amino acid sequence is counted from the terminal carboxylic group (—COOH) of the sequence. Therefore, the fusion protein can consist merely of one N-terminal and one C-terminal part. However, if the fusion protein is encoded by more than two genes, said protein may have one or more «internal proteins» linked to the N-terminal and C-terminal parts. In such a fusion protein, the N-terminus of the internal protein is linked to the C-terminus of the N-terminal protein, and the C-terminus of the internal protein is linked to the N-terminus of the C-terminal protein or the N-terminus of the second internal protein of which the C-terminus is linked to the N-terminus of the third internal protein or the N-terminus of the C-terminal protein. A fusion protein having merely one N-terminal and one C-terminal part is a particular example.

The fusion protein consisting of two or more proteins may include two structural regions, hereafter referred to as the «extein region» (also referred to as the «extein») and the «intein region» (also referred to as the «intein»). In the fusion protein consisting of two or more proteins, the N-terminal part per se or the N-terminal part linked to one or more internal proteins is referred to as the «extein». The C-terminal part per se or the C-terminal part linked to one or more internal proteins of the fusion protein consisting of two or more proteins is referred to as the «intein». Structural and functional features can be applied to an intein as described hereafter. Therefore, as soon as the intein is determined as being in compliance with structural and functional requirements for inteins, the remaining part of the fusion protein can be determined as the extein.

Further, the heterologous fusion protein to be produced by secretory production may be a protein containing a pro-structure part (proprotein) within the extein region. In the case where the heterologous fusion protein to be produced by secretory production is a proprotein, the heterologous fusion protein to be eventually obtained by the method of the present invention may be the proprotein or may not be the proprotein. That is, the proprotein may be made into a mature fusion protein by cleavage of the pro-structure part in the extein region. The cleavage can be attained with, for example, a protease. When a protease is used, in view of the activity of the protein to be eventually obtained, the proprotein is generally cleaved preferably at a position substantially the same as that of the natural protein, or more preferably at a position exactly the same as that of the natural protein to obtain the same mature protein as the natural mature protein. Therefore, a specific protease that cleaves the proprotein at such a position that the same protein as the naturally occurring mature protein is generated is most preferred. However, the N- and/or C-termini of the heterologous fusion protein to be eventually obtained may not be the same as that of the natural protein as described above. For example, depending on type, purpose of use, etc. of the heterologous fusion protein to be produced, a protein having the N- and/or C-termini longer or shorter by one or more amino acid residues compared with the natural protein may have more appropriate activity. Proteases usable in the present invention include, for example, commercially available proteases such as Dispase (produced by Boehringer Mannheim) as well as those obtainable from culture broth of a microorganism such as culture broth of actinomycetes. Such proteases can be used in an unpurified state, or may also be used after purification to an appropriate purity as required.

Extein

The extein can be, for example, a heterologous protein of a monomer structure (also referred to as the «monomer heterologous protein») or a subunit of the heterologous protein having a multimer structure (also referred to as a subunit of the «multimer heterologous protein»), or a part of these shortened by one or more amino acid residues from the N- and/or C-terminus of the amino acid sequence. It is also possible that a monomer heterologous protein or a subunit of the multimer heterologous protein is extended by one or more amino acid residues from the N- and/or C-terminus of the amino acid sequence. Of course, a monomer heterologous protein or a subunit of the multimer heterologous protein can be shortened and extended by one or more amino acid residues from the N- and/or C-terminus concurrently. That is, when the N-terminus (C-terminus) of the protein is shortened by one or more amino acid residues or even unmodified, the C-terminus (N-terminus) of the protein can be extended by one or more amino acid residues or even unmodified. The amino acid sequence of an extein can be chosen from naturally occurring amino acid sequences, or reasonably modified natural amino acid sequences, or artificially designed amino acid sequences. Furthermore, the N- and C-termini of an extein can also be modified, for example, through the shortening and/or extending by one or more amino acid residues, or even left unmodified. Therefore, an extein may be referred to as the «target protein». Specific examples of the «target protein» will be mentioned later.

So long as the heterologous fusion protein includes an extein, the heterologous fusion protein eventually obtained by the method of the present invention may have a target protein as having the primary structure chosen from the naturally occurring amino acid sequences, or artificially designed as a part of the naturally occurring amino acid sequence by the substitution, deletion, insertion and/or addition of one or more amino acid residues, or artificially designed as a complete amino acid sequence. Although the number of the gone or more amino acid residues may differ depending on the full length or structure of the objective heterologous protein, specifically, it can be 1 to 30, 1 to 20, 1 to 10, or 1 to 5.

Although the extein is not particularly limited so long as secretory production of the heterologous fusion protein is attained, it may contain a linker so that the linker is located in between a target protein and an intein in the structure of a heterologous fusion protein. That is, a target protein and an intein can be joined through the linker consisting of one or more amino acid residues. The linker may have a length of 1, 2, 3, 4, 5, 10, 20, 50, 100 or more amino acid residues; specifically, it may be 1 to 3 amino acid residues. The N-terminus of the linker is linked to the C-terminus of a target protein and the C-terminus of the linker is linked to the N-terminus of an intein through the peptide bond. The linker can be ended at the C-terminus by the —NH—CH(R1)-CO—NH—CH(R2)-CO— motif, where R1 and R2 are the side-chain groups of any proteinogenic L-amino acid of the same kind or different kinds, so long as the linker has a length of two or more amino acid residues. That is, R1 and R2 can be a side-chain group of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine or L-valine; wherein R1 and R2 can be of the same chemical structure or different chemical structures. For example, R1 is the side-chain group of any proteinogenic L-amino acid and R2 is the side-chain group of L-cysteine, or R1 is hydrogen and R2 is the side-chain group of L-cysteine.

The phrase «peptide bond» refers to a covalent chemical bond —CO—NH— formed between two molecules when the carboxy part of one molecule, referred to as a carboxy component, reacts with the amino part of another molecule, referred to as an amino component, causing the release of a molecule. For example, proteinogenic L-amino acids can form the peptide bond upon joining with the release of a molecule of water. Therefore, proteins and peptides can be regarded as chains of amino acid residues held together by peptide bonds. A peptide bond can be also referred to as an «amide bond».

Intein

The inteins from various host organisms of Eukarya, Eubacteria, and Archaea can be used to eventually obtain a heterologous fusion protein by the method of the present invention. A collection of more than 115 kinds of inteins is provided by the InBase, The Intein Database (Perler F. InBase, the intein database, Nucleic Acids Res., 2002, 30:383-384; tools.neb.com/inbase/list.php). There are two kinds of inteins: the classical inteins containing the DOD-type homing endonuclease, and the mini-inteins. The DOD endonuclease-containing inteins and the mini-inteins are about 450-600 and about 134-300 amino acid residues in length, respectively. Both kinds of inteins have the N-terminal domain of 150-200 residues in length, C-terminal domain of 25-40 residues in length, and the internal domain which is a DOD endonuclease domain for the DOD endonuclease-containing inteins or a linker region domain for the mini-inteins (Starokadomskyy P. L. Protein splicing, Mol. Biol., 2007, 41(2):278-293). The N-splicing domain of two kinds of inteins includes the motifs A, N2, B, and N4. However, some inteins may lack of N4. The C-splicing domain of mini-inteins includes the motifs F and G. An additional motif H precedes the motif F in DOD endonuclease-containing inteins. Motifs C, D, and E contribute to the structure of the DOD endonuclease domain and are located in between the motifs N4 and H.

Motif A is a short N-terminal sequence of 13 residues, of which the first and the second residues are highly conserved. Position 1 at the N-terminus of an intein is almost always occupied by Cys, Ala, Gln or Ser. Position 13 is occupied by Gly, Ala, Lys, Thr, Arg, Tyr or Asn. The N-terminal amino acid residue of intein (Cys, Ala, Gln or Ser) can be involved in acyl rearrangement. The more detailed explanation for the acyl rearrangement is given hereafter.

Motif N2 consists of 7 residues, of which Asp5 or Glu5 is highly conserved and is most often preceded by Gly.

Motif B consists of 14 residues. Position 10 is occupied by His in all known inteins. Position 7 is most often occupied by Thr.

Motif N4 consists of 16 residues including highly conserved Asp or Glu in position 11. As in motif N2, the Asp or Glu residue is usually preceded by Gly10.

Motifs C and E form a basis of the DOD endonuclease domain and have sequences of nine and ten residues. Both motifs are separated by a linker of 90-130 residues. The active center of the enzyme contains conserved Gly residues, which are in positions 3 and 9 of motif C and 4 and 10 of motif E. In addition, each motif harbors catalytically active Asn and Lys.

Motif D of eight residues in length is in the linker between motifs C and E. The Lys residue in position 2 may be required for an endonuclease activity of the DOD domain.

Motif H consists of 19 amino acid residues, of which Leu13 and Leu14 are rather conserved. Motifs C, D, E, and H form the DOD endonuclease domain.

Motifs F and G form the C-terminal domain. Motif F consists of 16 residues, half of which are highly conserved. Motif G is a short C-terminal sequence of seven residues. Motifs F and G are separated by a short linker, consisting of two to five residues. The C-terminal amino acid residue of the motif G is Asn, Gln or Asp; the last but one is His.

The documents Starokadomskyy P. L. Protein splicing, Mol. Biol., 2007, 41(2):278-293 and Perler F. InBase, the intein database, Nucleic Acids Res., 2002, 30:383-384 can be exclusively incorporated herein as references to the structural organization of inteins.

The inteins are not limited to those mentioned in the InBase, The Intein Database tools.neb.com/inbase/list.php). The objective amino acid sequence can be searched against the intein database using the BLAST (Basic Local Alignment Search Tool) service to find a new intein or a homolog of the known intein. The BLAST service is provided by the InBase, The Intein Database (tools.neb.com/.about.vincze/blast/index.php?blastdb=inbase) or the National Center for Biotechnology Information (NCBI, blast.ncbi.nlm.nih.gov).

The following inteins, as non-limiting examples, can be used: Mmag Magn8951 BIL (for the sake of simplicity herein referred to as MAG) from *Magnetospirillum magnetotacticum* MS-1 (Amitai G. et al., *Mol. Microbiol.*, 2003, 47(1):61-73), Pvu PRP8 (PVU) from *Penicillium vulpinum* (formerly *P. claviforme*), Pab Pol-II (PAB) from *Pyrococcus abyssi*, Mxe GyrA (MXE) from *Mycobacterium xenopi* strain IMM5024, Mth R1R1 (MTH) from *Methanobacterium thermoautotrophicum* (Evans T. C. Jr. et al., *J. Biol. Chem.*, 1999, 274(7):3923-3926), Ctr VMA (SCE) from *Candida tropicalis* (nucleus), Ter ThyX (TER) from *Trichodesmium erythraeum* IMS101, Aha DnaE-c and Aha DnaE-n (SSP) from *Aphanothece halophytica*, Tvu DnaE-c and Tvu DnaE-n (TVU) from *Thermosynechococcus vulcanus*, and so forth. Furthermore, homologous intein sequences can be found using the BLAST analysis. For example, the inteins homologous to the Mmag Magn8951 BIL intein from *M. magnetotacticum* MS-1 can be found as iAAQ from *Aeromonas aquariorum* AAK1, as iBLA from *Brevibacillus laterosporus* LMG 15441, as iEKD from uncultured bacterium, as iSPH from *Microscilla marina*, and as iMIC from *Sphingobacterium* sp. 21 (refer to the Examples for details).

A protein is considered to be an «intein» so long as it has an «activity of acyl rearrangement» when linked to an extein through the peptide bond in the heterologous fusion protein produced by secretory production as described in the present invention. The «acyl rearrangement» proceeds in two stages, more specifically, two consecutive nucleophilic displacement reactions which result in trans-esterification reaction, that is, a shift of the extein C-terminus from the peptide bond linking extein and intein in the heterologous fusion protein to the nucleophilic group of a reactant. The mechanism of the acyl rearrangement is described in Perler F. InBase, the intein database, *Nucleic Acids Res.*, 2002, 30:383-384 and Starokadomskyy P. L. Protein splicing, *Mol. Biol.*, 2007, 41(2):278-293. The phrase «reactant» is explained hereafter.

At the first stage of the acyl rearrangement a nucleophilic group of the N-terminal amino acid residue of the intein attacks a carbon atom of the neighboring peptide bond linking the extein and intein. Although, the kinds of the N-terminal amino acid residues of inteins are mentioned hereafter, the residues can be, for example, those residues which have thiol group (—SH) or hydroxyl group (—OH) terminating a side-chain group of a proteinogenic L-amino acid. When an L-cysteine residue is located at the N-terminus of an intein, the thiol group (—SH) can be regarded as the nucleophilic group as set forth above. In this case, the first stage of the acyl rearrangement is referred to as «N—S shift». When L-serine or L-threonine residue is located at the N-terminus of an intein, the hydroxyl group (—OH) can be regarded as the nucleophilic group as set forth above. In this case, the first stage of the acyl rearrangement is referred to as «N—O shift». The N—S shift results in formation of the thioester intermediate having the thioester bond (—CO—S—) in between extein and intein. The N—O shift results in formation of the ester intermediate having the ester bond (—CO—O—) in between extein and intein. As a result of the first stage of the acyl rearrangement, the C-terminus of extein shifts from the peptide bond linking extein and intein to the side-chain group of the amino acid residue located at the N-terminus of intein. At the second stage of the acyl rearrangement, a nucleophilic group of a reactant attacks carbon atom of the thioester bond or ester bond in between extein and intein.

As the «reactant», any organic or inorganic molecule can be used so long as it has one or more nucleophilic groups having a nucleophilic atom such as carbon atom, nitrogen atom, oxygen atom, and so forth, and can react with the thioester bond or ester bond, which is obtained as a result of the first stage in between extein and intein, in nucleophilic substitution reaction to attain the nucleophilic acyl substitution (March J., Advanced Organic Chemistry, $4^{th}$ ed., Wiley, New York (USA), 1992; Carey F. A., Organic Chemistry, $6^{th}$ ed., McGraw-Hill, New York (USA), 2006).

The acyl rearrangement results in cleavage of the intein from the heterologous fusion protein produced by secretory production and formation of a molecule consisting of an extein and a reactant residue linked to the C-terminus of the extein. Thus, the phrase «an activity of acyl rearrangement» can mean a property of a protein to take part in the acyl rearrangement as described above. So long as an objective protein has the activity of acyl rearrangement, it can be referred to as the «intein». It may be the case that the protein initially is unable to take part in the acyl rearrangement, but due to one or more modifications introduced into the amino acid sequence of the protein, said protein can be imparted with an activity of acyl rearrangement. Therefore, any protein can be modified in such a way that it can take part in the acyl rearrangement and, thus, referred to as an intein. Means for introducing substitutions, deletions, insertions, and/or additions of one or several amino acid residues into a protein are explained hereafter. A heterologous fusion protein to be produced by secretory production may be referred to as the «protein having an activity of acyl rearrangement» so long as the intein of such protein has the activity of acyl rearrangement.

The amino acid residue at the N-terminus of an intein can be preferably L-cysteine, L-threonine, L-serine or L-alanine residue, more preferably L-cysteine, L-threonine or L-serine residue, and particularly preferably L-cysteine residue.

Amines, thiols, alcohols, and so forth can be used as «organic reactants». Primary amines and secondary amines having, respectively, one or two hydrogen atoms substituted with organic radicals can be used to react with the thioester bond or ester bond in between extein and intein. In such a case, amide bond (—CO—NH—) is formed in between the extein and the reactant residue, and the reaction is referred to as «amidation reaction». Thiols having one, two, three or more thiol groups linked to organic radicals can be used to react with the ester bond in between extein and intein. In such a case, thioester bond (—CO—S—) is formed in between the extein and the reactant residue, and the reaction is referred to as «thioesterification reaction». It is also possible to react thiols with the thioester bond in between extein and intein so long as conditions of the nucleophilic acyl substitution reaction, such as, for example, the kind of a reactant, are appropriately chosen so that the leaving group (i.e. the intein) can be substituted with a thiol residue. Alcohols having one, two, three or more hydroxyl groups linked to organic radicals can be reacted with the thioester bond in between extein and intein. In such a case, ester bond (—CO—O—) is formed in between the extein and the reactant residue, and the reaction is referred to as an «esterification reaction». It is also possible to react alcohols with the ester bond in between extein and intein so long as conditions of the nucleophilic acyl substitution reaction, such as, for example, the kind of reactant, are appropriately chosen so that the leaving group (i.e. the intein) can be substituted with the alcohol residue. Alkyl, alkenyl, alkynyl, aryl, and so forth, and derivatives thereof having one or more hydroxyl groups, thiol groups, amino groups, aldehyde groups, carboxyl groups, halogen groups, and so forth can be used as organic radicals. Nucleosides, nucleotides, nucleic acids of different length, for example, from 2 to 10, or from 2 to 20, or from 2 to 50, or from 2 to 100, or from 2 to 200, or from 2 to 500, or from 2 to more than 500 nucleotides in length can also be used as organic radicals. Amino acids or peptides of different length, for example, from 2 to 5, or from 2 to 10, or from 2 to 20, or from 2 to 50, or from 2 to 100, or from 2 to more than 100 amino acid residues in length can also be used as organic radicals. Proteins such as bioactive proteins, receptor proteins, antigenic proteins as described hereafter can also be used as organic radicals. Dyes, fatty acids, carbohydrates, heterocyclic compounds, biotin; low, medium and high molecular weight drugs; radiolabeled molecules; and so forth can be used as organic radicals. Ammonia, hydroxylamine, sodium sulfide, and so forth are particular examples of the «inorganic reactants».

The rate of the acyl rearrangement may vary depending on, for example, the primary, secondary, tertiary structure of an intein and/or extein including a heterologous fusion protein produced by secretory production; environmental conditions such as ionic strength, acidity (pH), temperature, medium composition; purity of a sample of the heterologous fusion protein; and so forth. Means for obtaining heterologous fusion proteins having the activity of acyl rearrangement are described in the Examples hereafter.

It is preferable that three-dimensional structure, function and/or activity of a heterologous fusion protein produced by secretory production, or the extein or intein parts of the heterologous fusion protein, or a molecule consisting of an extein and a reactant residue linked to the C-terminus of the extein produced as a result of the acyl rearrangement, or an intein produced as a result of the acyl rearrangement is/are not affected at the first stage or second stage, or both stages of the acyl rearrangement to such an extent that the three-dimensional structure and/or function is/are completely or partially disturbed, or the activity is completely or partially disappeared. More specifically, the activity may be 30% or more, 50% or more, 70% or more, 90% or more, or 100% of that observed in a heterologous fusion protein produced by secretory production, or the extein or intein parts of the heterologous fusion protein, or a molecule consisting of an extein and a reactant residue linked to the C-terminus of the extein produced as a result of the acyl rearrangement, or an intein produced as a result of the acyl rearrangement, subjected to the first stage or second stage, or both stages of the acyl rearrangement.

Although, inteins have a certain characteristic of sequence common over biological species, an intein that has an activity of acyl rearrangement as to a certain extein does not necessarily exhibit the same activity as to another extein. Therefore, when an intein having an activity of acyl rearrangement as to another extein is used, an intein that has an activity of acyl rearrangement as to an objective extein may be appropriately chosen. It is therefore acceptable that any intein can be used to obtain a heterologous fusion protein produced by secretory production as described in the present invention so long as the intein has an activity of acyl rearrangement when linked to an extein through the peptide bond in the heterologous fusion protein. The appropriate intein having an activity of acyl rearrangement can be found by the BLAST search in the InBase, The Intein Database. It is also possible to find one or more homologues of the intein using the BLAST analysis when searched in the InBase, The Intein Database or an amino acid sequences database such as the Protein Database (NCBI, www.ncbi.nlm.nih.gov/protein). The activity of acyl rearrangement of the intein selected as a result of the BLAST search can be determined as described hereafter.

The following inteins, as non-limiting examples, can be used.

The wild-type nucleic acid sequence of SEQ ID NO: 47 (NCBI accession No. NZ_AAAP01003875; version NZ_AAAP01003875.1, GI: 23016286; reverse complement, 514 bp-936 bp) encodes the Mmag Magn8951 BIL (MAG) intein having the amino acid sequence of SEQ ID NO: 37 from *Magnetospirillum magnetotacticum* MS-1.

The wild-type nucleic acid sequence of SEQ ID NO: 48 (GenBank accession No. AM042016; version AM042016.1, GI: 94442880; 152 bp-634 bp) encodes the Pvu PRP8 (PVU) intein having the amino acid sequence of SEQ ID NO: 38 from *Penicillium vulpinum*.

The wild-type nucleic acid sequence of SEQ ID NO: 49 (GenBank accession No. BA000022; version BA000022.2, GI: 47118304; 2323 bp-2691 bp) encodes the Ssp DnaE-n (SSP) intein having the amino acid sequence of SEQ ID NO: 39 from *Aphanothece halophytica*.

The wild-type nucleic acid sequence of SEQ ID NO: 50 (NCBI accession No. NC_000868; version NC_000868.1, GI: 14518450; 2863 bp-3417 bp) encodes the Pab Pol-II (PAB) intein having the amino acid sequence of SEQ ID NO: 40 from *Pyrococcus abyssi*.

The wild-type nucleic acid sequence of SEQ ID NO: 51 (NCBI accession No. NZ_AFRV01000005; version NZ_AFRV01000005.1, GI: 339009619; 4990 bp-5388 bp) encodes the iBLA intein having the amino acid sequence of SEQ ID NO: 41 from *Brevibacillus laterosporus* LMG 15441.

The wild-type nucleic acid sequence of SEQ ID NO: 52 (NCBI accession No. AMFJ01011091; version AMFJ01011091.1, GI: 406968816; 3226 bp-3612 bp) encodes the iEKD intein having the amino acid sequence of SEQ ID NO: 42 from uncultured bacterium ACD_28C00111.

Since there may be some differences in nucleotide sequence sequences between biological species or strains, the wild-type genes encoding inteins are not limited to the genes encoding inteins described in, for example, the InBase, The Intein Database or the Protein Database (NCBI), or the intein genes specifically shown in SEQ ID NOs: 47, 48, 49, 50, 51, and 52, but may include genes which are variant nucleotide sequences of or homologous to the aforementioned nucleotide sequences, and which encode variants of the wild-type inteins. The phrase «a wild-type intein» refers to a native intein naturally expressed in a wild-type biological species. A wild-type intein can be encoded by the wild-type, or non-modified, gene naturally occurring in genome of a biological species.

The phrase «a variant of the wild-type intein» (also referred to as «a variant intein») can mean an intein which has one or several changes in the amino acid sequence compared with the wild-type sequence of the intein, whether they are substitutions, deletions, insertions, and/or additions of one or several amino acid residues, but still maintains an activity of acyl rearrangement similar to that of the wild-type intein. The number of changes in the variant intein depends on the position or the kind of amino acid residues in the three-dimensional structure of the intein. For example, one or more variant inteins can be obtained for an intein having the amino acid sequence of SEQ ID NO: 37, 38, 39, 40, 41 or 42 by introducing one or several changes into the sequence.

Although the number of the «one or several» amino acid residues may differ depending on the position in the three-dimensional structure or kinds of amino acid residues of the intein, specifically, the changes in the amino acid sequence can be, but are not strictly limited to, 1 to 30, in another example 1 to 15, in another example 1 to 10, and in another example 1 to 5, in the amino acid sequence corresponding to the wild-type intein. These changes in the variant intein can occur in regions of the intein that are not critical for the activity of the intein. This is because some amino acids have high homology to one another so that the activity is not affected by such a change, or the three-dimensional structure of the variant intein is not significantly changed relative to the wild-type or non-modified intein. For example, as the motifs A, N2, B, N4, C, D, E, H, F, and G of an intein may be required for activity, the intein regions corresponding to these motifs can be, therefore, subjected to the modification to the low extent or even left unmodified. Quite the contrary, the intein regions linking said motifs are less conservative and, therefore, can be subjected to one or more changes. For the clarity reason, the iBLA intein (SEQ ID NO: 41) and the iEKD intein (SEQ ID NO: 42) can be homologues of the MAG intein (SEQ ID NO: 37) (Tables 7 and 8). That is, the iBLA and iEKD inteins can be obtained from the MAG intein by introducing one or several changes in the amino acid sequence of the MAG intein.

Therefore, the variant inteins encoded by the intein genes may have a homology, defined as the parameter «identity» when using the computer program BLAST, of not less than 20%, not less than 30%, not less than 40%, not less than 50%, not less than 60%, not less than 70%, not less than 80%, not less than 90%, not less than 95%, or not less than 98% with respect to the entire amino acid sequences of the wild-type inteins so long as the activity of the variant inteins is maintained.

The exemplary substitution, deletion, insertion, and/or addition of one or several amino acid residues can be a conservative mutation(s). The representative conservative mutation is a conservative substitution. The conservative substitution can be, but is not limited to a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution Asn, Glu or Gln for Asp, substitution of Ser or Ala for Cys, substitution Asn, Glu, Lys, His, Asp or Arg for Gln, substitution Asn, Gln, Lys or Asp for Glu, substitution of Pro for Gly, substitution Asn, Lys, Gln, Arg or Tyr for His, substitution of Leu, Met, Val or Phe for Ile, substitution of Ile, Met, Val or Phe for Leu, substitution Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) so long as the mutation(s) is/are compensated by one or more secondary mutations in the different position(s) of amino acids sequence so that the activity of the variant intein is maintained and similar to that of the wild-type intein.

To evaluate the degree of intein or DNA homology, several calculation methods can be used, such as BLAST search, FASTA search and ClustalW method. The BLAST (Basic Local Alignment Search Tool, www.ncbi.nlm.nih.gov/BLAST/) search is the heuristic search algorithm employed by the programs blastp, blastn, blastx, megablast, tblastn, and tblastx; these programs ascribe significance to their findings using the statistical methods of Samuel K. and Altschul S. F. («Methods for assessing the statistical significance of molecular sequence features by using general scoring schemes» *Proc. Natl. Acad. Sci. USA,* 1990, 87:2264-2268; «Applications and statistics for multiple high-scoring segments in molecular sequences». *Proc. Natl. Acad. Sci. USA,* 1993, 90:5873-5877). The computer program BLAST calculates three parameters: score, identity and similarity. The FASTA search method is described by Pearson W. R. («Rapid and sensitive sequence comparison with FASTP and FASTA», *Methods Enzymol.,* 1990, 183: 63-98). The ClustalW method is described by Thompson J. D. et al. («CLUSTAL W: improving the sensitivity of progressive multiple sequence alignment through sequence weighting, position-specific gap penalties and weight matrix choice», *Nucleic Acids Res.,* 1994, 22:4673-4680).

Moreover, the intein gene can be a variant nucleotide sequence. The phrase «a variant nucleotide sequence» can mean a nucleotide sequence which encodes «a variant intein» using any synonymous amino acid codons according to the standard genetic code table (see, e.g., Lewin B., «Genes VII», 2004, Pearson Education, Inc., Upper Saddle River, N.J. 07458).

The phrase «a variant nucleotide sequence» can also mean, but is not limited to a nucleotide sequence which hybridizes under stringent conditions with the nucleotide sequence complementary to the sequence encoding the wild-type intein. Furthermore, the phrase «a variant nucleotide sequence» can also mean a nucleotide sequence which hybridizes under stringent conditions with a probe which can be prepared from the nucleotide sequence under stringent conditions so long as it encodes an active intein. «Stringent conditions» include those under which a specific hybrid, for example, a hybrid having homology, defined as the parameter «identity» when using the computer program BLAST, of not less than 20%, not less than 30%, not less than 40%, not less than 50%, not less than 60%, not less than 70%, not less than 80%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the nucleotide sequence complementary to the sequence encoding the wild-type intein may also be used. Such a probe can be produced by PCR using oligonucleotides as primers prepared on the basis of the wild-type intein sequence and a DNA-fragment containing the nucleotide sequence as a template. The length of the probe is recommended to be >50 bp; it can be suitably selected depending on the hybridization conditions, and is usually 100 bp to 1 kbp. For example, when a DNA-fragment having a length of about 300 bp is used as the probe, the washing conditions after hybridization can be exemplified by 2×SSC, 0.1% SDS at 50° C., 60° C. or 65° C.

As the genes encoding the wild-type inteins have already been elucidated (see above), the variant nucleotide sequences encoding variant inteins of the wild-type inteins can be obtained by PCR (polymerase chain reaction; refer to White T. J. et al., The polymerase chain reaction, *Trends Genet.*, 1989, 5:185-189) utilizing primers prepared based on the nucleotide sequence of the wild-type inteins and genome DNA as a template; or the site-directed mutagenesis method by treating a DNA containing the wild-type intein gene in vitro, for example, with hydroxylamine; or chemically synthesized as full-length gene structure.

In addition, the aforementioned explanations concerning variants of genes and inteins can also be applied mutatis mutandis to arbitrary proteins such as an extein, a target protein, a linker in between an extein and an intein, a penicillin-binding protein, a cell surface layer protein, and a heterologous fusion protein to be produced by secretory production in the present invention, and genes encoding them.

Target Protein

The non-limiting examples of the target protein produced by secretory production by the method of the present invention include, for example, bioactive proteins, receptor proteins, antigenic proteins to be used as vaccine, and enzymes. Examples of the enzymes include, for example, transglutaminases, proteases, endopeptidases, exopeptidases, aminopeptidases, carboxypeptidases, collagenases, chitinases, and so forth.

Examples of the bioactive proteins include, for example, growth factors, hormones, cytokines, antibody-related molecules. A bioactive protein may be an intact protein, or may be a part of a protein. Examples of a part of a protein include, for example, a part having physiological activity. Specific examples of a part having physiological activity include, for example, teriparatide, a bioactive peptide, which consists of 34 amino acid residues of N-terminus of parathyroid hormone (PTH).

Specific examples of the growth factor include, for example, epidermal growth factor (EGF), insulin-like growth factor (IGF), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyto growth factor (KGF-1 or FGF7, and KGF-2 or FGF10), and hepatocyte growth factor (HGF).

Specific examples of the hormone include, for example, insulin, glucagon, somatostatin, human growth hormone (hGH), parathyroid hormone (PTH), exenatide, and calcitonin. Exenatide is a glucagon-like peptide-1 agonist (GLP-1 agonist) of 39 amino acid residues in length. The nucleic acid sequence of SEQ ID NO: 53 (GenBank accession No. U77613; version U77613.1, GI: 1916066; 142 bp-258 bp) encodes the exenatide protein having the amino acid sequence of SEQ ID NO: 34 from *Heloderma suspectum*.

Specific examples of the cytokine include, for example, interleukins, interferons, tumor necrosis factors (TNFs).

Growth factors, hormones, and cytokines may not be strictly distinguished from each other. For example, a bioactive protein may be a protein belonging to a single group selected from growth factor, hormone, and cytokine, or may be a protein belonging to a plurality of groups selected from those.

The antibody-related molecule refers to a protein including a molecular species consisting of a single domain or a combination of two or more domains selected from domains that constitute a complete antibody. Examples of the domains that constitute a complete antibody include VH, CH1, CH2, and CH3, which are domains of a heavy chain, and VL and CL, which are domains of a light chain. The antibody-related molecule may be a monomer protein or a multimer protein so long as it includes the above-mentioned molecular species. In the case where the antibody-related molecule is a multimer protein, the antibody-related molecule may be a homo-multimer consisting of a single kind of subunit, or may be a hetero-multimer consisting of two or more kinds of subunits. Specific examples of the antibody-related molecule include, for example, complete antibodies, Fab, F(ab'), F(ab')$_2$, Fc, dimer consisting of the heavy chain (H chain) and the light chain (L chain), Fc-fusion proteins, the heavy chain (H chain), the light chain (L chain), single chain Fv (scFv), sc(Fv)$_2$, disulfide-linked Fv (sdFv), and diabody.

Fab (fragment, antigen binding) is a part of a complete antibody except for the Fc region of the H chain, and it is an antibody fragment consisting only of an antigen-binding region. Fab is a dimer consisting of one molecule of the Fab moiety of the H chain and one molecule of L chain, and they aggregate by a disulfide bond at the C-terminus. The complete antibody is an H2L2 tetramer, and has a huge molecular weight of about 150 kDa, whereas Fab has a small molecular weight of about 50 kDa, and therefore Fab is thought to show superior permeability for an objective tissue. Since Fab does not have the Fc region, it has neither complement activity nor crystallization ability, but since it has antigen-binding ability, it is mainly used for the purpose of neutralizing an antigen. Among the antibody drugs, Fab especially attracts attention in recent years.

Specific example of Fab includes, for example, a Fab for the trastuzumab consisting of the H chain of 228 amino acid residues in length and the L chain of 214 amino acid residues in length. The nucleic acid sequences of SEQ ID NOs: 54 and 55 encode the trastuzumab Fab H and L chains having amino acid sequences of SEQ ID NOs: 35 and 36, respectively.

F(ab') is a part of a complete antibody except for the Fc' region of the H chain. F(ab') is a dimer consisting of one molecule of the F(ab') moiety of the H chain and one molecule of the L chain, and they aggregate by a disulfide bond at the C-terminus. The reminder moiety of the H chain in F(ab') is longer than the reminder moiety of the H chain in Fab, and hence, in F(ab'), the disulfide bond moiety linking the H chains remains. Therefore, two molecules of F(ab') can form F(ab')$_2$ by a disulfide bond. F(ab') and F(ab')$_2$ can also be used as antibody drugs like a Fab fragment.

Fc (fragment, crystallizable) is an antibody fragment consisting only of the Fc region that participates in the complement activity and crystallization ability. A protein consisting of the Fc region of the H chain and another functional protein fused to each other is called an Fc-fusion protein.

Specific examples of the monomer protein include, for example, transglutaminases and the insulin-like growth factor 1 (IGF-1). Examples of transglutaminase gene include genes of secretory transglutaminases of actinomycetes such as *Streptoverticillium mobaraense* IFO 13819, *Streptoverticillium cinnamoneum* IFO 12852, *Streptoverticillium griseocarneum* IFO 12776, *Streptomyces lydicus* [WO9606931], filamentous fungi such as *Oomycetes* [WO96/22366], and so forth. In addition, specific examples of the monomer protein further include monomer proteins as the antibody-related molecules, for example, the heavy chain (H chain), the light chain (L chain), scFv, and sdFv.

Further, specific examples of the multimer protein include, for example, the vascular endothelial growth factor (VEGF), insulin, interleukin-5, interferon-γ, tumor necrosis factors (TNFs). In addition, specific examples of the multimer protein further include multimer proteins such as the antibody-related molecules, for example, complete antibodies, Fab, F(ab'), F(ab')$_2$, Fc, dimer consisting of the heavy chain (H chain) and the light chain (L chain), Fc-fusion proteins, sc(Fv)$_2$, and diabody. Among these, Fab, F(ab')$_2$, and Fc-fusion proteins.

The receptor protein is not particularly limited, and can be, for example, a receptor protein for any of the bioactive proteins and other bioactive substances. Examples of other bioactive substances include, for example, neurotransmitters such as dopamine. In addition, the receptor protein can also be an orphan receptor, of which ligand has not been identified.

The antigenic protein to be used as vaccine is not particularly limited so long as it is a protein which causes an immune response, and the antigenic protein can be appropriately chosen according to the intended target of the immune response.

Genes encoding the heterologous fusion proteins can be modified according to a host to be used and for obtaining a desired activity. For example, the genes encoding these proteins may be modified so that the proteins include substitution, deletion, insertion, and/or addition of one or several amino acid residues. The explanations concerning variants of the penicillin-binding proteins, the cell surface layer proteins or the inteins, or a combination of them, and the genes encoding them explained herein can also be applied mutatis mutandis to the heterologous fusion protein to be produced by secretory production by the method of the present invention and the gene encoding it. Further, in the genes encoding these proteins, any codon may be replaced with an equivalent codon thereof. For example, in the genes encoding these proteins, codons may be optimized as required according to codon frequencies observed in the host.

Genetic Construct

Although the genetic construct used for the present invention is not particularly limited so long as secretory production of the heterologous fusion protein is attained, it preferably contains a promoter sequence that functions in a coryneform bacterium, a nucleic acid sequence encoding a signal peptide that is ligated downstream from the promoter sequence and functions in the coryneform bacterium, and a nucleic acid sequence encoding the heterologous fusion protein that is ligated downstream from the nucleic acid sequence encoding the signal peptide. The nucleic acid sequence encoding a signal peptide may be ligated downstream from the promoter sequence so that the signal peptide is expressed under control by the promoter. The nucleic acid sequence encoding the heterologous fusion protein may be ligated downstream from the nucleic acid sequence encoding the signal peptide so that the heterologous protein is expressed as a fusion protein with the signal peptide. As the heterologous fusion protein includes extein and intein regions located at the N- and C-terminal parts of the protein, respectively, the nucleic acid sequence encoding the heterologous fusion protein encodes an extein and an intein in such a way that the nucleic acid sequence encoding the extein is ligated downstream from the sequence encoding the signal peptide and the nucleic acid sequence encoding the intein is ligated downstream from the sequence encoding the extein.

The genetic construct used for the present invention may also contain a control sequence (operator, terminator, etc.) effective for expression of the heterologous fusion protein gene in a coryneform bacterium at such an appropriate position that it can function. The genetic construct used for the present invention may also contain the nucleic acid sequence encoding a protein tag such as the affinity tag, the solubilization tag, the chromatography tag, the epitope tag, or the fluorescence tag. As to an affinity tag, the chitin binding protein (CBP), maltose binding protein (MBP), glutathione-S-transferase (GST), and the poly(His) tag can be used to purify the heterologous fusion protein from the crude medium using an affinity technique.

The promoter used in the present invention is not particularly limited so long as a promoter that functions in a coryneform bacterium is chosen, and it may be a promoter derived from a coryneform bacterium, or a heterogeneous promoter. The «promoter that functions in a coryneform bacterium» refers to a promoter that shows a promoter activity in a coryneform bacterium. Specific examples of the heterogeneous promoter include, for example, promoters derived from *E. coli* such as tac promoter, lac promoter, trp promoter, rplK promoter, gapA promoter, and araBAD promoter. Among these, potent promoters such as tac promoter, and inducible promoters such as araBAD promoter may be used.

Examples of the promoter derived from a coryneform bacterium include, for example, promoters of the cell surface layer proteins PS1, PS2 (also referred to as CspB), and SlpA (also referred to as CspA), and promoters of various amino acid biosynthesis system genes. Specific examples of the promoters of various amino acid biosynthesis system genes include, for example, promoters of the glutamate dehydrogenase gene of the glutamic acid biosynthesis system, the glutamine synthetase gene of the glutamine synthesis system, the aspartokinase gene of the lysine biosynthesis system, the homoserine dehydrogenase gene of the threonine biosynthesis system, the acetohydroxy acid synthetase gene of the isoleucine and valine biosynthesis system, 2-isopropylmalate synthetase gene of the leucine biosynthesis system, the glutamate kinase gene of the proline and arginine biosynthesis system, the phosphoribosyl-ATP pyrophosphorylase gene of the histidine biosynthesis system, the deoxyarabinoheptulosonate phosphate (DAHP) synthetase gene of the aromatic amino acid biosynthesis systems such as those of tryptophan, tyrosine, and phenylalanine, the phosphoribosyl pyrophosphate (PRPP) amidotransferase gene of the nucleic acid biosynthesis systems such as those of inosinic acid and guanylic acid, the inosinic acid dehydrogenase gene, and the guanylic acid synthetase gene.

As the promoter, a high activity type of an existing promoter may be obtained by using various reporter genes and used. For example, by making the −35 and −10 regions in a promoter region closer to a consensus sequence, activity of the promoter can be enhanced (International Patent Publication WO00/18935). Examples of method for evaluating strength of a promoter and strong promoters are described in the paper of Goldstein M. A. and Doi R. H. Prokaryotic promoters in biotechnology, *Biotechnol. Annu. Rev.*, 1995, 1:105-1285, and so forth. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

A nucleic acid sequence of the genetic construct used for the present invention can be optimized to express the genetic construct in a coryneform bacterium as a host microorganism. Expression of the genetic construct can optimized by substituting rare and/or low-usage codons for synonymous middle- or high-usage codons, where codon usage can be defined as the number of times (frequency) a codon is translated per unit time in the cell of an organism or an average codon frequency of the sequenced protein-coding reading frames of an organism (Zhang S. P. et al., *Gene*, 1991, 105(1):61-72). The codon usage per organism can be found in the Codon Usage Database, which is an extended web-version of the CUTG (Codon Usage Tabulated from GenBank) (www.kazusa.or.jp/codon; Nakamura Y. et al., Codon usage tabulated from the international DNA sequence databases: status for the year 2000, *Nucl. Acids Res.*, 2000, 28(1):292). The substitution of low-usage codons for synonymous high-usage codons can be preferable. The substituting rare and/or low-usage codons for synonymous middle- or high-usage codons may be combined with co-expression of the genes which encode rare tRNAs recognizing rare codons.

Signal Peptide

The signal peptide used in the present invention is not particularly limited so long as a signal peptide that functions in the coryneform bacterium is chosen, and it may be a signal peptide derived from the coryneform bacterium, or it may be a heterogeneous signal peptide. The «signal peptide that functions in the coryneform bacterium» refers to a peptide that, when it is ligated to the N-terminus of an objective protein, allows the coryneform bacterium to secrete the protein. The signal peptide is preferably a signal peptide of a secretory protein of the coryneform bacterium as the host, more preferably a signal peptide of a cell surface layer protein of the coryneform bacterium. Examples of the cell surface layer protein of coryneform bacteria include PS1 and PS2 (CspB) derived from *C. glutamicum* (Japanese Patent Laid-open (Kohyo) No. 6-502548), and SlpA (CspA) derived from *C. ammoniagenes* (*C. stationis*) (Japanese Patent Laid-open (Kokai) No. 10-108675). The amino acid sequence of the signal peptide of PS1 is shown in SEQ ID NO: 56, the amino acid sequence of the signal peptide of PS2 (CspB) is shown in SEQ ID NO: 57, and the amino acid sequence of the signal peptide of SlpA (CspA) is shown in SEQ ID NO: 58. Moreover, U.S. Pat. No. 4,965,197 describes that there are signal peptides for DNases derived from coryneform bacteria, and such signal peptides can also be used for the present invention.

Although signal peptides have a certain characteristic of sequence common over biological species, a signal peptide that exhibits a secretory function in a certain biological species does not necessarily exhibit a secretory function in another biological species. Therefore, when a heterogeneous signal peptide is used, a signal peptide that functions in the coryneform bacterium may be appropriately chosen. Whether a certain signal peptide functions in the coryneform bacterium can be confirmed by, for example, expressing the objective protein as a fusion protein with that signal peptide, and confirming whether the protein is secreted or not.

The signal peptide may have a part of N-terminus amino acid sequence of the secretory protein from which the signal peptide is derived. The signal sequence is generally cleaved by a signal peptidase, when the translation product is secreted out of the cell. In addition, as a gene encoding a signal peptide, although a naturally occurring gene may be used as it is, it may be modified so that it has the optimal codons according to codon frequencies in a host to be used.

Secretory Protein

It is known that a secretory protein is generally translated as a preprotein (also referred to as prepeptide) or preproprotein (also referred to as prepropeptide), and then becomes a mature protein through processing. Specifically, a secretory protein is generally translated as a preprotein or preproprotein, then a signal peptide as the pre-part is cleaved with a protease (generally called signal peptidase), and the secretory protein is thereby converted into a mature protein or proprotein. As for the proprotein, the pro-part thereof is further cleaved by a protease, and the proprotein thereby becomes a mature protein. Hence, in the method, it is preferable to use a signal peptide for the secretory production of a heterologous fusion protein. In the present invention, a preprotein and a preproprotein of a secretory protein may be collectively referred to as «secretory protein precursor». The «signal peptide» (also referred to as «signal sequence») refers to an amino acid sequence existing at the N-terminus of a secretory protein precursor, and usually does not exist in a natural mature protein. More specifically, the signal peptide is joined to the N-terminus of an extein through the peptide bond.

Penicillin-Binding Protein

In general, the penicillin-binding proteins (PBPs) refer to proteins that bind with β-lactam type antibiotics, of which enzymatic function is inhibited by binding with β-lactam type antibiotics. The penicillin-binding proteins include high molecular weight PBPs (HMW-PBPs) and low molecular weight PBPs (LMW-PBPs). The high molecular weight PBPs include class A high molecular weight PBPs (class A HMW-PBPs) and class B high molecular weight PBPs (class B HMW-PBPs). The class A HMW-PBPs has both a transpeptidase activity domain having the transpeptidase activity for crosslinking peptidoglycan moieties and a transglycosylase activity domain having the transglycosylase activity for forming a polysaccharide chain from disaccharides. The class B HMW-PBPs has a transpeptidase activity domain. For example, as for *C. glutamicum*, PBP1a and PBP1b can be mentioned as the class A HMW-PBPs. As for *C. glutamicum*, FtsI, PBP2a, and PBP2b can be mentioned as the class B HMW-PBPs.

A coryneform bacterium of the present invention can be modified so that activity of a protein that is a penicillin-binding protein has a property that if the activity thereof is reduced in a coryneform bacterium, amount of a heterologous fusion protein to be produced by secretory production is increased compared with that observed for a non-modified strain. As such a penicillin-binding protein, for example, one selected from PBP1a, PBP1b, class B HMW-PBPs, and LMW-PBPs, or one selected from PBP1a, PBP1b, and class B HMW-PBPs, or one selected from PBP1a and PBP1b can be used.

The «property that if activity of the protein is reduced in a coryneform bacterium, amount of a heterologous fusion protein to be produced by secretory production is increased compared with that observed for a non-modified strain» refers to a property that if activity of the protein is reduced in a coryneform bacterium, an ability to produce a heterologous fusion protein by secretory production in an amount larger than that observed for a non-modified strain such as wild-type strain or parent strain is imparted to the coryneform bacterium. Although degree of increase of amount of the heterologous fusion protein to be produced by secretory production is not particularly limited so long as the amount of the heterologous fusion protein produced by secretory production increases compared with that observed for a non-modified strain, to produce a heterologous fusion protein by secretory production in an amount larger than that observed for a non-modified strain may mean, for example, to produce the heterologous fusion protein by secretory production in an amount larger than that observed for a non-modified strain by 10% or more, 20% or more, 30% or more, or 100% or more, in terms of the accumulation amount in the medium and/or the cell surface layer. In addition, to produce a heterologous fusion protein by secretory production in an amount larger than that observed for a non-modified strain may mean that whereas the heterologous fusion protein cannot be detected when non-concentrated culture supernatant of a non-modified strain is applied to SDS-PAGE and stained with CBB, the heterologous fusion protein can be detected when non-concentrated culture supernatant of a modified strain is applied to SDS-PAGE and stained with CBB.

Also, the «property that if activity of the protein is reduced in a coryneform bacterium, amount of a heterologous fusion protein to be produced by secretory production is increased compared with that observed for a non-modified strain» regarding a penicillin-binding protein includes a property that if activity of the protein is reduced in a strain in which activity of a cell surface layer protein is not reduced, the ability of the strain to produce a heterologous fusion protein by secretory production is not increased, however, if activity of the protein is reduced in a strain in which activity of a cell surface layer protein is reduced, the ability of the strain to produce a heterologous fusion protein by secretory production is increased.

Whether a protein has a property that if activity of the protein is reduced in a coryneform bacterium, amount of a heterologous fusion protein to be produced by secretory production is increased compared with that observed for a non-modified strain can be confirmed by preparing a strain from a strain belonging to the coryneform bacteria by such modification that activity of the protein is reduced, quantifying amount of the heterologous fusion protein produced by secretory production observed when the modified strain is cultured in a medium, and comparing that amount with amount of the heterologous fusion protein produced by secretory production when the strain not modified (unmodified strain) is cultured in the medium.

The Cgl0278 gene encoding the PBP1a protein of the *C. glutamicum* ATCC 13032 corresponds to a sequence complementary to the sequence of the 294001 to 296388 positions in the genome sequence registered at the NCBI database as GenBank accession BA000036 (version BA000036.3 GI: 42602314). Also, the PBP1a protein of the *C. glutamicum* ATCC 13032 is registered as GenBank accession NP_599531 (version NP_599531.1 GI: 19551529, locus_tag=«NCgl0274»). The nucleotide sequence of the Cgl0278 gene of *C. glutamicum* ATCC 13032 and the amino acid sequence of the PBP1a protein encoded by this gene are shown in SEQ ID NOs: 43 and 44, respectively.

The Cgl2986 gene encoding the PBP1b protein of the *C. glutamicum* ATCC 13032 corresponds to a sequence complementary to the sequence of the 3160346 to 3162508 positions in the genome sequence registered at the NCBI database as GenBank accession BA000036 (VERSION BA000036.3 GI: 42602314). Also, the PBP1b protein of the *C. glutamicum* ATCC 13032 is registered as GenBank accession YP_227236 (version YP_227236.1 GI: 62391834, locus_tag=«cg3313»). The nucleotide sequence of the Cgl2986 gene of *C. glutamicum* ATCC 13032 and the amino acid sequence of the PBP1b protein encoded by this gene are shown in SEQ ID NOs: 45 and 46, respectively.

Since the gene encoding the penicillin-binding protein may differ depending on species or strain to which the coryneform bacterium belongs, the penicillin-binding protein may have one or more homologues or variant proteins. In such a case, the variant proteins encoded by the penicillin-binding protein gene may have a homology, defined as the parameter «identity» when using the computer program BLAST, of not less than 80%, not less than 90%, not less than 95%, or not less than 98% with respect to the entire amino acid sequence of the wild-type protein so long as the activity of the variant proteins is maintained, or the three-dimensional structure of the variant proteins is not significantly changed relative to the wild-type proteins. Therefore, the variant nucleotide sequences of the penicillin-binding protein may have a homology, defined as the parameter «identity» when using the computer program BLAST, of not less than 80%, not less than 90%, not less than 95%, not less than 96%, not less than 97%, not less than 98%, or not less than 99% with respect to the entire nucleotide sequences of the wild-type protein genes so long as the activity of the variant proteins encoded by the genes is maintained, or the three-dimensional structure of the variant proteins is not significantly changed relative to the wild-type proteins.

Cell Surface Layer Protein

The cell surface layer proteins are proteins constituting the cell surface layers (S-layer) of bacteria and archaea. Examples of the cell surface layer proteins of coryneform bacteria include PS1 and PS2 (also referred to as CspB) of *C. glutamicum* and SlpA (also referred to as CspA) of *C. stationis*. Among them, it is preferred that the activity of PS2 protein is reduced.

The nucleotide sequence of the cspB gene of *C. glutamicum* ATCC 13869 and the amino acid sequence of the PS2 protein encoded by this gene are shown in SEQ ID NOs: 59 and 57, respectively.

Also, for example, amino acid sequences of CspB homologues regarding 28 strains of *C. glutamicum* have been reported (Hansmeier N. et al., Classification of hyper-variable *Corynebacterium glutamicum* surface-layer proteins by sequence analyses and atomic force microscopy, *J. Biotechnol.*, 2004, 112:177-193). These 28 strains of *C. glutamicum* and the GenBank accession numbers of the cspB gene homologues in NCBI database are exemplified hereafter (the GenBank accession numbers are shown in the parentheses).

*C. glutamicum* ATCC13058 (AY524990)
*C. glutamicum* ATCC13744 (AY524991)
*C. glutamicum* ATCC13745 (AY524992)
*C. glutamicum* ATCC14017 (AY524993)
*C. glutamicum* ATCC14020 (AY525009)
*C. glutamicum* ATCC14067 (AY524994)
*C. glutamicum* ATCC14068 (AY525010)
*C. glutamicum* ATCC14747 (AY525011)
*C. glutamicum* ATCC14751 (AY524995)
*C. glutamicum* ATCC14752 (AY524996)
*C. glutamicum* ATCC14915 (AY524997)
*C. glutamicum* ATCC15243 (AY524998)
*C. glutamicum* ATCC15354 (AY524999)

C. glutamicum ATCC17965 (AY525000)
C. glutamicum ATCC17966 (AY525001)
C. glutamicum ATCC19223 (AY525002)
C. glutamicum ATCC19240 (AY525012)
C. glutamicum ATCC21341 (AY525003)
C. glutamicum ATCC21645 (AY525004)
C. glutamicum ATCC31808 (AY525013)
C. glutamicum ATCC31830 (AY525007)
C. glutamicum ATCC31832 (AY525008)
C. glutamicum LP-6 (AY525014)
C. glutamicum DSM20137 (AY525015)
C. glutamicum DSM20598 (AY525016)
C. glutamicum DSM46307 (AY525017)
C. glutamicum 22220 (AY525005)
C. glutamicum 22243 (AY525006)

Since the nucleotide sequence of a gene encoding a cell surface layer protein may differ depending on the species or strain to which the coryneform bacterium belongs, the gene encoding a cell surface layer protein may be a variant of the aforementioned nucleotide sequence so long as the gene encodes a protein having a property that if activity of the protein is reduced in a coryneform bacterium, amount of a heterologous fusion protein to be produced by secretory production is increased compared with that observed for a non-modified strain. For example, the gene encoding a cell surface layer protein may be a gene encoding a protein having the aforementioned amino acid sequence including substitution, deletion, insertion, or addition of one or several amino acid residues at one or several positions so long as the gene encodes a protein having a property that if activity of the protein is reduced in a coryneform bacterium, amount of a heterologous fusion protein to be produced by secretory production is increased compared with that observed for a non-modified strain. The aforementioned explanations concerning variants of a penicillin-binding protein and a gene encoding it can also be applied mutatis mutandis to variant proteins of a cell surface layer protein and a gene encoding it.

Also, the «property that if activity of the protein is reduced in a coryneform bacterium, amount of a heterologous fusion protein to be produced by secretory production is increased compared with that observed for a non-modified strain» regarding a cell surface layer protein includes a property that if activity of the protein is reduced in a strain in which activity of a penicillin-binding protein is not reduced, the ability of the strain to produce a heterologous fusion protein by secretory production is not increased, however, if activity of the protein is reduced in a strain in which activity of a penicillin-binding protein is reduced, the ability of the strain to produce a heterologous fusion protein by secretory production is increased.

In the present invention, the expression «activity of a cell surface layer protein is reduced» includes a case where a coryneform bacterium has been modified so that activity of a cell surface layer protein is reduced and a case where activity of a cell surface layer protein has been intrinsically reduced in a coryneform bacterium. The «case where activity of a cell surface layer protein has been intrinsically reduced in a coryneform bacterium» includes a case where a coryneform bacterium is intrinsically deficient in a cell surface layer protein. That is, examples of a coryneform bacterium in which activity of a cell surface layer protein is reduced include a coryneform bacterium which intrinsically deficient in a cell surface layer protein. Examples of the «case where a coryneform bacterium is intrinsically deficient in a cell surface layer protein» include a case where a coryneform bacterium is intrinsically deficient in a gene encoding a cell surface layer protein. The expression «a coryneform bacterium is intrinsically deficient in a cell surface layer protein» can mean that a coryneform bacterium is intrinsically deficient in one or more proteins selected from cell surface layer protein(s) found in other strain(s) of the species to which the coryneform bacterium belongs. For example, «C. glutamicum is intrinsically deficient in a cell surface layer protein» can mean that a C. glutamicum strain is intrinsically deficient in one or more proteins selected from cell surface layer protein(s) found in other C. glutamicum strain(s), i.e. for example, deficient in PS1 and/or PS2 (CspB). Examples of the coryneform bacterium which intrinsically deficient in a cell surface layer protein include C. glutamicum ATCC13032, which is intrinsically deficient in the cspB gene.

Means for Reducing Activity of a Protein

The phrase «activity of a protein is reduced» can mean that activity of the protein is decreased compared with that of a non-modified strain such as a wild-type strain or a parent strain, which includes a case where the activity completely disappears. Specifically, the phrase «activity of a protein is reduced» can mean that number of molecules of the protein per cell is reduced, and/or function of each molecule of the protein is reduced compared with those of a non-modified strain. That is, the phrase «activity» regarding the phrase «activity of a protein is reduced» can refer to the transcription amount (the amount of mRNA) of a gene encoding the protein or the amount of the protein, as well as the catalytic activity of the protein. In addition, the case where «number of molecules of the protein per cell is reduced» includes a case where the protein does not exist at all. Further, the case where «function of each molecule of the protein is reduced» includes a case where function of each molecule of the protein completely disappears.

The modification for reducing activity of a protein can be attained by, for example, reducing expression of a gene encoding the protein. «Reduction of gene expression» is also referred to as «attenuation of gene expression». The reduction of gene expression may be induced by, for example, reduction of transcription efficiency, reduction of translation efficiency, or a combination of them. Reduction of expression of a gene can be attained by modifying an expression control sequence of the gene such as a promoter, an enhancer, an attenuator, a ribosome-binding site, etc. When an expression control sequence is modified, preferably one nucleotide or more, more preferably two nucleotides or more, particularly preferably three nucleotides or more, of the expression control sequence are modified. Moreover, a part or the entire expression control sequence may be deleted. Reduction of gene expression can also be attained by, for example, manipulating a factor responsible for expression control. Examples of the factor responsible for expression control include low molecules responsible for transcription or translation control (inducers, inhibitors, etc.), proteins responsible for transcription or translation control (transcription factors etc.), and so forth.

The modification for reducing activity of a protein can also be attained by, for example, disrupting the gene encoding the protein. Disruption of a gene can be attained by, for example, deleting a part or the entire coding region of the gene on a chromosome. Furthermore, the total gene including sequences upstream and downstream from the gene on a chromosome may be deleted. The region to be deleted may be any region such as a 3'-end region, an internal region, or a 5'-end region, so long as reduction of the activity of the protein is to be attained. Deletion of a longer region can usually more surely inactivate the gene. Further, it is preferred that reading frames of the sequences upstream and downstream from the region to be deleted are not the same.

Disruption of a gene can also be attained by, for example, introduction of a mutation for an amino acid substitution (missense mutation), a stop codon (nonsense mutation), a frame shift mutation which adds or deletes one or two nucleotides into the coding region of the gene on a chromosome, or the like (Qiu Z. and Goodman M. F., *J. Biol. Chem.,* 1997, 272:8611-8617; Kwon D. H. et al., *J. Antimicrob. Chemother.,* 2000, 46:793-796; Yano T. et al., *Proc. Natl. Acad. Sci. USA,* 1998, 95:5511-5515).

Disruption of a gene can also be attained by, for example, inserting another sequence into the coding region of the gene on a chromosome. The site of the insertion may be any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates activity of the encoded protein is chosen, and examples include, for example, a marker gene such as antibiotic resistance genes, a gene useful for production of a heterologous protein, a transcription termination signal, and so forth.

Such modification of a gene on a chromosome as described above can be attained by, for example, preparing a deficient type gene in which a partial sequence of the gene is deleted so that it cannot produce a protein that can normally function, and transforming a bacterium with a recombinant DNA containing the deficient type gene to cause homologous recombination between the deficient type gene and the gene on a chromosome and thereby substitute the deficient type gene for the gene on the chromosome. In such a case, if a marker gene selected according to characteristics of the host such as auxotrophy is included in the recombinant DNA, the operation becomes easy. The protein encoded by the deficient type gene has a conformation different from that of a wild-type protein, even if it is produced, and thus the function thereof is reduced or eliminated. Such gene disruption based on gene substitution utilizing homologous recombination has already been and includes a method called «Red driven integration» (Datsenko, K. A, and Wanner, B. L., *Proc. Natl. Acad. Sci. USA,* 2000, 97:6640-6645), a method of using a linear DNA such as a method utilizing the Red driven integration in combination with an excision system derived from λ phage (referred to as «Red/ET-driven integration» or «Red/ET-mediated integration) (Cho, E. H., Gumport, R. I., Gardner, J. F., *J. Bacteriol.,* 2002, 184:5200-5203), a method of using a plasmid containing a temperature sensitive replication origin, a method of using a plasmid capable of conjugative transfer, a method of using a suicide vector not having replication origin which functions in a host (U.S. Pat. No. 6,303,383, Japanese Patent Laid-open (Kokai) No. 05-007491), and so forth.

The modification for reducing activity of a protein can also be attained by, for example, a mutagenesis treatment. Examples of the mutagenesis treatment include usual mutagenesis treatments such as irradiation of X-ray or ultraviolet (UV) radiation and mutagenesis treatment with a mutation agent such as N-methyl-N'-nitro-N-nitrosoguanidine (MNNG), ethyl methanesulfonate (EMS), and methyl methanesulfonate (MMS).

Reduction of activity of a protein can be confirmed by measuring activity of the protein. In the case of a penicillin-binding protein, whether activity of the protein has been reduced can be confirmed by, for example, measuring the transpeptidase activity and/or the transglycosylase activity depending on the class to which the protein belongs. The transpeptidase activity and/or the transglycosylase activity can be measured by, for example, a method well known to those skilled in the art. Specifically, for example, the transpeptidase and transglycosylase activities of PBP1a can be measured by measuring the reaction of oligomerizing lipid II to glycan strands and forming peptide cross-links (Born P., et al., *J. Biol. Chem.,* 2006, 281(37):26985-26993). Specifically, activity of a protein is preferably decreased to, for example, 50% or less, 20% or less, 10% or less, 5% or less, or 0%, of that observed in a non-modified strain.

Reduction of expression of a gene can be confirmed by confirming reduction of transcription amount of the gene or reduction of amount of the protein expressed from the gene. Reduction of transcription amount of a gene can be confirmed by comparing amount of mRNA transcribed from the gene with that observed in a non-modified strain. Examples of the method for measuring amount of mRNA include Northern hybridization, quantitative reverse transcription polymerase chain reaction (RT-PCR), and so forth (Molecular Cloning, Cold spring Harbor Laboratory Press, Cold Spring Harbor (USA), 2001). The amount of mRNA is preferably decreased to, for example, 50% or less, 20% or less, 10% or less, 5% or less, or 0%, of that observed in a non-modified strain.

Decrease in amount of a protein can be confirmed by Western blotting using antibodies that bind to the protein (Molecular Cloning, Cold Spring Harbor Laboratory Press, Cold Spring Harbor (USA), 2001). The amount of the protein is preferably decreased to, for example, 50% or less, 20% or less, 10% or less, 5% or less, or 0%, of that observed in a non-modified strain.

Disruption of a gene can be confirmed by determining nucleotide sequence or restriction enzyme map of a part of the gene or a full length of the gene, or the like depending on the means used for the disruption. Presence or absence of the gene can be measured by, for example, restricting the chromosomal DNA followed by Southern blotting using a probe based on the gene sequence, fluorescence in situ hybridization (FISH), and the like.

The methods mentioned above for reducing activity of a protein can also be applied mutatis mutandis to arbitrary proteins and genes encoding them as well as for reducing activity of a penicillin-binding protein and reducing activity of a cell surface layer protein.

Means for Introducing the Genetic Construct

The method for introducing the genetic construct used for the present invention into the coryneform bacterium is not particularly limited. In the bacterium, the genetic construct may be present on a vector that autonomously replicates out of the chromosome such as a plasmid, or may be incorporated into the chromosome. In addition, as described above, for constructing the bacterium, modifications such as introduction of the genetic construct, impartation or enhancement of ability to produce a protein by secretory production, reduction of activity of a penicillin-binding protein, and reduction of activity of a cell surface layer protein can be performed in an arbitrary order.

The chosen genetic construct can be introduced into a host by using, for example, a vector containing the genetic construct. The vector is not particularly limited so long as a vector autonomously replicable in the coryneform bacterium is chosen, and may be, for example, a vector derived from a bacterial plasmid, a vector derived from a yeast plasmid, a vector derived from a bacteriophage, cosmid, phagemid, or the like. As the vector, for example, a plasmid derived from a coryneform bacterium is preferred. Specific examples of vector autonomously replicable in coryneform bacteria include pHM1519 (Miwa K. et al., *Agric. Biol. Chem.*, 1984, 48(11):2901-2903); pAM330 (Miwa K. et al., *Agric. Biol. Chem.*, 1984, 48(11):2901-2903); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVC7 described in Japanese Patent Laid-open (Kokai) No. 9-070291; and so forth.

Further, an artificial transposon and so forth can also be used. When a transposon is used, a heterologous protein gene is introduced into a chromosome by homologous recombination or translocation ability of the transposon itself. Other examples of the introduction method utilizing homologous recombination include, for example, the methods utilizing a linear DNA, a plasmid having a temperature sensitive replication origin, a plasmid capable of conjugative transfer, a suicide vector not having a replication origin which functions in a host, and so forth. In addition, when a heterologous protein gene is introduced into a chromosome, so long as the genetic construct is constituted on the chromosome, either one or both of a promoter sequence and a nucleic acid sequence encoding the signal peptide contained in the genetic construct may be one or those originally existing in the host chromosome. Specifically, for example, by using a promoter sequence and a nucleic acid sequence encoding the signal peptide ligated downstream from the promoter sequence originally existing in the host chromosome as they are, and replacing only the gene ligated downstream from the nucleic acid sequence encoding the signal peptide with the objective heterologous protein gene, the genetic construct is also constituted on the chromosome, and the bacterium an be thereby constructed.

Also, in the case where two or more kinds of proteins are expressed, genetic constructs for secretory expression of the proteins may be harbored by the bacterium so that secretory expression of the heterologous fusion protein(s) can be attained. Specifically, for example, all of the genetic constructs for secretory expression of the proteins may be harbored on a single vector, or may be harbored on a chromosome. Further, the genetic constructs for secretory expression of the proteins may be harbored separately on a plurality of vectors, or may be harbored separately on a single or a plurality of vectors and a chromosome. The «case where two or more kinds of proteins are expressed» includes, for example, the case where two or more kinds of heterologous fusion proteins are produced by secretory production, or the case where a hetero-multimer protein is produced by secretory production.

The method for introducing the genetic construct into the coryneform bacterium is not particularly limited, and a generally used method, for example, the protoplast method (Miwa K. et al., *Gene*, 1985, 39:281-286), the electroporation method (Dunican L. K. and Shivnan E., *Nat. Biotechnol.*, 1989, 7:1067-1070), and so forth can be used.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the person skilled in the art. These methods are described, for example, in Sambrook J., Fritsch E. F. and Maniatis T., «Molecular Cloning: A Laboratory Manual», $2^{nd}$ ed., Cold Spring Harbor Laboratory Press, Cold Spring Harbor (USA), 1989; Green M. R. and Sambrook J. R., «Molecular Cloning: A Laboratory Manual», $4^{th}$ ed., Cold Spring Harbor Laboratory Press, Cold Spring Harbor (USA), 2012); Glick B. R., Pasternak J. J. and Cheryl L. P., «Molecular Biotechnology: principles and applications of recombinant DNA», $4^{th}$ ed., ASM Press, Washington, D.C. (USA), 2009).

2. Method for Producing Heterologous Fusion Protein

The present invention provides a method for producing a heterologous fusion protein by steps including culturing the bacterium and collecting the heterologous fusion protein produced by secretory production (henceforth also referred to as the «method of the present invention» or the «method for producing a heterologous fusion protein of the present invention»).

The bacterium can be cultured according to usually used method and conditions. For example, the bacterium can be cultured in a usual medium containing a carbon source, a nitrogen source, and inorganic ions. In order to obtain still higher proliferation, organic micronutrients such as vitamins and amino acids can also be added as required.

As the carbon source, carbohydrates such as glucose and sucrose, organic acids such as acetic acid, alcohols, and others can be used. As the nitrogen source, ammonia gas, aqueous ammonia, ammonium salts, and others can be used. As the inorganic ions, calcium ions, magnesium ions, phosphate ions, potassium ions, iron ions, and so forth are appropriately used as required. The culture is performed within appropriate ranges of pH 5.0 to 8.5 and 15 to 37° C. for 1 to 7 days under aerobic conditions. Further, the culture conditions for L-amino acid production by coryneform bacteria and other conditions described in the methods for producing a protein using a signal peptide of the Sec type or the Tat type can be used (refer to WO01/23591 and WO2005/103278). Further, when an inducible promoter is used for expression of the heterologous fusion protein, culture may also be performed with adding a promoter-inducing agent to the medium. By culturing the bacterium under such conditions, a large amount of the objective protein is produced in cells and efficiently secreted out of the cells. In addition, according to the method of the present invention, the produced heterologous fusion protein is secreted out of the cells, and therefore a protein that may be lethal if it is accumulated in a large amount in cells of microorganisms, such as transglutaminases, can also be continuously produced without lethal effect.

The heterologous fusion protein secreted in the medium according to the method of the present invention can be separated and purified from the medium after the culture by a method well known to those skilled in the art. For example, after the cells are removed by centrifugation or the like, the protein can be separated and purified by a known appropriate method such as salting out, ethanol precipitation, ultrafiltration, gel filtration chromatography, ion exchange column chromatography, affinity chromatography, medium or high pressure liquid chromatography, reverse phase chromatography, and hydrophobic chromatography, or a combination of these. Further, in a certain case, culture or culture supernatant may be used as it is. The protein secreted in the cell surface layer according to the method of the present invention can also be separated and purified in the same manner as that for the case where the protein is secreted in the medium, after solubilizing it by a method well known to those skilled in the art such as elevation of salt concentration and use of a surfactant. Further, in a certain case, the protein secreted in the cell surface layer may be used as, for example, as immobilized enzyme, without solubilizing it.

Secretory production of the objective heterologous fusion protein can be confirmed by performing SDS-PAGE for the culture supernatant and/or a fraction containing the cell surface layer as a sample thereby confirming the molecular weight of the separated protein bands. In addition, secretory production of the objective heterologous fusion protein can be confirmed by performing Western blotting using antibodies for the culture supernatant and/or a fraction containing the cell surface layer as a sample (Molecular Cloning, Cold spring Harbor Laboratory Press, Cold Spring Harbor (USA), 2001). Further, secretory production of the objective heterologous protein can be confirmed by determination of N-terminus amino acid sequence using protein sequencer. Furthermore, secretory production of the objective heterologous fusion protein can be confirmed by measuring its mass using mass spectrometer. Also, when the objective heterologous fusion protein is an enzyme or a protein having some kind of bioactivity that can be measured, secretory production of the objective heterologous fusion protein can be confirmed by measuring enzyme activity or bioactivity of the protein in the culture supernatant and/or a fraction containing the cell surface layer as a sample.

So long as the heterologous fusion protein is produced by secretory production using a coryneform bacterium, the activity of acyl rearrangement of an intein can be confirmed by using known techniques. For example, the activity can be confirmed by determining a product of the acyl rearrangement such as an intein or a molecule consisting of an extein and a reactant residue linked to the C-terminus of the extein. The product of acyl rearrangement can be determined using any conventional method which can distinguish between the heterologous fusion protein produced by secretory production and the products of acyl rearrangement. For example, spectrophotometric methods such as infrared spectroscopy can be used to determine formation of a new chemical bond in between an extein and a reactant residue linked to the C-terminus of the extein. Other methods of the spectrophotometric analysis of organic compounds are known to the person skilled in the art. Also, a chemical modification can be used to determine a product of acyl rearrangement. For example, a treatment of the heterologous fusion protein produced by secretory production, which is active in the acyl rearrangement, in the culture supernatant or a medium with a reactant having a nucleophilic group results in transesterification reaction to occur. Amines, thiols, alcohols, and so forth can be used to attain acyl rearrangement. For example, an extein can be carboxy amidated by reacting a heterologous fusion protein with hydroxylamine or ammonium bicarbonate as described in Cottingham I. R. et al., A method for the amidation of recombinant peptides expressed as intein fusion proteins in *Escherichia coli*, *Nat. Biotechnol.*, 2001, 19:974-977; Xu M.-Q. and Perler F. B. The mechanism of protein splicing and its modulation by mutation, *EMBO J.*, 1996, 15(19):5146-5153. In another example, a cleavage of the thioester bond in between an extein and intein can be induced using a thioesterification reaction by reacting a heterologous fusion protein with chemical compounds containing nucleophilic thiol (—SH) group such as dithiothreitol (DTT) (Chong S. et al., Utilizing the C-terminal cleavage activity of a protein splicing element to purify recombinant proteins in a single chromatographic step, *Nucleic Acids Res.*, 1998, 26(22): 5109-5115). Furthermore, a cleavage of the thioester bond in between an extein and intein can be induced by reacting a heterologous fusion protein with other chemical compounds containing nucleophilic thiol (—SH) group such as thiophenol or 2-mercaptoethanesulfonic acid (MES) or a salt thereof such as sodium salt MESNa) to obtain extein thioesters. Thus obtained extein thioesters can be modified by a chemical protein ligation (Muir T. W. et al., Expressed protein ligation: A general method for protein engineering, *Proc. Natl. Acad. Sci. USA*, 1998, 95:6705-6710; Evans T. C. Jr. et al., The in vitro ligation of bacterially expressed proteins using an intein from *Methanobacterium thermoautotrophicum*, *J. Biol. Chem.*, 1999, 274(7):3923-3926). Cysteine or cysteine derivatives can also be chemical compounds containing nucleophilic thiol group, which can be used to obtain a ligation product of extein and cysteine or cysteine derivatives (Kurpiers T. and Mootz H. D., Site-specific chemical modification of proteins with a prelabelled cysteine tag using the artificially split Mxe GyrA intein, *Chem. Bio. Chem.*, 2008, 9:2317-2325). The products of the nucleophilic acyl substitution reaction can be determined by any conventional method such as, for example, mass-spectroscopy, ultraviolet/visible spectroscopy, and so forth. The acyl rearrangement results in intein removal and, hence, the decrease of a molecular weight and a change of charge of the heterologous fusion protein produced by secretory production. Therefore, the products of acyl rearrangement such as an intein and a molecule consisting of an extein and a reactant residue linked to the C-terminus of the extein can be determined by protein gel electrophoresis (Simpson R. J., Electrophoresis of peptides (Tricine-SDS-PAGE), 2006, *CSH Protoc.*).

Method for Producing Modified Protein

The present invention also provides a method for producing a modified protein using the heterologous fusion protein. The modified protein produced by the method of this aspect may be a protein ligated to a substance, or a protein amidated at the C-terminus. The term "protein" refers to a concept of protein including those called peptide such as oligopeptide or polypeptide. Examples of the substance include toxin, drug, fluorophore, chromophore dye, polyethylene glycols (PEG), radioisotope-labeled compounds, a second polypeptide, and magnetic particles.

The present invention provides a method for producing a protein ligated to a substance, by steps including producing the heterologous fusion protein of the present invention produced by the method of the present invention for producing a heterologous fusion protein; and reacting the heterologous fusion protein with a reactant, wherein the reactant includes the substance or the method further includes modifying the reactant with the substance.

As described with respect to the method for producing a heterologous fusion protein of the present invention, the heterologous fusion protein can be cleaved and the extein can be ligated to a reactant by using the activity of acyl rearrangement of an intein upon reacting the heterologous fusion protein of the present invention with the reactant. The heterologous fusion protein can comprise a thioester bond or an ester bond in between the extein and the intein, which bond is obtained after the first stage of the acyl rearrangement as a result of, respectively, N—S shift or N—O shift as explained above. The obtained thioester or ester bond can be cleaved by reacting the heterologous fusion protein with a reactant containing a nucleophilic group such as, for example, amino group, thiol group or hydroxyl group, such that the reactant can ligate to the C-terminus of the extein comprising thioester or ester bond to produce a ligated reactant. As a result, a protein ligated to the reactant through the amide, thioester or ester bond is produced. Reactants containing amino, thiol and hydroxyl groups are exemplified above.

Specifically, the thioester bond in between the extein and the intein, which is obtained after the first stage of the acyl rearrangement as a result of N—S shift, can be cleaved by reacting the heterologous fusion protein with a thiol group-containing reactant such as, for example, dithiothreitol (DTT), thiophenol or 2-mercaptoethanesulfonic acid (MES) or a salt thereof such as sodium salt (MESNa), such that the reactant can ligate to the C-terminus of the extein comprising the thioester bond to produce a ligated reactant. As a result, a protein ligated to the reactant through the thioester bond is produced.

The ligating of a reactant to the C-terminus of extein of a heterologous fusion protein can be performed by the further ordinary methods. For example, when an extein thioester is obtained as a result of the first stage of the acyl rearrangement, thus obtained extein thioester can be modified by a chemical protein ligation (Muir T. W. et al., 1998; Evans T. C. Jr. et al., 1999). Cysteine or cysteine derivatives can also be the chemical compounds containing nucleophilic thiol group, which can be used to produce a ligation product of extein and cysteine or cysteine derivatives (Kurpiers T. and Mootz H. D., 2008). Polypeptides containing cysteine residue at its N-terminus can be also ligated to thus obtain extein thioester.

Two or more reactants may be used in combination. When plural reactants are used, at least one reactant can include the substance or be modified with the substance. An additional reactant may be one which accelerates the reaction of the heterologous fusion protein with a reactant which includes the substance or which is to be modified with the substance. Examples of the additional reactant include dithiothreitol and 2-mercaptoethanesulfonic acid.

The protein, which is ligated to reactant and produced by the method of the present invention, can be modified further. For example, a reactant may also contain one or more reactive groups, so that the reactive groups can react with other molecules. In one non-limiting example, a reactant may contain thiol group and azide group such as, for example, Cys-$CH_2CH_2CH_2N_3$. In such case, the thiol group of cysteine can react with the C-terminus of the extein, and the azide group ($N_3$) can react further with another compound such as, for example, toxin, drug, fluorophore or chromophore dye, and so forth. Thus the reactant can be modified with the substance.

The reactant may have or be modified to have a group which can be used for the ligation. Examples of the ligated substance include toxins, drugs, polyethylene glycols (PEG), radioisotope-labeled compounds, a second polypeptide, and magnetic particles. When the extein comprises the target protein which can be biologically recognized by a cell or tissue, the protein ligated to the substance can be used for targeting. Examples of such the target protein include an antibody, an antigen-binding fragment thereof, and receptor ligands such as hormones. The ligated substance can be delivered to the targeted cell or tissue depending on the kind of the target protein.

Yet specifically, as described with respect to the method for producing a heterologous fusion protein of the present invention, extein of the heterologous fusion protein can be amidated at its C-terminus by reacting the heterologous fusion protein with ammonia to obtain amidated peptides or proteins (Cottingham I. R. et al., A method for the amidation of recombinant peptides expressed as intein fusion proteins in *Escherichia coli*, *Nat. Biotech.*, 2001, 19:974-977).

The present invention also provide a method for producing a protein which is amidated at the C-terminus, by steps including producing a heterologous fusion protein by the method for producing the heterologous fusion protein of the present invention, and reacting the heterologous fusion protein with ammonia or a salt thereof.

Examples of the salt of ammonia includes $(NH_4)_2CO_3$, $NH_4Cl$, and $(NH_4)_2SO_4$. The heterologous fusion protein may be reacted with ammonia or the salt thereof in the presence of a compound containing a nucleophilic thiol group.

EXAMPLES

The present invention will be more precisely explained hereafter with reference to the following non-limiting Examples.

Example 1

Exenatide: Experimental Part 1.1«Design and Chemical Synthesis of EXC1 and MAG DNA-Fragments The chemical synthesis of the EXC1 DNA-fragment (SEQ ID NO: 1) and MAG DNA-fragment (SEQ ID NO: 2) were ordered from ATG Service Gene (Russian Federation, St.-Petersburg, www.service-gene.spb.ru). The EXC1 DNA-fragment encodes a regulatory part and a structural part, which corresponds to the first 37 amino acid residues of the cgr_2373 gene (NCBI Reference Sequence: NC_009342.1; gene ID 4992619; locus_tag=«cgR_2373»; nucleotides position from 2608342 to 2609838, complement) from *Corynebacterium glutamicum* R (NCBI Reference Sequence: NC_009342.1; GI: 145294042). Also, the ECX1 encodes a multi-cloning site KasI-NotI and a terminator of the nusG gene from *Corynebacterium glutamicum* R. The sequence of the EXC1 DNA-fragment was designed to remove NdeI site within regulatory part of cgr_2373 by the T305G substitution and introduce NdeI site just before the ATG start codon by the TCT588-590CAT substitution. The structure of the EXC1 DNA-fragment is shown on FIG. 1.

Figure 2:
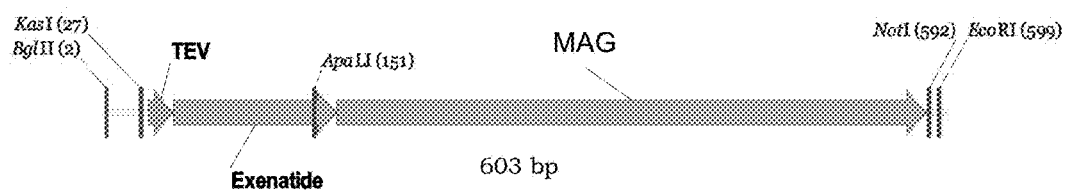
FIG. 2 shows the structure of the MAG DNA-fragment.

The MAG DNA-fragment encodes an artificial open reading frame (ORF) having a TEV protease cleavage site, exenatide (NCBI Pub Chem, compound ID (CID): 56927919; SEQ ID NO: 34), and the intein Mmag Magn8951 BIL from *Magnetospirillum magnetotacticum* MS-1 (Amitai G. et al., Mol. Microbiol., 2003, 47(1):61-73; MAG; tools.neb.com/inbase/intein.php?name=Mmag+Magn8951+BIL; SEQ ID NO: 37). The original sequence of the MAG encoding region was modified to delete BamHI site by the TTG389-391CTC substitution; the last triplet encoding asparagine (N) was deleted. The structure of the MAG DNA-fragment is shown on FIG. 2.

The EXC1 and MAG DNA-fragments were cloned into pUC57 cloning vector (GenBank: Y14837.1; GI: 2440162) into EcoRV site. Thus the pUC57-EXC1 and pUC57-MAG plasmids were constructed (ATG Service Gene).

1.2. Construction of pEXC1 Plasmid

The EXC1 DNA-fragment was excised from pUC57-EXC1 plasmid using KpnI and BamHI, purified by electrophoresis in agarose gel, and ligated with pPK4/KpnI-BamHI vector. Thus the pEXC1 plasmid was obtained. The pPK4 plasmid was described in U.S. Pat. No. 6,090,597 A.

1.3. Construction of pEXC1-Exe-MAG Plasmid

The MAG DNA-fragment was excised from pUC57-MAG plasmid using KasI and NotI, purified by electrophoresis in agarose gel, and ligated with pEXC1/KasI-NotI vector. Thus the pEXC1-exe-MAG plasmid was obtained.

1.4. Construction of the pEXC1-Exe-MAG-HT#2

Figure 3:
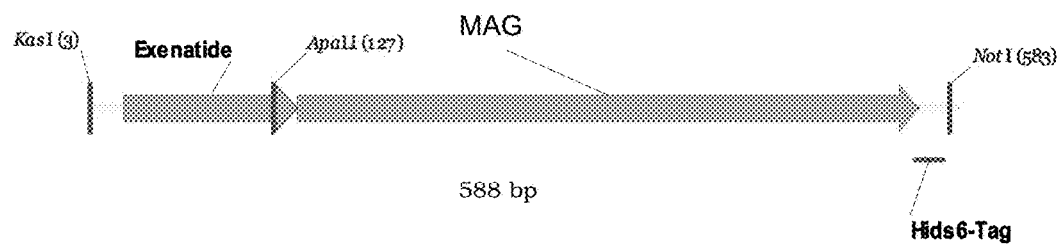
FIG. 3 shows the structure of the KasI-MAG-HT-NotI DNA-fragment.

The MAG-HT DNA-fragment (903 bp, FIG. 3) was PCR-amplified using primers P1 (SEQ ID NO: 3), P2 (SEQ ID NO: 4), and plasmid pEXC1-exe-MAG as the template. The PCR protocol was as follows: (95° C., 10"/52° C., 15"/72° C., 140"; 25 cycles). The KasI-MAG-HT-NotI DNA-fragment harbors an artificial ORF having genes encoding the exenatide (exe), intein (MAG), and His6-tag (HT) (FIG. 3). The primer P1 is flunked by NotI site and the His6-tag locus. Therefore, the MAG-HT DNA-fragment contained the C-terminus-His6-tagged exenatide-MAG fused gene flunked by KasI and NotI sites. The MAG-HT DNA-fragment was digested with KasI and NotI, purified by electrophoresis in agarose gel, and ligated with pEXC1/KasI-NotI vector. Obtained ligation mixture was introduced into JM109 bacterial strain (Catalog No. P9751) using standard calcium chloride transformation procedure (Mandel M. and Higa A., Calcium-dependent bacteriophage DNA infection, *J. Mol. Biol.*, 1970, 53:159-162). Thus, about 500 kanamycin-resistant ($Kn^R$) colonies were obtained. Restriction analysis of plasmids isolated from twelve arbitrary chosen clones revealed eight plasmids with desired structure. Sequencing analysis of selected plasmids revealed seven plasmids with desired sequence. One plasmid pEXC1-exe-MAG-HT with desired structure, conditionally referred to as pEXC1-exe-MAG-HT#2, was used in subsequent experiments.

1.5. Cultivation of *C. glutamicum* Plasmid Strains

All strains and plasmids used are described in Table 1. Electroporation of *C. glutamicum* strains was performed according to the method described in Bonnassie S. et al., *Transfer of plasmid DNA to Brevibacterium lactofermentum by electrotransformation*, *J. Gen. Microbiol.*, 1990, 136: 2107-2112). Routine cultivation of *C. glutamicum* plasmid strains was performed in 2YT broth or 2YT-agar media (Sambrook J., Fritsch E. F. and Maniatis T., «Molecular Cloning: A Laboratory Manual», $2^{nd}$ ed., Cold Spring Harbor Laboratory Press, Cold Spring Harbor (USA), 1989) supplemented with kanamycin (25-50 μg/mL) or chloramphenicol (4-8 μg/mL).

The *C. glutamicum* YDK010 (WO2004/029254) strain was used as a host strain for production of the heterologous fusion proteins. The YDK010 strain is a cell surface protein PS2 deficient strain of the *C. glutamicum* AJ12036 strain (FERM BP-734). The modified YDK010 strain was cultivated in a MM-medium. The MM-medium was prepared from the components A, B, and C:

Component A:

| Glucose | 60 g/L |
|---|---|
| $MgSO_4 \cdot 7H_2O$ | 1 g/L |
| $FeSO_4 \cdot 7H_2O$ | 0.01 g/L (add 1 mL/L-medium using 10 g/L stock solution in 0.1M HCl) |
| $MnSO_4 \cdot 7H_2O$ | 0.01 g/L (add 1 mL/L-medium using 10 g/L stock solution) |

Component B:

| $(NH_4)_2SO_4$ | 30 g/L |
|---|---|
| $KH_2PO_4$ | 1.5 g/L |
| Thiamine hydrochloride | 450 μg/L (add 0.45 mL/L-medium using 1 g/L stock solution) |
| Biotin | 450 μg/L (add 0.45 mL/L-medium using 1 g/L stock solution in 70% EtOH) |
| DL-methionine | 0.15 g/L |

Component C:

| $CaCO_3$ | 50 g/L |
|---|---|

The A, B, and C components were sterilized separately and mixed just before fermentation. Cells of modified YDK010 were cultivated in a volume of 4 mL of MM-medium supplemented with kanamycin (50 μg/mL) in 20-mL test-tubes upon vigorous shaking (100 rpm) at 30° C. for 48 hours. Then, cells and residual $CaCO_3$ were precipitated by centrifugation at 13000 rpm at 4° C.; and the resulting culture broth was filtered through 0.45 μm filter, aliquoted, and stored at −20° C.

1.6. SDS-PAGE Analysis of Proteins

A standard procedure was used for the routine analysis of proteins (Laemmli U.K. et al., Form-determining function of the genes required for the assembly of the head of bacteriophage T4, *J. Mol. Biol.*, 1970, 49:99-113). The polyacrylamide gel (PAG) having 30% T:3% C was stained with Coomassie R250. The minor proteins in the matrix of PAG were visualized using Dodeca Silver Stain Kit (BIO-RAD, USA, catalog No. 161-0480).

The Tricine-SDS-PAGE was used for analysis of peptides (Schagger H. and von Jagow G., Tricine-sodium dodecyl sulfate-polyacrylamide gel electrophoresis for the separation of proteins in the range from 1 to 100 kDa, *Anal. Biochem.*, 1987, 166:368-379; Schagger H., Tricine-SDS-PAGE, *Nat. Prot.*, 2006, 1:16-22; Simpson R. J., Electrophoresis of peptides: Tricine-SDS-PAGE, 2006, *CSH Protoc*. The pre-incubation in 2% solution of glutaraldehyde and silver staining were used to fix small peptides in PAG such as exenatide.

The «DTT plus» sample buffer for SDS-PAGE contained 50 mM Tris-HCl pH 6.8, 30% (v/v) glycerol, 1% SDS, 100 mM DTT. The «DTT minus» sample buffer was of the same composition but without DTT. Either buffer was added to a protein solution in relation of 1:5 (1 part of buffer to 5 parts of the protein solution) and incubated at 95° C. for 5-10 minutes.

1.7. Activity Assay

Figure 4:
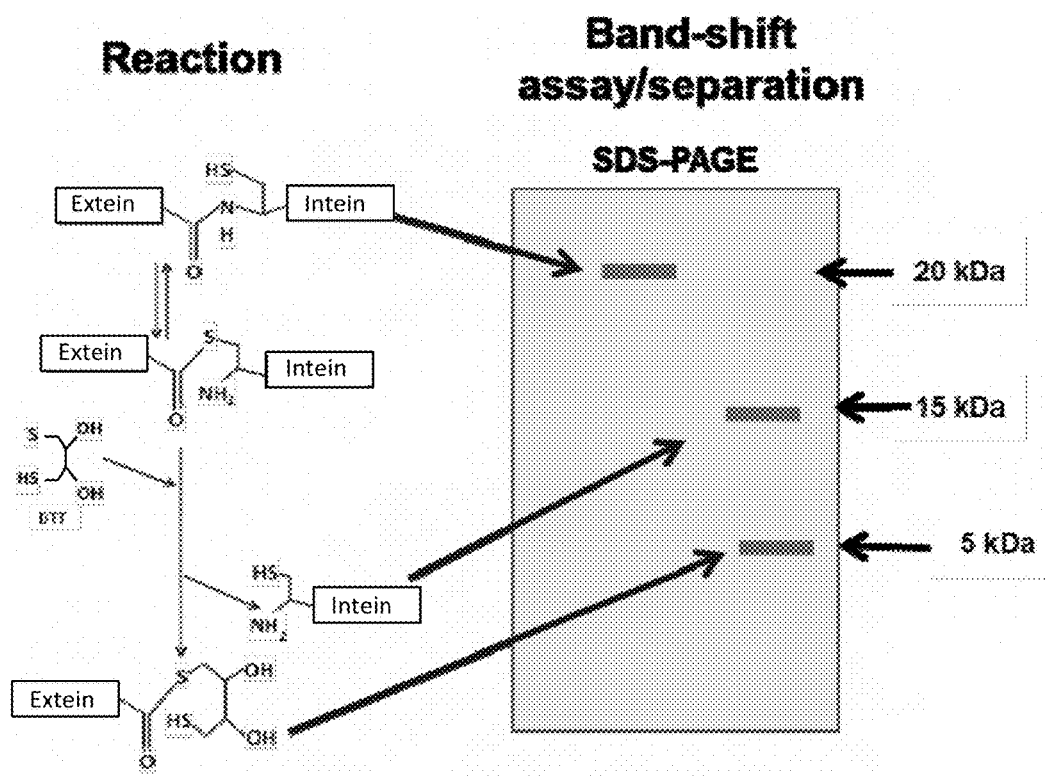
FIG. 4 shows the scheme for the SDS-PAGE band-shift assay.

The activity was studied using a band-shift assay. A scheme of the band-shift assay is described on FIG. 4. On the FIG. 4, the DTT (dithiothreitol) is a particular, non-limiting example of a nucleophilic compound. A test reaction mixture contained 100 mM Tris-HCl pH 8.0, 100 mM DTT, and a preparation of the objective protein. Control reaction was of the same composition but without DTT. Reaction mixtures were incubated at 4° C. for about 16 hours (overnight). Then, samples for SDS-PAGE were prepared using «DTT plus» and «DTT minus» sample buffers and subjected to SDS-PAGE analysis as was described in Example 1.6. Incubation of a heterologous fusion protein with a nucleophilic compound DTT results in trans-thioesterification reaction and cleavage of the heterologous fusion protein. Therefore, the band corresponding to the heterologous fusion protein disappears and two additional protein bands corresponding to an extein and an intein appear.

1.8. Purification of the Exenatide-MAG (EXI1) Fusion Protein

Purification of the exenatide-MAG heterologous fusion protein (EXI1) was performed by fast protein liquid chromatography (FPLC) using AKTA Purifier system (GE Healthcare) at 4° C. A sample of about 50-80 mL of the culture broth obtained after cultivation of the YDK010 [pEXC1-exe-MAG] strain for 48 hours (Example 1.5) was applied onto the Sephadex-G25 column (2.6×30 cm) equilibrated with 20 mM Tris-HCl pH 8.0 buffer. Isocratic elution was performed at a flow rate of 10 mL/min. Fractions containing proteins were pooled and applied onto the Source-15Q 4.6/100 PE column (GE Healthcare) equilibrated with 20 mM Tris-HCl pH 8.0 buffer. A liner gradient from 0 to 1 M in 15 column volumes of NaCl in the 20 mM Tris-HCl pH 8.0 buffer was applied for elution of bounded proteins. Fractions of 1.7 mL each were collected and analyzed by SDS-PAGE (Example 1.6). Fractions containing the EXI1 protein were pooled and stored at −20° C. If necessary, fractions were desalted using PD10 desalting columns (GE Healthcare) equilibrated with 20 mM Tris-HCl pH 8.0 buffer.

1.9. Purification of the Exenatide-MAG-HT#2 Protein (EXI1HT)

Purification of the exenatide-MAG protein having the His6-tag (EXI1 HT) was performed using immobilized metal ion affinity chromatography (IMAC). NaCl was added to a sample of 40 mL of the culture broth obtained after cultivation of the YDK010[pEXC1-exe-MAG-HT#2] strain for 48 hours (Example 1.5) to a final concentration of 500 mM. The solution was filtered through 0.45 μm filter and applied onto the HisTrap 1 mL Chelating HP column (GE Healthcare) equilibrated with HT-binding buffer (20 mM Tris-HCl, 500 mM NaCl, and 20 mM imidazole, pH 8.0). A linear gradient from 20 to 500 mM in 10-15 column volumes of imidazole in the 20 mM Tris-HCl, 500 mM NaCl, and 20 mM imidazole, pH 8.0 buffer was applied. Fractions of 1 mL each were collected and analyzed by SDS-PAGE (Example 1.6). Fractions containing the EXI1HT protein were collected, if necessary, desalted using PD10 column equilibrated with 20 mM Tris-HCl pH 8.0, and stored at −20° C.

1.10. Large-Scale Purification of the Exenatide-MAG-HT#2 (EXI1HT) Protein

Large-scale purification of the exenatide-MAG-HT#2 (EXI1HT) protein was performed using the denaturing IMAC. A sample of about 500 mL of the culture broth was obtained after cultivation of the YDK010[pEXC1-exe-MAG-HT#2] strain for 48 hours (Example 1.5) in ten 750-mL flask each containing 50 mL of the culture broth (Example 1.5). The culture broth was treated with ammonium sulfate (65% of saturation) and boiled (100° C.) for about 2-3 minutes until a protein precipitate was formed. Denatured proteins were harvested by centrifugation, dissolved in 40 mL of buffer D (20 mM Tris-HCl pH 8.0, 8 M urea, 500 mM NaCl) and incubated at 4° C. for about 16 hours (overnight). Insoluble proteins were removed by centrifugation. The final protein preparation was applied onto the HisTrap 1 mL Chelating HP column (GE Healthcare) equilibrated with buffer D. Fractions of 100 μL each were collected and analyzed by SDS-PAGE (Example 1.6). Fractions containing the EXI1HT protein were collected, supplemented with DTT to a final concentration of 200 mM, and stored at −20° C.

1.11. In Vitro Refolding of EXI1HT

1.11.1. Prolonged «Equilibrium» Refolding

A sample (0.5 mL) of a protein preparation from Example 1.10 was dialyzed for 16 hours (overnight) at room temperature against 100 mL of buffer R1 (20 mM Tris-HCl pH 8.0, 50 mM NaCl, 2 mM DTT). Then, the protein preparation was subjected to size exclusion chromatography (SEC) on the Superdex-75 10/300 column (GE Healthcare) equilibrated with the 20 mM Tris-HCl pH 8.0, 50 mM NaCl, 2 mM DTT buffer. Isocratic elution was performed at a flow rate of 0.25 mL/min. Fractions of 0.75 mL each were collected and analyzed by SDS-PAGE (Example 1.6). Fractions containing the EXI1HT protein were collected and stored at 4° C.

1.11.2. Fast «non-equilibrium» refolding

A sample (0.5 mL) of a protein preparation from Example 1.10 was subjected to size exclusion chromatography (SEC) on the Superdex-75 10/300 column (GE Healthcare) equilibrated with the 20 mM Tris-HCl pH 8.0, 50 mM NaCl, 2 mM DTT buffer. Isocratic elution was performed at a flow rate of 0.25 mL/min. Fractions of 0.75 mL each were collected and analyzed by SDS-PAGE (Example 1.6). Fractions containing the EXI1HT protein were collected and stored at 4° C.

Exenatide: Results

1.12. Purification and Activity of the Exenatide-MAG (EXI1) Fusion Protein

Figure 5:
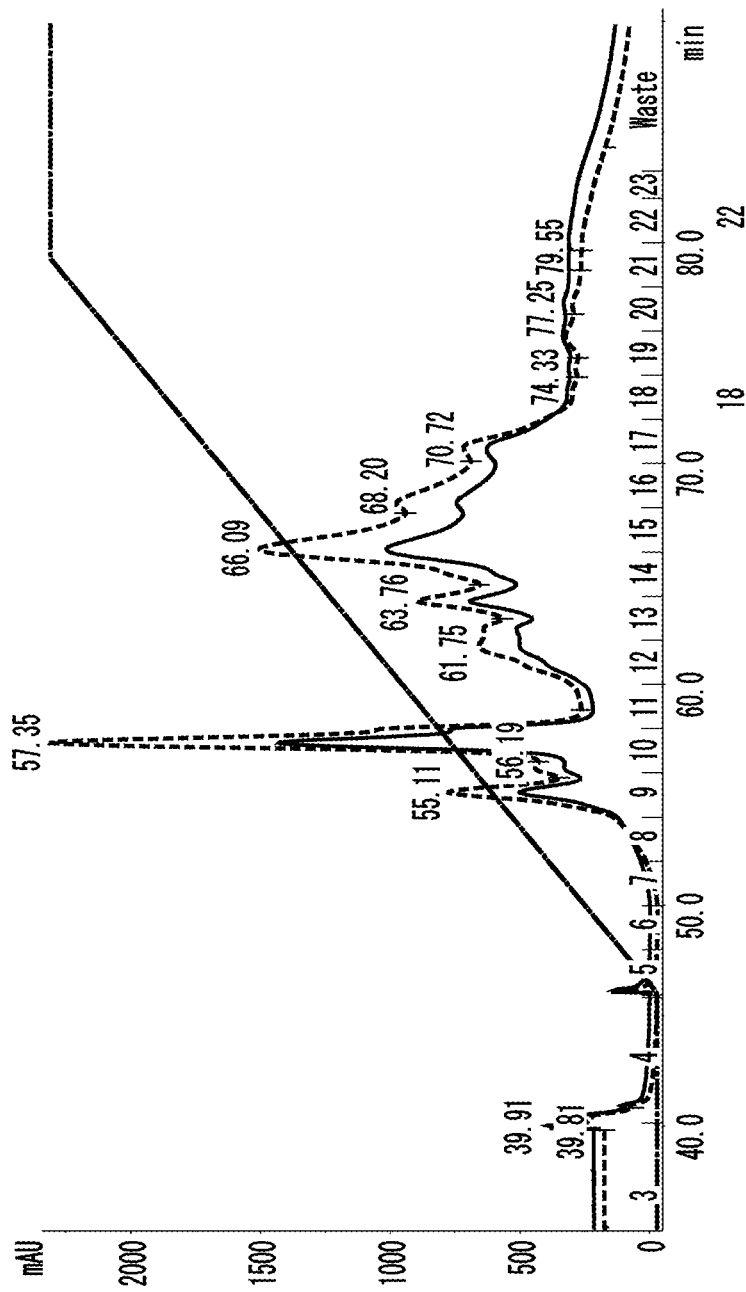
FIG. 5 shows the FPLC profile of crude mixture of EXI1.
Figure 6:
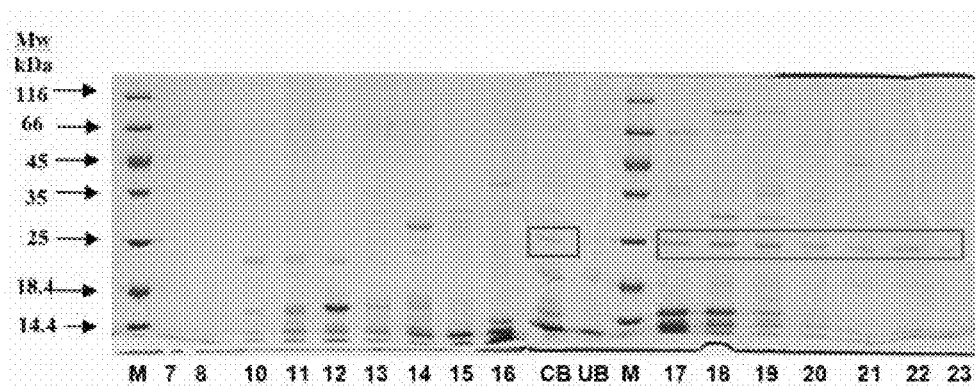
FIG. 6 shows the SDS-PAGE analysis of fractions of EXI1 (photograph).
Figure 7:
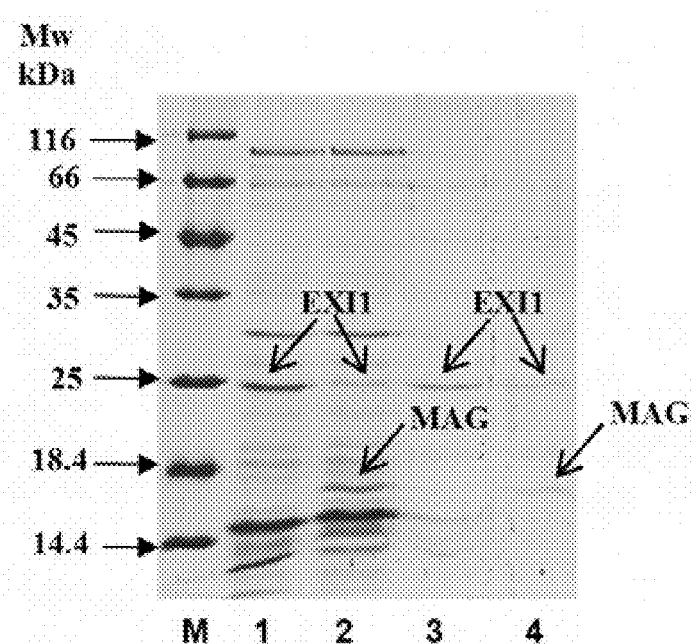
FIG. 7 shows the SDS-PAGE analysis of activity of EXI1 (photograph).

The EXI1 protein was purified using FPLC as described in Example 1.8 and analyzed using SDS-PAGE as described in Example 1.6. The EXI1 protein was eluted at high concentration of NaCl in a broad elution peak (FIGS. 5 and 6). Activity of EXI1 in fractions Nos. 18 and 22 was investigated using SDS-PAGE analysis (Example 1.7; FIG. 7). The band corresponding to EXI1 from fractions Nos. 18 and 22 disappeared and the band corresponding to intein MAG appeared upon treatment of EXI1 with DTT. Thus, activity of the EXI1 fusion protein was confirmed.

Figure 8:
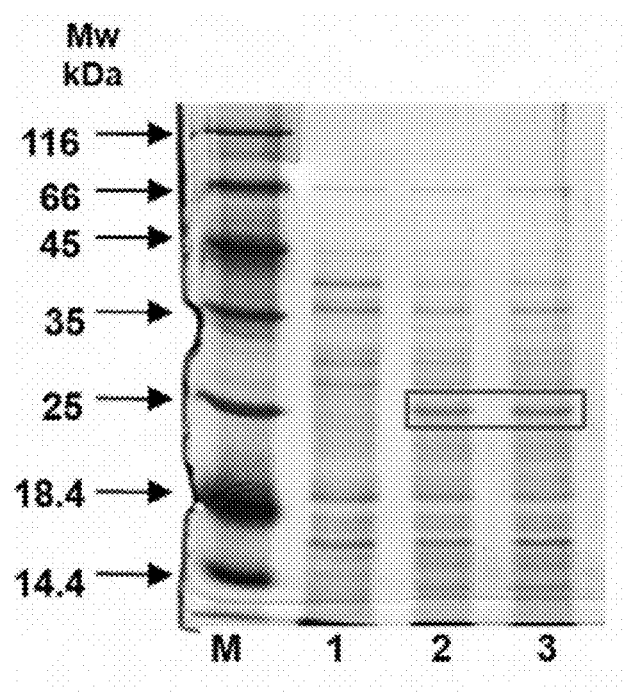
FIG. 8 shows the SDS-PAGE analysis of expression of EXI1HT (photograph).

1.13. Purification and Activity of the Exenatide-MAG-HT#2 (EXI1HT) Fusion Protein The EXI1HT protein was purified using IMAC as described in Example 1.9 and analyzed using SDS-PAGE as described in Example 1.6. Comparative SDS-PAGE analysis of proteins profile in culture broths of the control YDK010 [pEXC1] and test YDK010 [pEXC1-exe-MAG-HT#2] strains revealed a protein band corresponding to the EXI1HT protein (FIG. 8, compare lanes 1 and 2). The EXI1HT protein did not show activity in the culture broth (FIG. 8, compare lanes 2 and 3).

Figure 9:
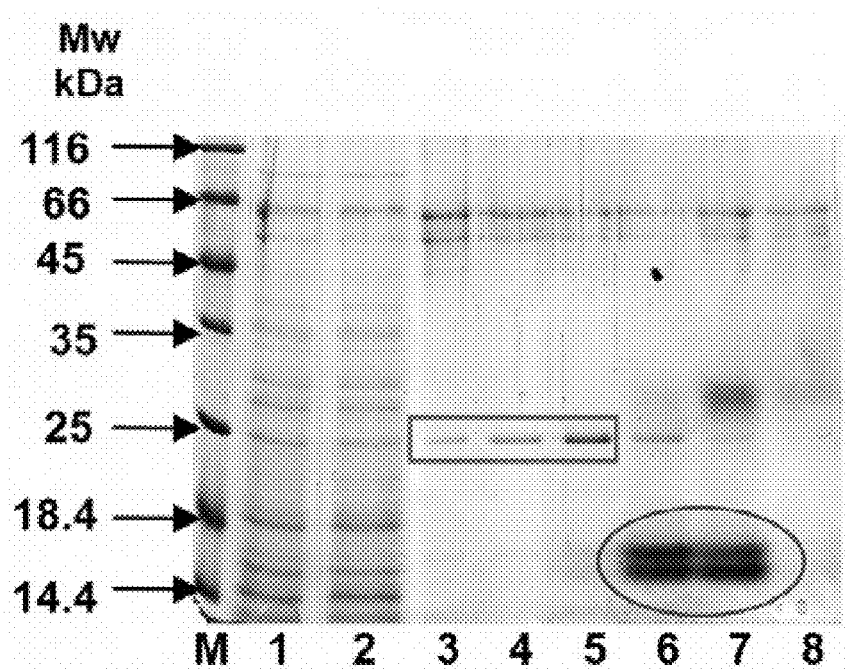
FIG. 9 shows the results of purification of EXI1HT from the YDK010[pEXC1-exe-MAG-HT#2] strain culture broth using IMAC (photograph).

Then, a purification of EXI1HT from a culture broth of the YDK010[pEXC1-exe-MAG-HT#2] strain was performed using IMAC (Example 1.9). Approximately only one third of total soluble EXI1HT was bounded to the column (FIGS. 8 and 9). Eluted EXI1HT did not show activity even after desalting using PD10 column. Therefore, the in vitro refolding of EXI1HT was used (Example 1.11).

Figure 10:
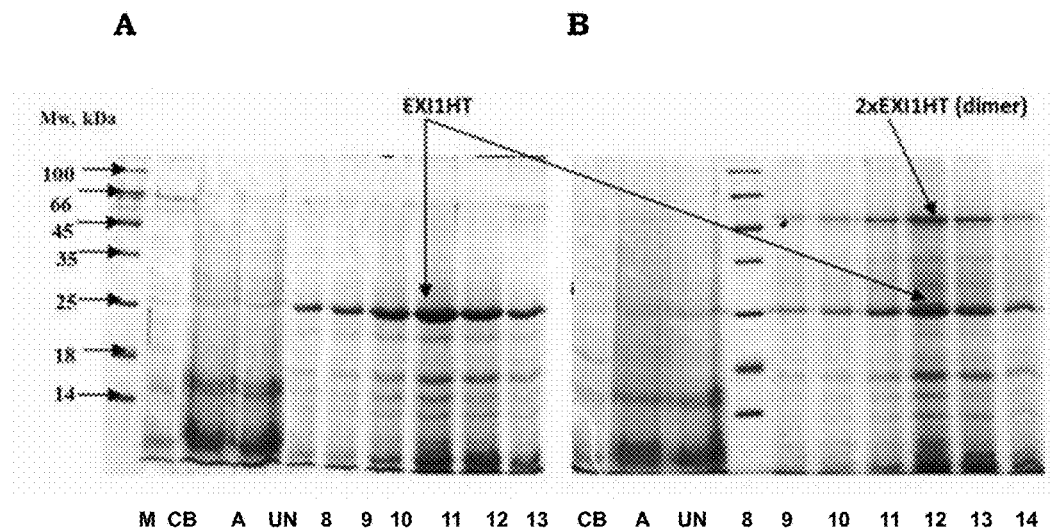
FIG. 10 shows the SDS-PAGE analysis of expression and purification of EXI1HT using denaturing IMAC (photograph).

The EXI1HT was refolded as follows. EXI1HT was completely denatured by a precipitation from the culture broth using sulfate ammonia (65% of saturation) and heating (100° C.) (Example 1.10). Precipitated proteins were dissolved in a buffer containing 8 M urea and purified using denaturing IMAC (Example 1.10). DTT was added to the resulting protein preparations up to 100 mM to accomplish a denaturation process. Comparison of reducing and non-reducing SDS-PAGEs of fractions eluted from the HisTrap column revealed a partial dimerization of EXI1HT (FIG. 10). We postulate, that EXI1HT can form a dimer through the intermolecular formation of a disulphide bond (S—S) between cysteine residues which required for the N—S shift.

Figure 11:
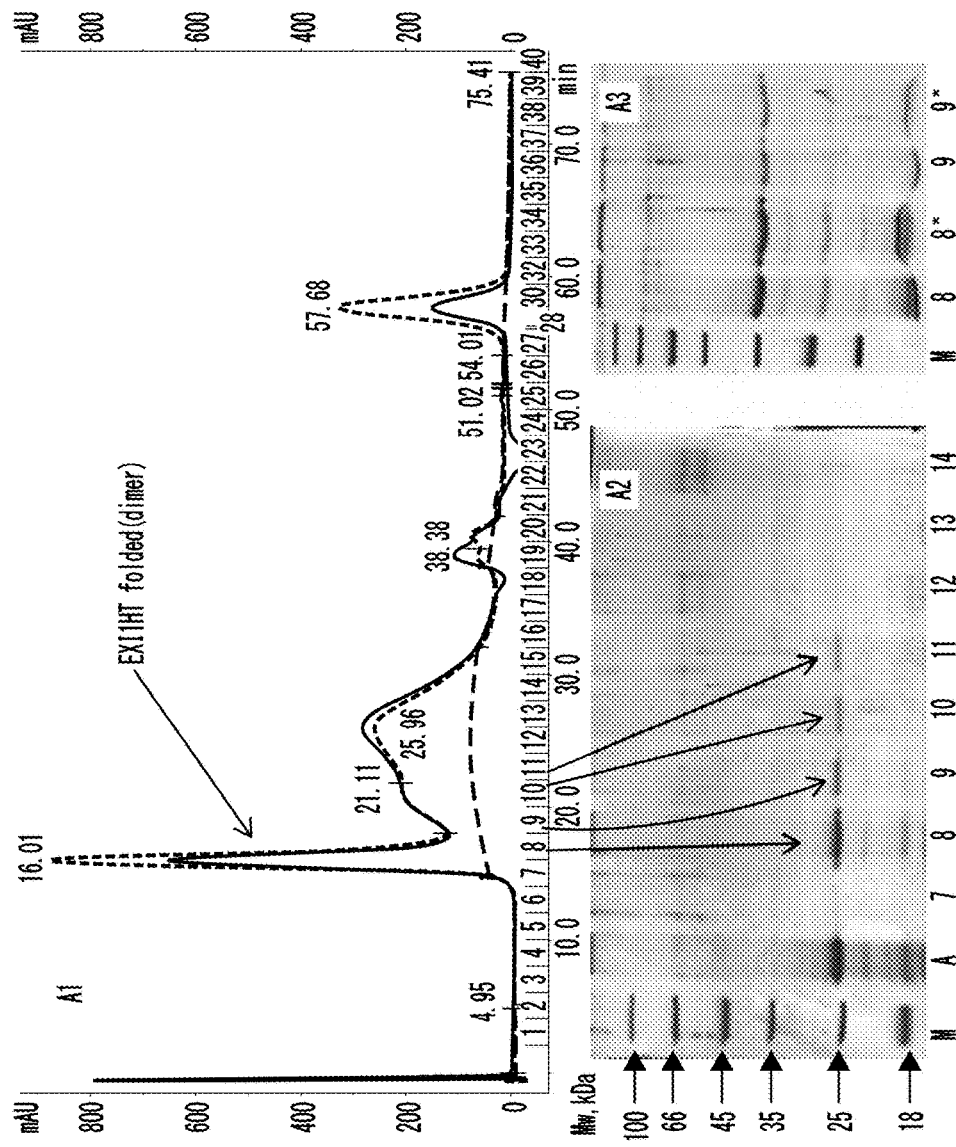
FIG. 11 shows the prolonged «equilibrium» refolding of EXI1HT (photograph).
Figure 12:
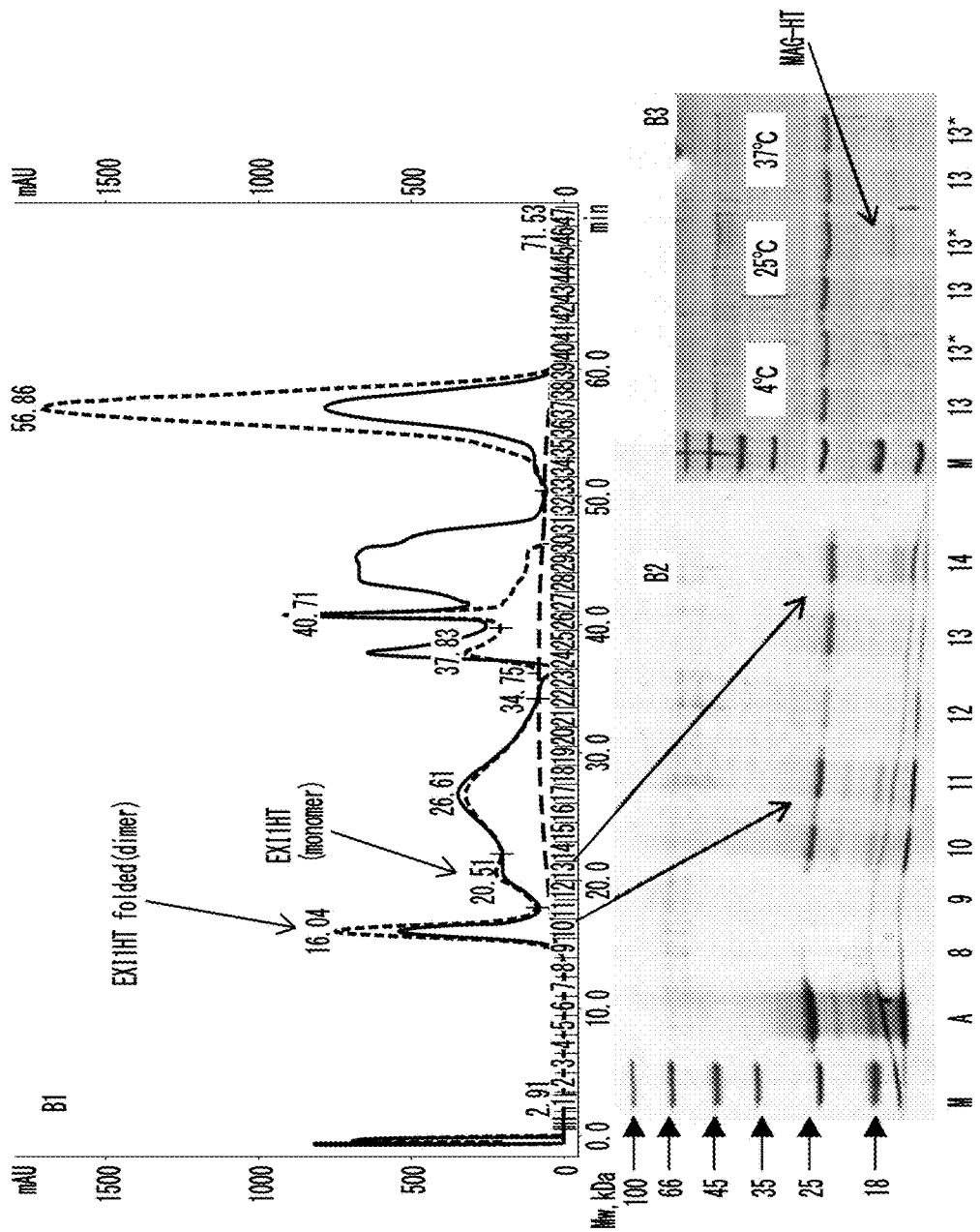
FIG. 12 shows the fast «non-equilibrium» refolding of EXI1HT (photograph).

The prolonged «equilibrium» refolding (Example 1.11.1) and fast «non-equilibrium» refolding (Example 1.11.2) were used to refold in vitro EXI1HT. The prolonged «equilibrium» refolding resulted in formation of a stable inactive dimer of the EXI1HT (FIG. 11). The fast «non-equilibrium» refolding resulted in formation of the EXI1HT dimer and a monomer of the EXI1HT (FIG. 12). The EXI1HT monomer showed activity (FIG. 12).

Example 2

Trastuzumab: Experimental Part

All plasmids and strains used are described in Tables 2 and 3.

2.1. Design and Chemical Synthesis of Intein-Encoding DNA-Fragments

The chemical synthesis of the intein-encoding DNA-fragments such as Int4 DNA-fragment (SEQ ID NO: 5), Int5 DNA-fragment (SEQ ID NO: 6), Int7 DNA-fragment (SEQ ID NO: 7), Int18 DNA-fragment (SEQ ID NO: 8), and Int19 DNA-fragment (SEQ ID NO: 19) were ordered from ATG Service Gene (Russian Federation, St.-Petersburg, www.service-gene.spb.ru).

Figure 13:
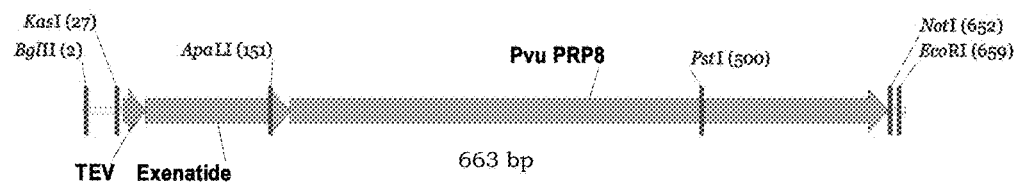
FIG. 13 shows the structure of the Int4 DNA-fragment.

The Int4 DNA-fragment encodes an artificial ORF having a TEV protease cleavage site, exenatide (SEQ ID NO: 34), and the intein Int4 (Pvu PRP8; tools.neb.com/inbase/intein.php?name=Pvu+PRP8; SEQ ID NO: 38). The original sequence of the Int4 encoding region was modified so that the last nucleotide triplet encoding asparagine (N) was deleted. The structure of the Int4 DNA-fragment is shown on FIG. 13.

Figure 14:
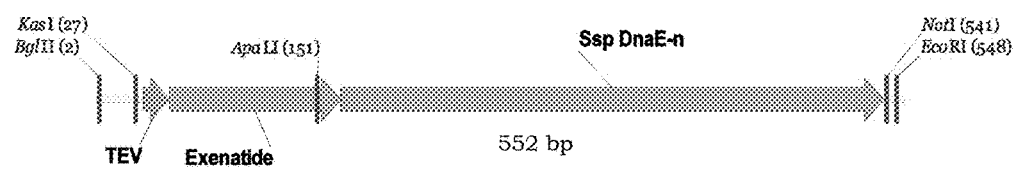
FIG. 14 shows the structure of the Int5 DNA-fragment.

The Int5 DNA-fragment encodes an artificial ORF having a TEV protease cleavage site, exenatide (SEQ ID NO: 34), and the intein Int5 (Ssp DnaE-n; tools.neb.com/inbase/intein.php?name=Ssp+DnaE-n; SEQ ID NO: 39). The original sequence of the Int5 encoding region was modified so that the last nucleotide triplet encoding asparagine (N) was deleted. The structure of the Int5 DNA-fragment is shown on FIG. 14.

Figure 15:
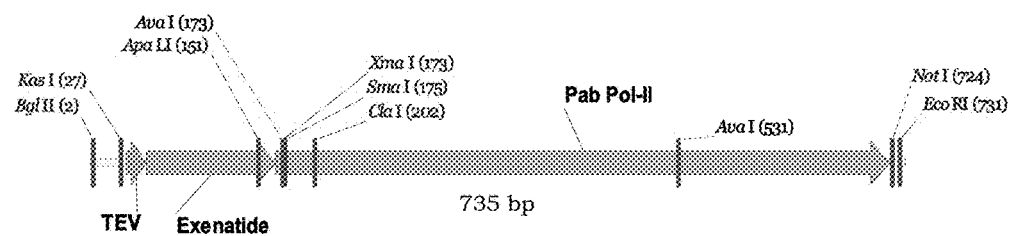
FIG. 15 shows the structure of the Int1 DNA-fragment.

The Int7 DNA-fragment encodes an artificial ORF having a TEV protease cleavage site, exenatide (SEQ ID NO: 34), and the intein Int7 (Pab Pol-II; tools.neb.com/inbase/intein.php?name=Pab+Pol-II; SEQ ID NO: 40). The original sequence of the Int7 encoding region was modified so that the last nucleotide triplet encoding asparagine (N) was deleted. The structure of the Int7 DNA-fragment is shown on FIG. 15.

Figure 16:
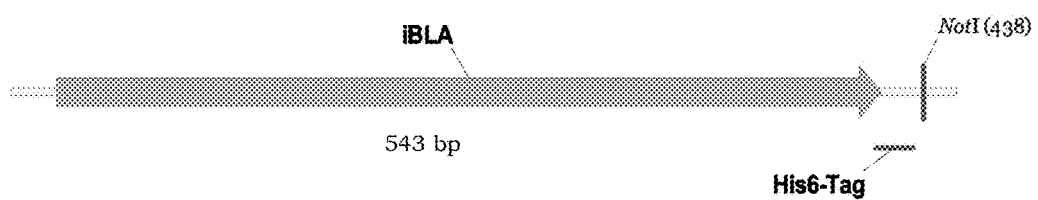
FIG. 16 shows the structure of the Int18 DNA-fragment.

The Int18 DNA-fragment encodes an artificial ORF having the intein Int18 (iBLA; SEQ ID NO: 41) and His6-tag. The structure of the Int18 DNA-fragment is shown on FIG. 16.

Figure 17:
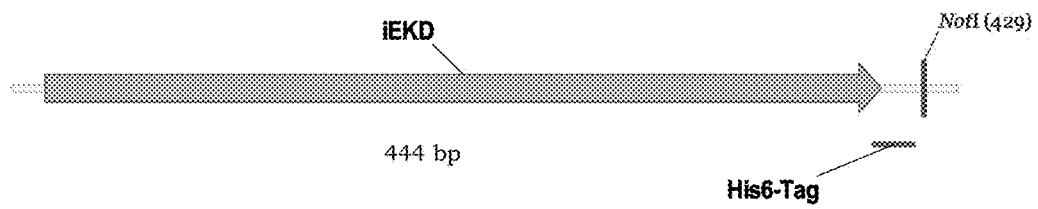
FIG. 17 shows the structure of the Int19 DNA-fragment.

The Int19 DNA-fragment encodes an artificial ORF having the intein Int19 (iEKD; SEQ ID NO: 42) and His6-tag. The structure of the Int19 DNA-fragment is shown on FIG. 17.

The intein-encoding DNA-fragments were cloned into pUC57 cloning vector (GenBank: Y14837.1; GI: 2440162) into EcoRV site. Thus the pUC57-Int4, pUC57-Int5, pUC57-Int7, pUC57-Int18(iBLA), and pUC57-Int19(iEKD) plasmids were constructed.

2.2. Construction of the pPKSherFabH-$_{TGC}$-IntX(HT)-FabL Plasmids

The technical details as to construction of pPKSherFabH-$_{TGC}$-IntX(HT)-FabL plasmids harboring trastuzumab Fab heavy chain (H) fused with MAG, Int4, Int5, Int7, Int18 or Int19 inteins (Table 2) are explained hereafter.

The [KpnI-P52-FabH-$_{TGC}$-IntX(HT)-BamHI] DNA-fragments were constructed using the steps from I to III as follows:

Step I:
DNA-fragments were PCR-amplified using primers PR1 and PR2 (Table 4) in an amount of 10 pmoles each, and a template DNA (Table 4) in an amount of 100 ng. The PCR protocol was as follows: 94° C., 30"/50° C., 30"/72° C., time T1 (see Table 4); 25 cycles.

Step II:
The plasmid pPKSherFabHL (SEQ ID NO: 60) in an amount of 10 pmoles was added to an aliquot of the mixtures obtained from Step I, and the following PCR protocol was applied: 94° C., 30"/30° C., 30"/72° C., 4'; 12 cycles.

Step III:
The primers PR2 (Table 4) and P3 (SEQ ID NO: 10) were added to an aliquot of the mixtures obtained from Step II, and the following PCR protocol was applied: 94° C., 30"/50° C., 30"/72° C., time T2 (see Table 4); 12 cycles.

The primers P3 (SEQ ID NO: 10), P4 (SEQ ID NO: 11), P5 (SEQ ID NO: 12), P6 (SEQ ID NO: 13), P7 (SEQ ID NO: 14), P8 (SEQ ID NO: 15), P9 (SEQ ID NO: 16), P10 (SEQ ID NO: 17), P11 (SEQ ID NO: 18), P12 (SEQ ID NO: 19), P13 (SEQ ID NO: 20), P14 (SEQ ID NO: 21), and P15 (SEQ ID NO: 22) were used for construction of the pPKSherFabH-$_{TGC}$-IntX(HT)-FabL plasmids.

The plasmid pPKSherFabH-$_{TGC}$-MAG(HT)-FabL (Table 4) was constructed after construction of the plasmid pPKSherFabH-$_{TGC}$-MAG-FabL. In this case, only Step I as described above was performed to synthesize the KpnI-BamHI fragment, which was directly cloned into pPKSherFabHL/KpnI-BamHI vector.

Resulting DNA-fragments were purified using electrophoresis in agarose gel, digested with KpnI and BamHI, and cloned into the pPKSherFabHL/KpnI-BamHI vector. Thus the plasmids were constructed (Table 2).

2.3. Construction of the pPKSherFabH-FabL-$_{CGC}$-IntX (HT) Plasmids

The auxiliary plasmid pPKSherFabHL-(Xba/Nhe) was constructed as follows. The 1333 bp DNA-fragment [NheI-BglII-PS2-FabL-NotI-NheI] was PCR-amplified using primers P17 (SEQ ID NO: 24) and P18 (SEQ ID NO: 25), and the pPKSherFabHL plasmid as the template. The PCR protocol was as follows: 94° C., 30"/50° C., 30"/72° C., 240"; 25 cycles. Resulting DNA-fragment was digested with NheI and ligated with pPKSherFabHL/XbaI vector. Thus the plasmid pPKSherFabHL-(Xba/Nhe) was constructed.

The [BglII-PS2-FabL-$_{CGC}$-IntX-NotI] DNA-fragments were constructed using the steps from I to III as follows:

Step I:
DNA-fragments were PCR-amplified using primers PR3 and PR4 (Table 5) in an amount of 10 pmoles each, and a template DNA (Table 5) in an amount of 100 ng. The PCR protocol was as follows: 94° C., 30"/50° C., 30"/72° C., time T3 (see Table 5); 25 cycles.

Step II:
The plasmid pPKSherFabHL (SEQ ID NO: 60) in an amount of 10 pmoles was added to an aliquot of the mixtures obtained from Step I, and the following PCR protocol was applied: 94° C., 30"/35° C., 30"/72° C., 4'; 10 cycles.

Step III:
The primers PR4 (Table 5) and P17 (SEQ ID NO: 24) were added to an aliquot of the mixtures obtained from Step II, and the following PCR protocol was applied: 94° C., 30"/35° C., 30"/72° C., time T4 (see Table 5); 10 cycles.

Resulting DNA-fragments were purified using electrophoresis in agarose gel, digested with BglII and NotI, and cloned into the pPKSherFabHL-(Xba/Nhe)/BglII-NotI vector. Thus the plasmids were constructed (Table 2).

2.4. Construction of the pPKSherFabH-FabL-$_{CGC}$-MAG-HT Plasmid

The DNA-fragment [FabL-$_{CGC}$-MAG-HT] (1757 bp) was PCR-amplified using primers P16 (SEQ ID NO: 23) and P17 (SEQ ID NO: 24), and the plasmid pPKSherFabH-FabL-$_{CGC}$-MAG as the template (Example 2.3). The PCR protocol was as follows: 95° C., 10"/52° C., 15"/72° C., 240"; 25 cycles). Obtained DNA-fragment was digested with BglII and NotI, purified by electrophoresis in agarose gel, and ligated with pPK-SherFabHL-(Xba/Nhe)/BglII-NotI vector. The resulting ligation mixture was introduced into JM109 strain (Promega, catalog No. P9751) calcium chloride transformation procedure (Mandel M. and Higa A., Calcium-dependent bacteriophage DNA infection, *J. Mol. Biol.*, 1970, 53:159-162). Thus, about 200 kanamycin-resistant (Kn$^R$) colonies were obtained. Restriction analysis of plasmids isolated from twelve arbitrary chosen clones revealed twelve plasmids with desired structure.

2.5. Cultivation of *C. glutamicum* Plasmid Strains

The *C. glutamicum* YDK010 (WO2004/029254) and YDK010ΔPBP1a strains harboring plasmids (Table 2) were cultivated in MM-medium as described in Example 1.5. Construction of *C. glutamicum* YDK010ΔPBP1a strain is described in Auxiliary example 1. Cells were cultivated in 4 mL of MM-medium supplemented with kanamycin (50 μg/mL) in 20-mL test-tubes upon vigorous shaking (200-250 rpm) at 30° C. for 48-72 hours. Then, cells and residual CaCO$_3$ were precipitated by centrifugation at 13000 rpm at 4° C.; and the resulting culture broth was filtered through 0.45 μm filter, aliquoted, and stored at −20° C.

2.6. SDS-PAGE Analysis of Proteins

A standard procedure was used for the routine analysis of proteins (Laemmli U.K. et al., Form-determining function of the genes required for the assembly of the head of bacteriophage T4, *J. Mol. Biol.*, 1970, 49:99-113). The polyacrylamide gel (PAG) having 30% T: 3% C was stained with Coomassie R250. The minor proteins in the matrix of PAG were visualized using Dodeca Silver Stain Kit (BIO-RAD, USA, catalog No. 161-0480).

The «DTT plus» sample buffer for SDS-PAGE contained 50 mM Tris-HCl pH 6.8, 30% (v/v) glycerol, 1% SDS, 100 mM DTT. The «DTT minus» sample buffer was of the same composition but without DTT. Either buffer was added to a protein solution in relation of 1:5 (1 part of either buffer to 5 parts of the protein solution) and incubated at 95° C. for 5-10 minutes.

Reaction mixture for the activity assay contained: 100 mM Tris-HCl pH 8-11, 100 mM DTT, and protein preparation. Control reaction contained all components with exception of DTT. All reactions were incubated at incubated at 4° C. for about 16 hours (overnight) and then subjected to the SDS-PAGE band shift analysis.

2.7. Activity Assay

The activity was studied using a band-shift assay as described in Example 1.7. A test reaction mixture contained 100 mM Tris-HCl pH 8.0, 100 mM DTT, and a preparation of the objective protein. Control reaction was of the same composition but without DTT. Reaction mixtures were incubated at 4° C. for about 16 hours (overnight). Then, samples for SDS-PAGE were prepared using «DTT plus» and «DTT minus» sample buffers and subjected to SDS-PAGE analysis as was described in Example 2.6.

2.8. Purification of the FabH-$_{TGC}$-IntX-HT, X=4, 5, 7, 18 or 19, and FabL-$_{CGC}$-MAG-HT Fusion Proteins Purification of the FabH-$_{TGC}$-IntX-HT, X=4, 5, 7, 18 or 19, and FabL-$_{CGC}$-MAG-HT fusion proteins was performed using IMAC (Example 1.9). A sample of about 100 mL of the culture broth obtained after cultivation of the YDK010ΔPBP1a[pPKSherFabH-$_{TGC}$-IntX(HT)-FabL] and YDK010ΔPBP1a [pPKSherFabH-FabL-$_{CGC}$-MAG-HT] strains for 48 hours (Example 2.5) were subjected to treatment with ammonium sulfate (from 65% to 75% of saturation). Precipitated proteins were harvested by centrifugation, dissolved in 10-12 mL of HisTrap binding buffer (20 mM Tris-HCl, 500 mM NaCl, and 20 mM imidazole, pH 8.0), and applied onto the HisTrap 1 mL Chelating HP column (GE Healthcare). An isocratic elution was applied using the HT-binding buffer (20 mM Tris-HCl, 500 mM NaCl, and 20 mM imidazole, pH 8.0). Fractions of 100 μL each were collected and analyzed by SDS-PAGE (Example 2.6). Fractions containing the FabH-$_{TGC}$-IntX-HT and FabL-$_{CGC}$-MAG-HT proteins were collected and stored at −20° C.

Trastuzumab: Results

2.9. Purification and Activity of Fusion Proteins

The fusion proteins were purified from culture broths obtained after cultivation of the plasmid strains described in Table 3. The proteins profile of the final culture broths and activity of fusion proteins were analyzed using SDS-PAGE band-shift (Examples 2.6 and 2.7). The data for expression and activity of the FabH-$_{TGC}$-IntX(HT) and FabL-$_{CGC}$-IntX (HT) fusion proteins, where X=4, 5, 7, 18 or 19, or IntX=MAG, if X=1 are shown on FIGS. 18-26 and summarized in Table 9.

2.9.1. FabH-$_{TGC}$-MAG-HT

The FabH-$_{TGC}$-MAG-HT fusion protein was purified using denaturating and non-denaturating IMAC. FIG. 8A shows results of SDS-PAGE analysis of fractions 8-14 eluted from HisTrap column under denaturating conditions. FIG. 18B shows results of SDS-PAGE analysis of fractions 8-11 eluted from HisTrap column under non-denaturating conditions. FIG. 18C shows the same SDS-PAGE analysis as on FIG. 18B, but all samples were prepared using a sample buffer without DTT. FIG. 18D shows results confirming activity of the FabH-$_{TGC}$-MAG-HT fusion protein from fractions 9 and 10.

2.9.2. FabL-$_{CGC}$-MAG-HT

Figure 19:
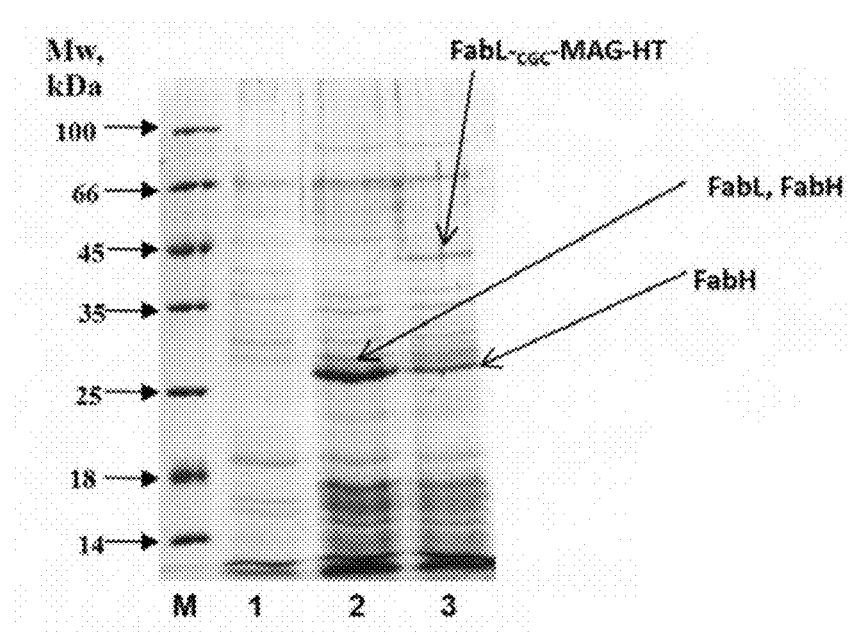
FIG. 19 shows the SDS-PAGE analysis of expression of FabL-$_{CGC}$-MAG-HT (photograph).
Figure 20:
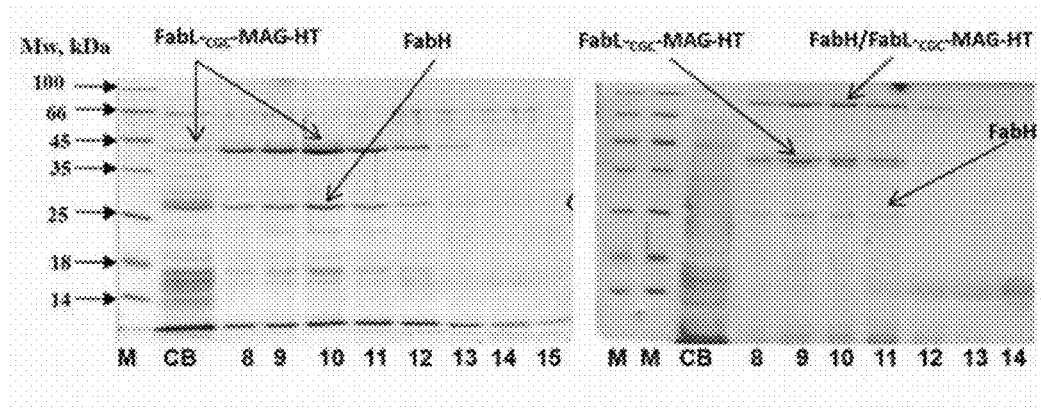
FIG. 20 shows the SDS-PAGE analysis of purification of FabL-$_{CGC}$-MAG-HT (photograph).
Figure 21:
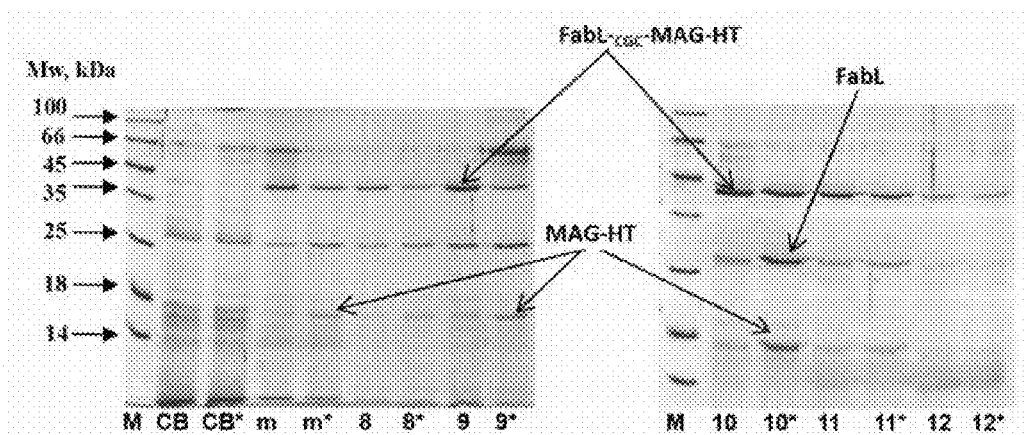
FIG. 21 shows the SDS-PAGE analysis of activity of FabL-$_{CGC}$-MAG-HT (photograph).

FIG. 19 shows reducing SDS-PAGE analysis of culture broth for expression of FabL-$_{CGC}$-MAG-HT fusion protein. The FabL-$_{CGC}$-MAG-HT fusion protein was purified using denaturating and non-denaturating IMAC. FIG. 20A shows results of SDS-PAGE analysis of fractions 8-15 eluted from HisTrap column under denaturating conditions. FIG. 20B shows results of SDS-PAGE analysis of fractions 8-15 eluted from HisTrap column under non-denaturating conditions. Activity of FabL-$_{CGC}$-MAG-HT was confirmed using reducing SDS-PAGE of mixtures containing FabL-$_{CGC}$-MAG-HT from fractions 8-12 shown on FIG. 20 (FIG. 21).

2.9.3. FabH-$_{TGC}$-IntX-HT, X=4, 5 or 7

Figure 23:
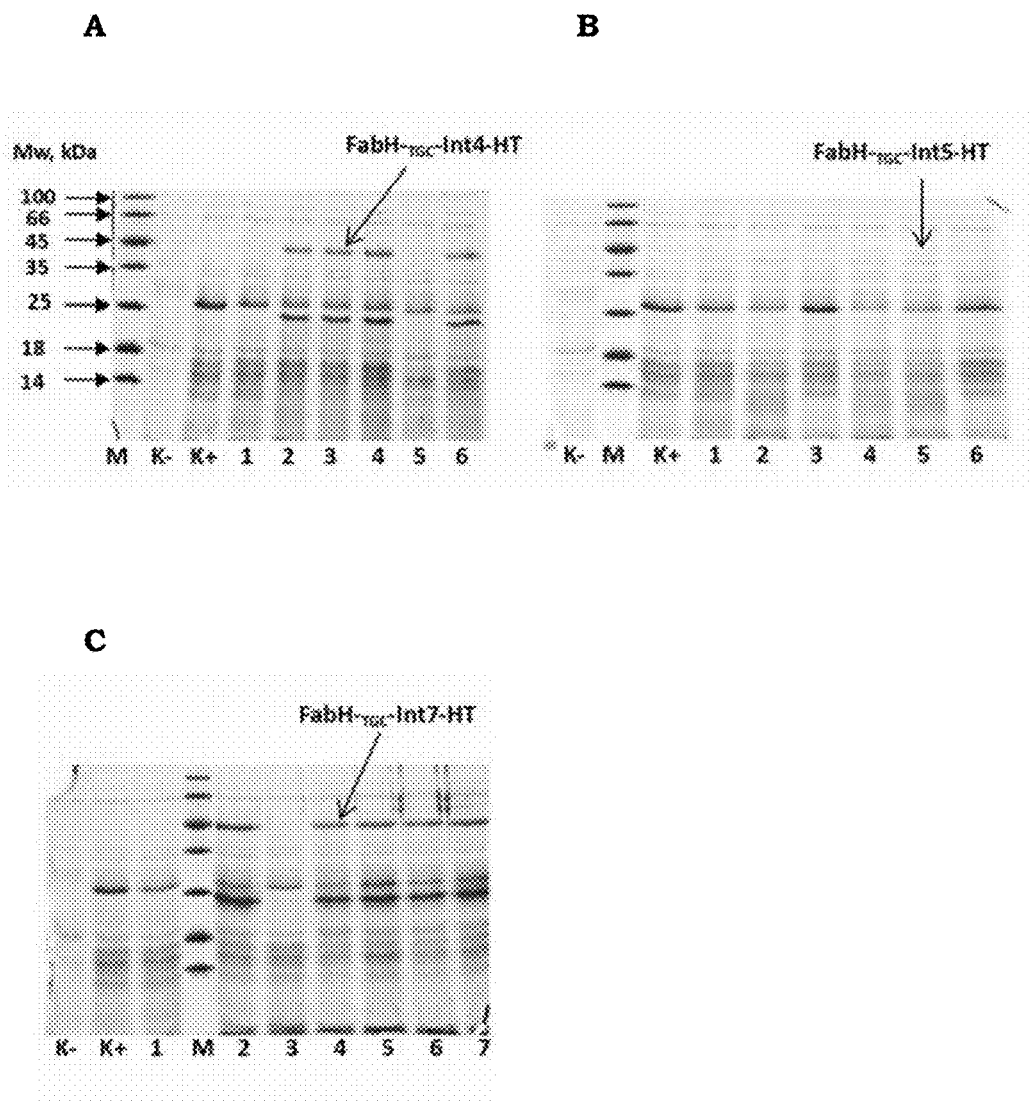
FIG. 23 shows the SDS-PAGE analysis of expression of FabH-$_{TGC}$-IntX-HT, X=4, 5 or 7 (photograph).
Figure 24:
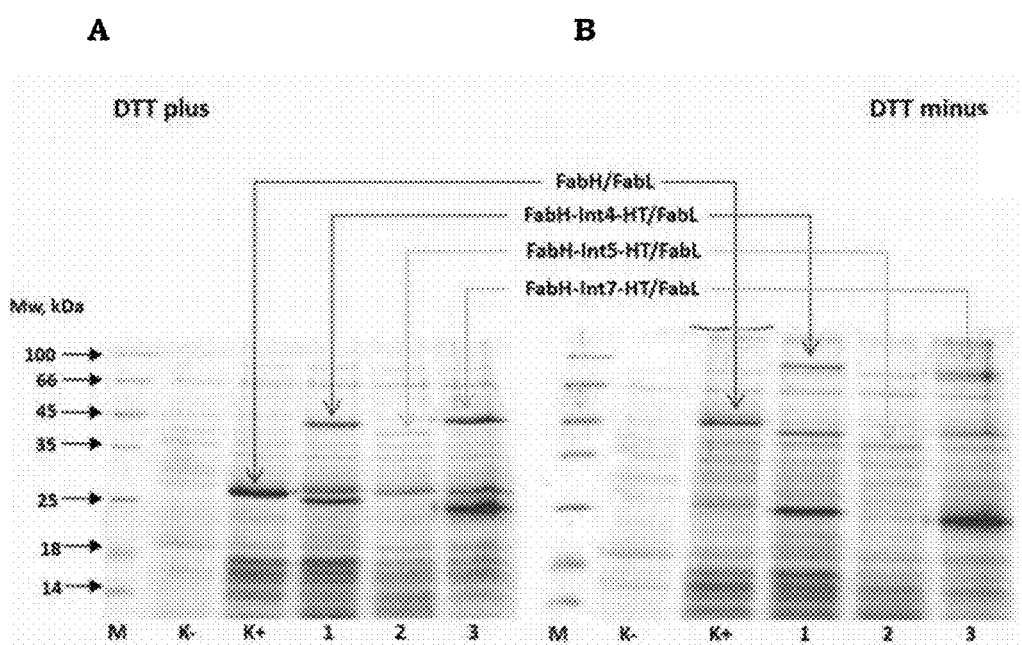
FIG. 24 shows the reducing and non-reducing SDS-PAGE of FabH-$_{TGC}$-IntX-HT, X=4, 5 or 7 (photograph).
Figure 25:
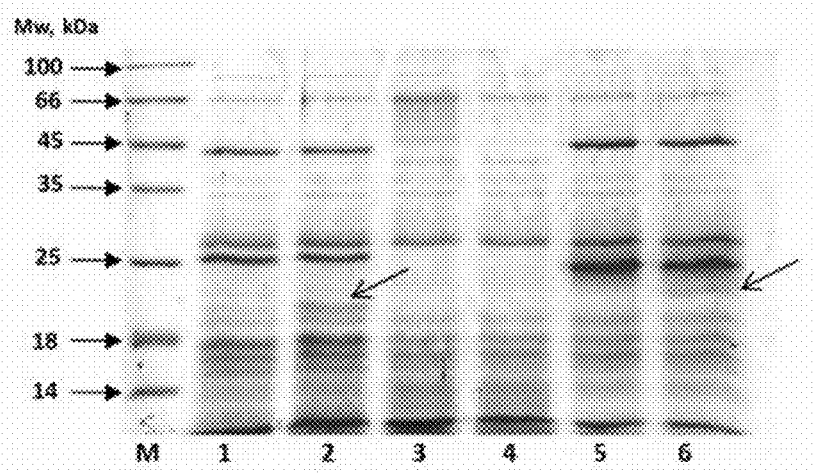
FIG. 25 shows the SDS-PAGE analysis of activity of FabH-$_{TGC}$-IntX-HT, X=4, 5 or 7 (photograph).

FIG. 22 shows reducing SDS-PAGE analysis of crude cell lysates of the YDK010ΔPBP1a strain harboring the plasmids pEXC1, pPKSherFabHL, pPKSherFabH-FabL-$_{CGC}$-MAG-HT, pPKSherFabH-FabL-$_{CGC}$-Int4, pPKSherFabH-FabL-$_{CGC}$-Int5, and pPKSherFabH-FabL-$_{CGC}$-Int7. FIG. 23 shows reducing SDS-PAGE analysis of culture broth for expression of FabH-$_{TGC}$-Int4-HT, FabH-$_{TGC}$-Int5-HT, and FabH-$_{TGC}$-Int7-HT fusion proteins. Comparative analysis of the culture broths of the YDK010ΔPBP1a strain harboring the plasmids pPKSherFabH-FabL-$_{CGC}$-IntX, where X=4, 5 or 7 was performed using reducing (FIG. 24A) and non-reducing (FIG. 24B) SDS-PAGE. Activity of FabH-$_{TGC}$-IntX-HT, X=4, 5 or 7 was confirmed using reducing SDS-PAGE of mixtures containing FabH-$_{TGC}$-IntX-HT, X=4, 5 or 7 (FIG. 25). The aliquots of culture broths of corresponding strains were used as protein preparations. Reactions were performed at 20° C. for about 16 hours (overnight).

2.9.4. FabH-$_{TGC}$-IntX-HT, X=18 or 19

Figure 26:
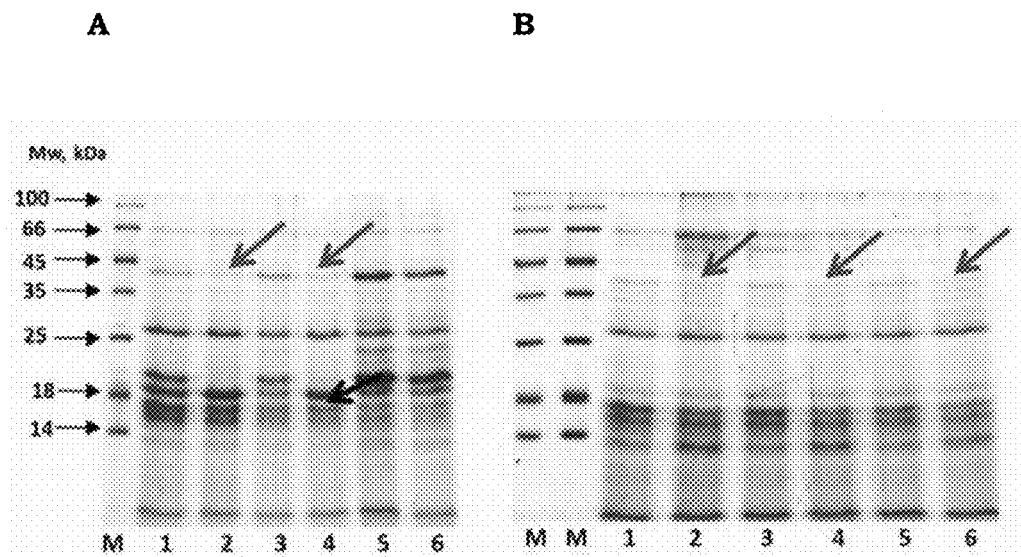
FIG. 26 shows the SDS-PAGE analysis of activity of FabH-$_{TGC}$-IntX-HT, X=18 or 19 (photograph).

The inteins Int18 (iBLA) and Int19 (iEKD) were found by a homology search for the MAG intein using the BLAST service (Table 6). Two intein-like proteins such as iBLA (Table 7) and iEKD (Table 8) were selected for cloning. The FabH-$_{TGC}$-IntX-HT, X=18 or 19 fusion proteins were expressed, purified and analyzed as described for FabH-$_{TGC}$-IntX-HT, X=4, 5 or 7 proteins (Example 2.9.3). Activity of FabH-$_{TGC}$-IntX-HT, X=18 or 19 was confirmed using reducing SDS-PAGE of mixtures containing FabH-$_{TGC}$-IntX-HT, X=18 or 19 (FIG. 26). The aliquots of culture broths of corresponding strains were used as protein preparations. Reactions were performed at 20° C. for about 16 hours (overnight).

Example 3

Trastuzumab Tagged with CBD 3.1. Construction of the pPKSher-CBD Plasmid

Figure 27:
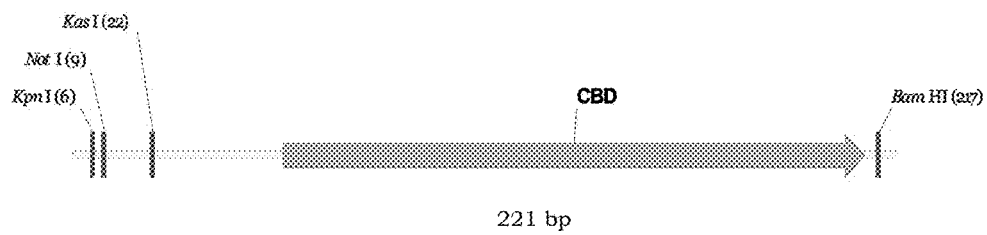
FIG. 27 shows the structure of the CBD DNA-fragment.

The chemical synthesis of the CBD DNA-fragment (SEQ ID NO: 65) was ordered from ATG Service Gene (Russian Federation, St.-Petersburg, www.service-gene.spb.ru). The CBD DNA-fragment encodes a structural part of the chitin binding domain (CBD) of 52 amino acid residues in length (GenBank: AAD49604.1; SEQ ID NO: 66). The structure of the CBD DNA-fragment is shown on FIG. 27. The CBD DNA-fragment was cloned into pUC57 cloning vector (GenBank: Y14837.1; GI: 2440162) into EcoRV site. Thus the plasmid pUC57-CBD was constructed.

The CBD DNA-fragment was excised from pUC57-MAG plasmid using KpnI and BamHI, purified by electrophoresis in agarose gel, and ligated with pPKSherFabHL vector (Table 2) into KpnI/BamHI restriction sites. Thus the pPKSher-CBD plasmid was constructed.

3.2. Construction of the pPKSherFabH-$_{TGC}$-IntX(CBD)-FabL Plasmids

The technical details as to construction of pPKSherFabH-$_{TGC}$-IntX(CBD)-FabL plasmids harboring trastuzumab Fab heavy chain (H) fused with Int1 or Int18 inteins (Table 6; SEQ ID NOs: 40 and 41) are explained hereafter.

The NotI-PS2-FabH-$_{TGC}$-Int1-KasI and NotI-PS2-FabH-$_{TGC}$-Int18-KasI DNA-fragments were PCR-amplified using primers PR5 and PR6 (Table 10) in an amount of 10 pmoles each, and a template DNA (Table 10) in an amount of 100 ng. The PCR protocol was as follows: 94° C., 30″/50° C., 30″/72° C., 4′; 25 cycles.

Resulting DNA-fragments were purified using electrophoresis in agarose gel, digested with NotI and KasI, and cloned into the pPKSher-CBD/NotI-KasI vector. Thus the pPKSherFabH-$_{TGC}$-Int7(CBD)-FabL and pPKSherFabH-$_{TGC}$-Int18(CBD)-FabL plasmids were constructed.

3.3. DTT-Dependent Self-Cleavage Activity Assay of the FabH-$_{TGC}$-IntX-CBD Fused Proteins The *C. glutamicum* YDK010 (WO2004/029254) strain harboring pPKSherFabH-$_{TGC}$-Int7(CBD)-FabL and pPKSherFabH-$_{TGC}$-Int18(CBD)-FabL plasmids were cultivated in MM-medium as described in Example 1.5. Cells were cultivated in 4 mL of MM-medium supplemented with kanamycin (50 µg/mL) in 20-mL test-tubes upon vigorous shaking (200-250 rpm) at 30° C. for 48 hours. Then, cells and residual CaCO$_3$ were precipitated by centrifugation at 13000 rpm at 4° C.; and the resulting 3 mL of culture broth was diluted in 1:1 ratio with 3 mL of buffer A (20 mM HEPES pH 8.0, 0.5 M NaCl, 0.1 mM EDTA).

Then, the 500 µL of Chitin Resin (New England BioLabs; catalog No. S6651L) equilibrated with buffer A was added to the 6 mL of diluted culture broth and incubated at room temperature (25° C.) for 15 minutes with gentle agitation.

The Chitin Resin with absorbed proteins was harvested by centrifugation, decanted, and washed twice with 5 mL of buffer A.

DTT (up to final concentration of 50 mM) was added to the 40 µL of Chitin Resin with absorbed proteins and incubated in 1.5-mL Eppendorf vials at room temperature (25° C.) for 16 hours (overnight). The control reaction was the same but without DTT addition.

The control and test vials were punctured at the bottom by hypodermic needle, inserted into the new 1.5 mL vials, and centrifuged at 2000 rpm for 3 minutes thus allowing to separate the buffer with eluted proteins (as a solution penetrating through a micro-hole in the bottom of vials) and Chitin Resin (as a solid remaining in vials).

Figure 28:
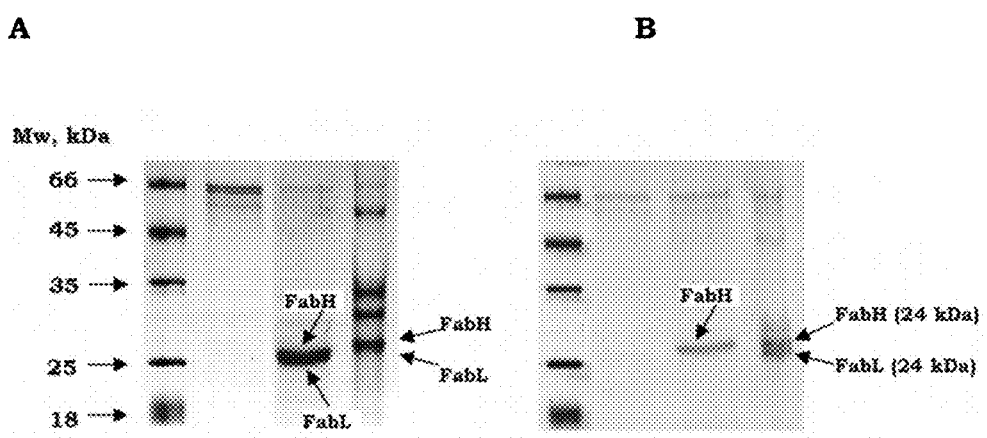
FIG. 28 shows the SDS-PAGE analysis of activity of FabH-$_{TGC}$-Int7-CBD (A) and FabH-$_{TGC}$-Int18-CBD (B) (photograph).

Aliquots of the resulting control and test preparations were subjected to SDS-PAGE analysis. Activity of FabH-$_{TGC}$-IntX-CBD (X=7 or 18) was confirmed using reducing SDS-PAGE of mixtures containing FabH-$_{TGC}$-IntX-CBD, X=7 or 18 fused proteins (FIG. 28).

Example 4

Exenatide Tagged with CBD 4.1. Construction of the pEXC1-CS-Exe-MAG-CBD Plasmid

Figure 31:
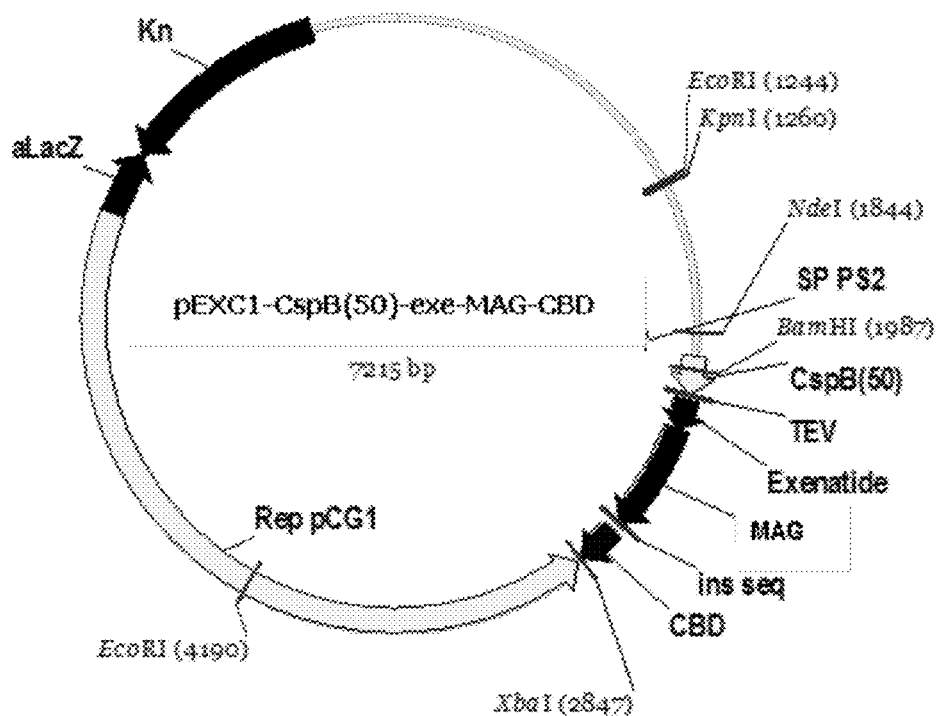
FIG. 31 shows the scheme for pEXC1-CspB(50)-exe-MAG-CBD plasmid.

The following procedure was applied to construct the pEXC1-CS-exe-MAG-CBD plasmid. A DNA-fragment was PCR-amplified using primers P34 (SEQ ID NO: 70) and P35 (SEQ ID NO: 71) in an amount of 10 pmoles each and plasmid pEXC1-CspB(50)-exe-MAG-CBD (FIG. 31, SEQ ID NO: 74) as the template (100 ng). The PCR protocol was as follows: 94° C., 5′; 94° C., 30″/53° C., 30″/72° C., 1′; 25 cycles.

Resulting DNA-fragment (0.8 kbp) was purified using electrophoresis in agarose gel, digested with KasI and BamHI, and ligated with pEXC1/KasI-BamHI vector (Table 2). Resulting ligated DNA was introduced into TG1 strain (Table 1) using the standard calcium-dependent transformation. The ampicillin-resistant (Ap$^R$) colonies were selected on L-agar-plates. The plasmid DNA was purified from ten arbitrary chosen colonies and subjected to BamHI and EcoRI digestion. Thus the pEXC1-CS-exe-MAG-CBD plasmid was constructed.

4.2. Construction of the pEXC1-BLA-Exe-MAG-CBD Plasmid

The KasI-NotI DNA-fragment harboring structural part (that is, the part lacking nucleotide sequence encoding a leader peptide having the sequence of MSIQHFRVA-LIPFFAAFCLPVFA (SEQ ID NO: 75)) of the bla gene encoding beta-lactamase (TEM; YP_006952162) was PCR-amplified using primers P36 (SEQ ID NO: 72) and P37 (SEQ ID NO: 73) in an amount of 10 pmoles each and plasmid pET15(b+) (Novagen, Germany, catalog No. 69661-3) as the template (100 ng).

Resulting DNA-fragment (0.8 kbp) was purified using electrophoresis in agarose gel, digested with KasI and NotI, and ligated with pEXC1-CS-exe-MAG-CBD/KasI-NotI vector (Example 4.1). Resulting ligated DNA was introduced into TG1 strain using the standard calcium-dependent transformation. The Ap$^R$ colonies were selected on L-agar-plates. The plasmid DNA was purified from ten arbitrary chosen colonies and subjected to BamHI and EcoRI digestion. Thus the pEXC1-BLA-exe-MAG-CBD plasmid was constructed.

Figure 29:
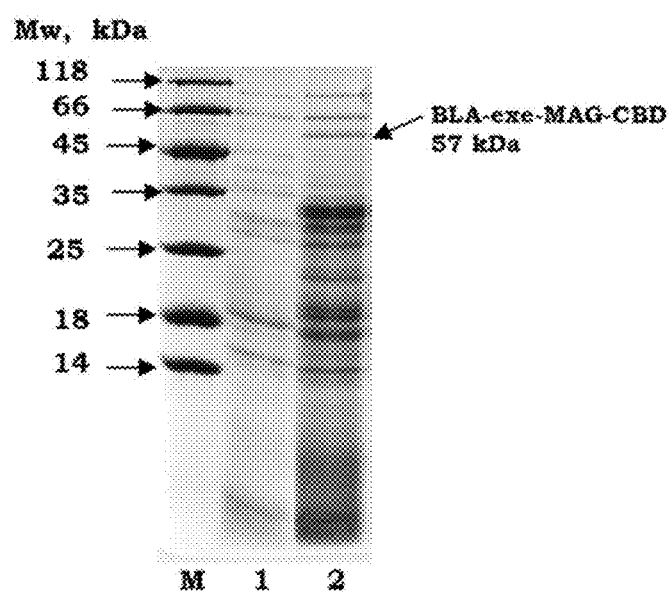
FIG. 29 shows the SDS-PAGE analysis of expression of BLA-exe-MAG-CBD (photograph).

4.3. DTT-Dependent Self-Cleavage Activity Assay of the BLA-Exe-MAG-CBD Fused Protein The *C. glutamicum* YDK010 (WO2004/029254) strain harboring pEXC1-BLA-exe-MAG-CBD plasmid was cultivated in MM-medium as described in Example 1.5. Cells were cultivated in 4 mL of MM-medium supplemented with kanamycin (50 µg/mL) in 20-mL test-tubes upon vigorous shaking (200-250 rpm) at 30° C. for 48 hours. Then, cells and residual $CaCO_3$ were precipitated by centrifugation at 13000 rpm at 4° C., and 3 mL of the resulting culture broth was diluted in 1:1 ratio with 3 mL of buffer A (20 mM HEPES pH 8.0, 0.5 M NaCl, 0.1 mM EDTA). The culture broth was subjected to SDS-PAGE analysis for proteins profile (FIG. 29).

Then, the 500 µL of Chitin Resin (New England BioLabs; catalog No. S6651L) equilibrated with buffer A was added to the 6 mL of diluted culture broth and incubated at room temperature (25° C.) for 15 minutes with gentle agitation of mix.

Then Chitin Resin with absorbed proteins was harvested by centrifugation, decanted, and washed twice with 5 mL of buffer A.

DTT (up to final concentration of 50 mM) was added to the 40 µL of Chitin Resin with absorbed proteins and incubated in 1.5-mL Eppendorf vials at room temperature (25° C.) for 16 hours (overnight). The control reaction was the same but without DTT addition.

The control and test vials were punctured at the bottom by hypodermic needle, inserted into the new 1.5 mL vials, and centrifuged at 2000 rpm for 3 minutes thus allowing to separate the buffer with eluted proteins (as a solution penetrating through a micro-hole in the bottom of vials) and Chitin Resin (as a solid remaining in vials).

Figure 30:
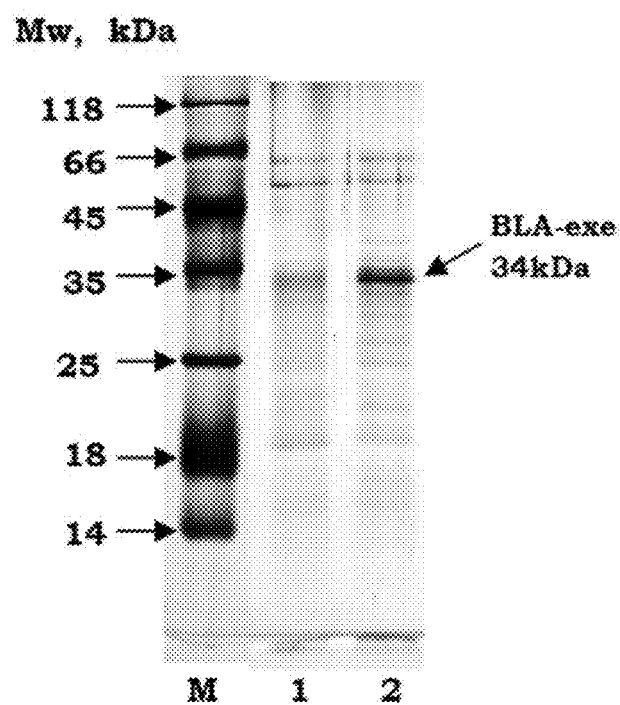
FIG. 30 shows the SDS-PAGE analysis of activity of BLA-exe-MAG-CBD (photograph).

Aliquots of the resulting control and test preparations were subjected to SDS-PAGE analysis. Activity of BLA-exe-MAG-CBD was confirmed using reducing SDS-PAGE of a mixture containing BLA-exe-MAG-CBD fused protein (FIG. 30).

Example 5

Modification of C-Terminus of Trastuzumab 5.1. Secretory Production of FabHL and FabH-$_{TGC}$-Int7-HT-FabL The YDK010ΔPBP1a strain (Auxiliary example 1.2) harboring pPKSherFabHL and pPKSherFabH-$_{TGC}$-Int7-HT-FabL plasmids (Table 2) is inoculated in a volume of 3 mL of CM2G medium supplemented with kanamycin (25 mg/L), and cultivated in a test tube upon shaking (120 rpm) at 30° C. for 16 hours. The composition of CM2G medium is as follows:

CM2G:

| | |
|---|---|
| Glucose | 5 g/L |
| Polypeptone | 10 g/L |
| Yeast extract | 10 g/L |
| NaCl | 5 g/L |

Adjusted to pH 7.0 with KOH

The obtained culture (200 µL) is inoculated in a volume of 4 mL of MMTG medium supplemented with kanamycin (25 mg/L), and cultivated in a test tube upon shaking (120 rpm) at 30° C. for 112 hours. The MMTG medium was prepared from the Components A, B and C:

Component A:

| | |
|---|---|
| Glucose | 120 g/L |
| $MgSO_4 \cdot 7H_2O$ | 3 g/L |
| $FeSO_4 \cdot 7H_2O$ | 0.03 g/L |
| $MnSO_4 \cdot 5H_2O$ | 0.03 g/L |

Component B:

| | |
|---|---|
| $(NH_4)_2SO_4$ | 30 g/L |
| $KH_2PO_4$ | 1.5 g/L |
| Bean lysate (TN) | 0.2 g/L |
| Thiamine hydrochloride | 450 µg/L |
| Biotin | 450 µg/L |
| DL-methionine | 0.15 g/L |

Component C:

| | |
|---|---|
| $CaCO_3$ | 50 g/L |

The A, B, and C components are sterilized separately and mixed just before cultivation. After the cultivation, cells are precipitated by centrifugation at 8,000 rpm, and culture supernatant is collected.

5.2. SDS-PAGE Analysis of Protein

A standard procedure was used for analysis of proteins (Laemmli U.K. et al., Form-determining function of the genes required for the assembly of the head of bacteriophage T4, *J. Mol. Biol.*, 1970, 49:99-113). Polyacrylamide gels were stained with CBB Stain One (Nacalai Tesque) or SYPRO® Ruby protein gel stain (Invitrogen). Visualization of the fluorescently-labeled proteins or proteins stained with SYPRO® Ruby protein gel stain was performed with Gel Ninja (Oriental Instruments, major wavelength: 500 nm).

For reducing-condition SDS-PAGE, a protein solution was incubated at 95° C. for 1 minute and then mixed with 2×Laemmli Sample Buffer (BIO RAD) and 10×NuPAGE® Sample Reducing Agent (Invitrogen) in a ratio of 4:5:1. The mixture was incubated at 98° C. for 5 minutes, and the resultant sample was subjected to SDS-PAGE.

For non-reducing-condition SDS-PAGE, a protein solution, 2×Laemmli Sample Buffer (BIO RAD) and ultra-pure water were mixed in a ratio of 4:5:1, and the resultant sample was subjected to SDS-PAGE.

5.3. Western Blotting Analysis of Proteins

Proteins in the polyacrylamide gel obtained by SDS-PAGE according to the method described in Example 5.2 were transferred to PVDF (polyvinylidene difluoride) membrane. The resultant PVDF membrane was immersed with shaking for 1 hour or more in TTBS (20 mM Tris-HCl pH 7.6, 500 mM NaCl, 0.2% Tween 20) supplemented with 2% skim milk. Then, a 1/1000 volume of Streptavidin-Alkaline phosphatase (R&D Systems) was added to TTBS (20 mM Tris-HCl pH7.6, 500 mM NaCl, 0.2% Tween 20) supplemented with 2% skim milk, and the PVDF membrane was left with shaking in the solution for 1 hour. Then, the PVDF membrane was immersed in 1-Step™ NBT/BCIP (Thermo Scientific) and alkaline phosphatase activity was detected.

5.4. Purification of the FabHL

The culture supernatant (120 mL), in which FabHL was secreted and expressed, was applied to an affinity chromatography column HiTrap ProteinG HP (GE Healthcare, CV of 5 mL, used in tandem) equilibrated with 20 mM Tris-HCl pH 8.0. The not adsorbed by the carrier proteins (non-adsorbed proteins) were washed out with 20 mM Tris-HCl pH 8.0. The adsorbed proteins were eluted with 0.1 M glycine pH 2.7. The 1-mL fractions were each collected in 96-deep well plate, the every well of which contained 40 µL of 2 M Tris-HCl pH 8.5. The resultant fractions were analyzed with non-reducing-condition SDS-PAGE according to the method described in Example 5.2.

The FabHL-containing fraction in a total volume of 11 mL was collected and mixed with ultra-pure water (100 mL). A solution of sodium acetate (50%, w/v) was added to adjust pH to 5. The mixture was equally divided and applied onto an ion-exchange chromatography column RESOURCE S (GE Healthcare, CV of 6 mL) equilibrated with 20 mM sodium acetate pH 5.0. The non-adsorbed proteins were washed out initially with 20 mM sodium acetate pH 5.0 and finally with 20 mM sodium dihydrogen phosphate pH 6.0. The adsorbed proteins were eluted under linear gradient of 20 mM disodium hydrogen phosphate pH 8.0 in a range from 0 to 100%, in a total volume of 120 mL. The resultant fractions were analyzed with non-reducing-condition SDS-PAGE according to the method described in Example 5.2. The FabHL protein was obtained from the fractions corresponding to 30-100% of 20 mM disodium hydrogen phosphate pH 8.0.

Fractions containing FabHL were collected and concentrated with Amicon Ultra-15 10 kDa (Millipore). The resultant concentrate was applied onto a gel filtration chromatography column HiLoad 16/60 Superdex 200 pg (GE Healthcare, CV of 120 mL) equilibrated with 50 mM Tris-HCl pH 8.0, 200 mM NaCl and 1 mM EDTA pH 8.0, and eluted with the same buffer at a flow rate of 0.8 mL/min. The resultant fractions were analyzed with non-reducing-condition SDS-PAGE according to the method described in Example 5.2. The FabHL protein was obtained from the fractions corresponding to CV of 0.72. Fractions containing FabHL were collected, concentrated and ultrafiltrated with Amicon Ultra-15 10 kDa (Millipore) to replace the buffer with 20 mM Tris-HCl pH 7.6. The obtained solution was used as a FabHL solution.

5.5. Purification of the FabH-$_{TGC}$-Int7-HT-FabL

The culture supernatant, in which FabH-$_{TGC}$-Int7-HT-FabL was secreted and expressed, was concentrated and ultrafiltrated with Amicon Ultra-15 10 kDa (Millipore) to replace the buffer with 20 mM Tris-HCl pH 7.6, 300 mM NaCl and 10 mM imidazole. This solution was applied onto an affinity chromatograph column His TALON superflow 5 mL Cartridge (Clontech) equilibrated with 20 mM Tris-HCl pH 7.6, 300 mM NaCl and 10 mM imidazole. The non-adsorbed proteins were washed out with 20 mM Tris-HCl pH 7.6, 300 mM NaCl and 10 mM imidazole. The adsorbed proteins were eluted with 20 mM Tris-HCl pH 7.6, 300 mM NaCl and 150 mM imidazole. The resultant fractions were analyzed with non-reducing-condition SDS-PAGE according to the method described in Example 5.2. To perform purification, the quantity of linked columns was varied depending on the volume of the culture supernatant.

Fractions containing FabH-$_{TGC}$-Int7-HT-FabL were collected and concentrated with Amicon Ultra-15 10 kDa (Millipore). The resultant concentrate was applied onto a gel filtration chromatography column HiLoad 16/60 Superdex 200 pg (GE Healthcare, CV of 120 mL) equilibrated with 50 mM Tris-HCl pH 8.0, 200 mM NaCl and 1 mM EDTA pH 8.0, and eluted with the same buffer at a flow rate of 0.8 mL/min. The resultant fractions were analyzed with non-reducing-condition SDS-PAGE according to the method described in Example 5.2. The FabH-$_{TGC}$-Int7-HT-FabL protein was obtained from the fractions corresponding to CV of 0.6. Fractions containing FabH-$_{TGC}$-Int7-HT-FabL were collected, concentrated and ultrafiltrated with Amicon Ultra-15 10 kDa (Millipore) to replace the buffer with 20 mM Tris-HCl pH 7.6. The obtained solution was used as a FabH-$_{TGC}$-Int7-HT-FabL solution.

5.6. Thiolysis of the FabH-$_{TGC}$-Int7-HT-FabL and Ligation to Cys-Lys (Biotin)

Figure 32:
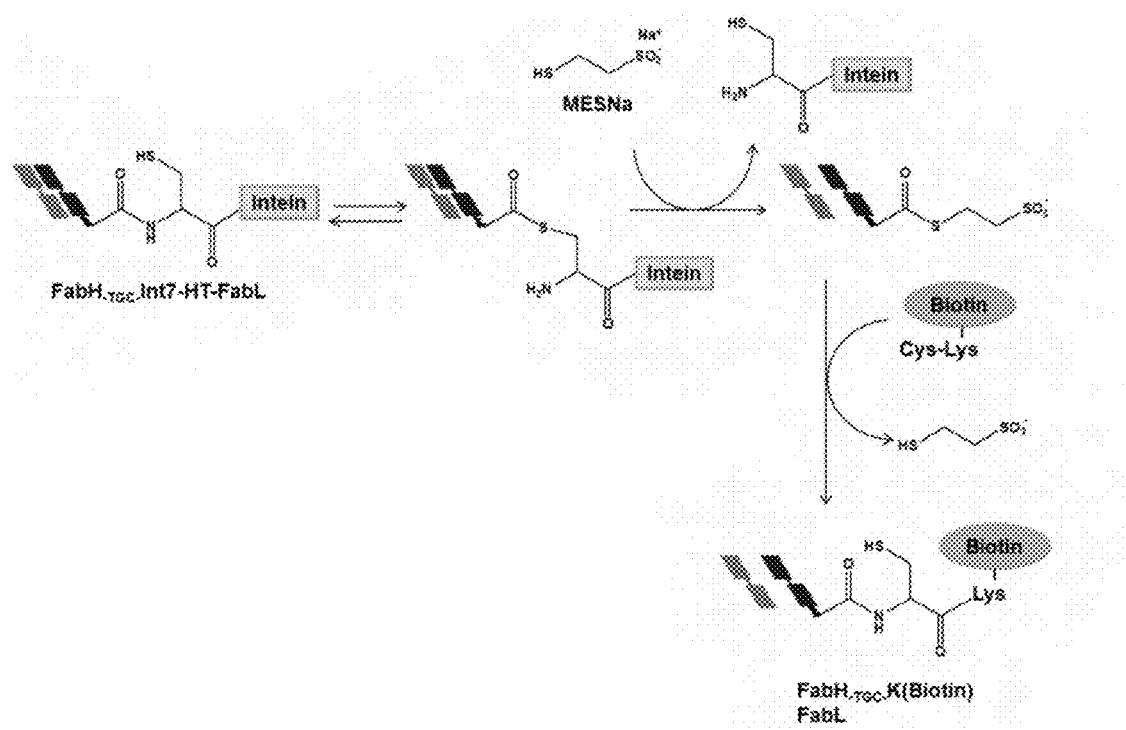
FIG. 32 shows the scheme for cleavage of intein from FabH-$_{TGC}$-Int7-HT-FabL and ligation of FabH to Cys-Lys (Biotine).
Figure 33:
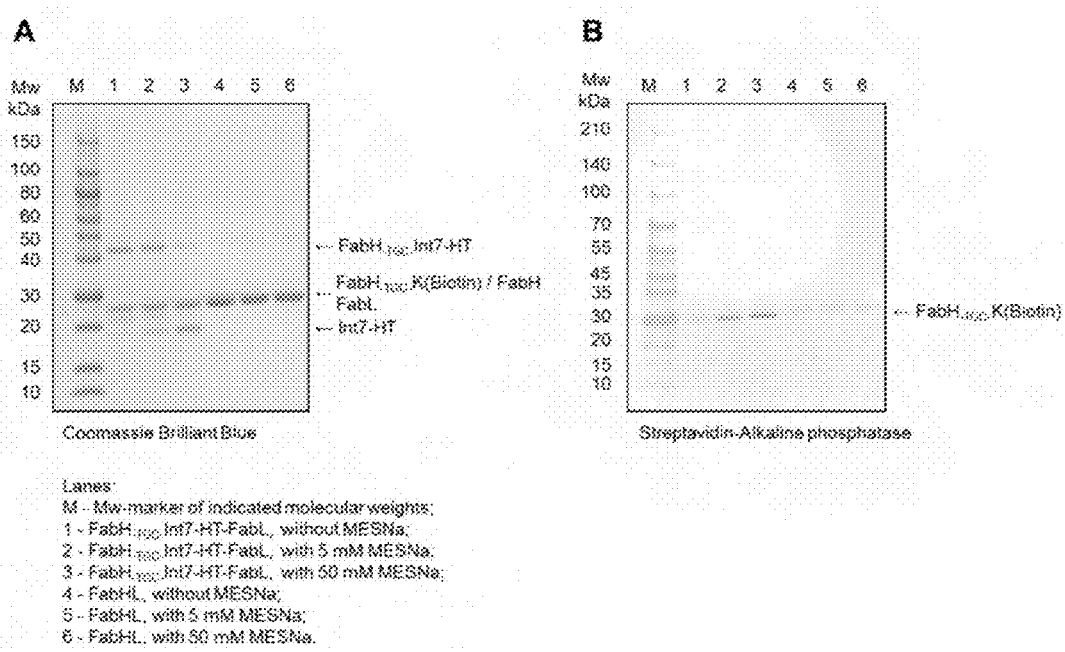
FIG. 33 shows the SDS-PAGE and Western blotting analysis of thiolysis of FabH-$_{TGC}$-Int7-HT-FabL and ligation to Cys-Lys(Biotin) under various concentrations of MESNa (photograph).

The FabH-$_{TGC}$-Int7-HT-FabL protein solution was added to a reaction mixture {100 mM Tris-HCl pH 7.0, 500 mM NaCl, 1 mM EDTA pH 8.0, 1 mM TCEP (tris(2-carboxyethyl)phosphine) pH 8.0, 0 or 5 or 50 mM MESNa pH 7.0 and 5 mM Cys-Lys(Biotin) (also abbreviated as Cys-Lys (Biot)-NH$_2$, see Auxiliary example 2)} to a final concentration of FabH-$_{TGC}$-Int7-HT-FabL 150 µg/mL and reacted in a volume of 50 µL at 37° C. for 14 hours. As a control experiment, the FabHL protein solution was added to the same reaction mixture to a final concentration of 150 µg/mL and reacted under the same condition. The reaction scheme is shown on FIG. 32. After the reaction, the reaction mixture was ultrafiltrated with Amicon Ultra-0.5 3 kDa (Millipore) to replace the buffer with 20 mM Tris-HCl pH 7.6. The reducing-condition SDS-PAGE and the Western blotting analysis were performed according to the methods described in Examples 5.2 and 5.3. The cleavage of intein from FabH-$_{TGC}$-Int7-HT-FabL and ligation of FabH to Cys-Lys (Biotin) were observed under various concentrations of MESNa (FIG. 33).

Figure 34:
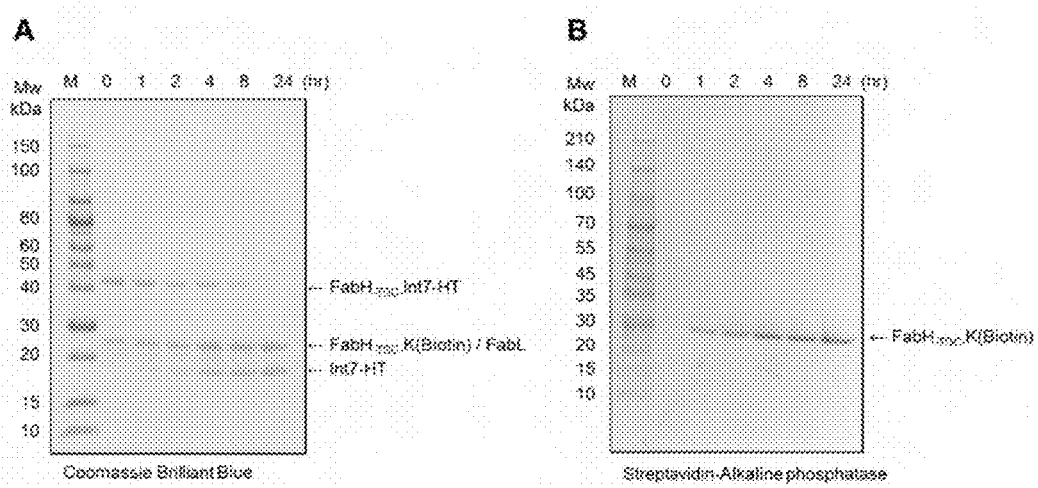
FIG. 34 shows the SDS-PAGE and Western blotting analysis of thiolysis of FabH-$_{TGC}$-Int7-HT-FabL and ligation to Cys-Lys(Biotin) under various times of thiolysis (photograph).

The FabH-$_{TGC}$-Int1-HT-FabL solution was added to a reaction mixture {100 mM Tris-HCl (pH7.0), 500 mM NaCl, 1 mM EDTA (pH8.0), 5 mM TCEP (pH8.0), 50 mM MESNa (pH7.0), 5 mM Cys-Lys(Biot)-NH$_2$} to a final concentration FabH-$_{TGC}$-Int7-HT-FabL 150 µg/ml and reacted in a volume of 250 µl at 37° C. At each of specified time points, sampling was performed and the sampled reaction mixture was ultrafiltrated with Amicon Ultra-0.5 3 kDa (Millipore) to replace the buffer with 20 mM Tris-HCl (pH7.6). The reducing-condition SDS-PAGE and the Western blotting analysis were performed according to the methods described in Examples 5.2 and 5.3. The time-dependent cleavage of intein and ligation of FabH to Cys-Lys(Biot)-NH$_2$ were observed (FIG. 34).

5.7. Thiolysis of the FabH-$_{TGC}$-Int7-HT-FabL, Ligation to Cys-CH$_2$CH$_2$CH$_2$N$_3$ and Reaction with Dibenzocyclooctyne-Fluor 488

Figure 35:
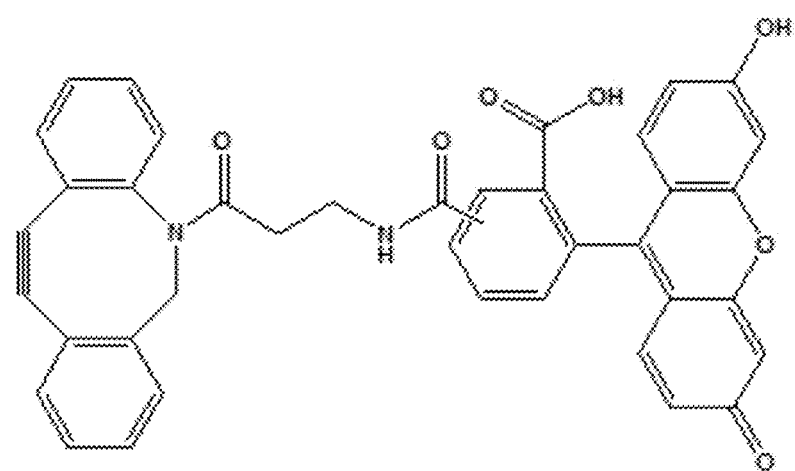
FIG. 35 shows the chemical structure of dibenzocyclooctyne-fluor 488.
Figure 36:
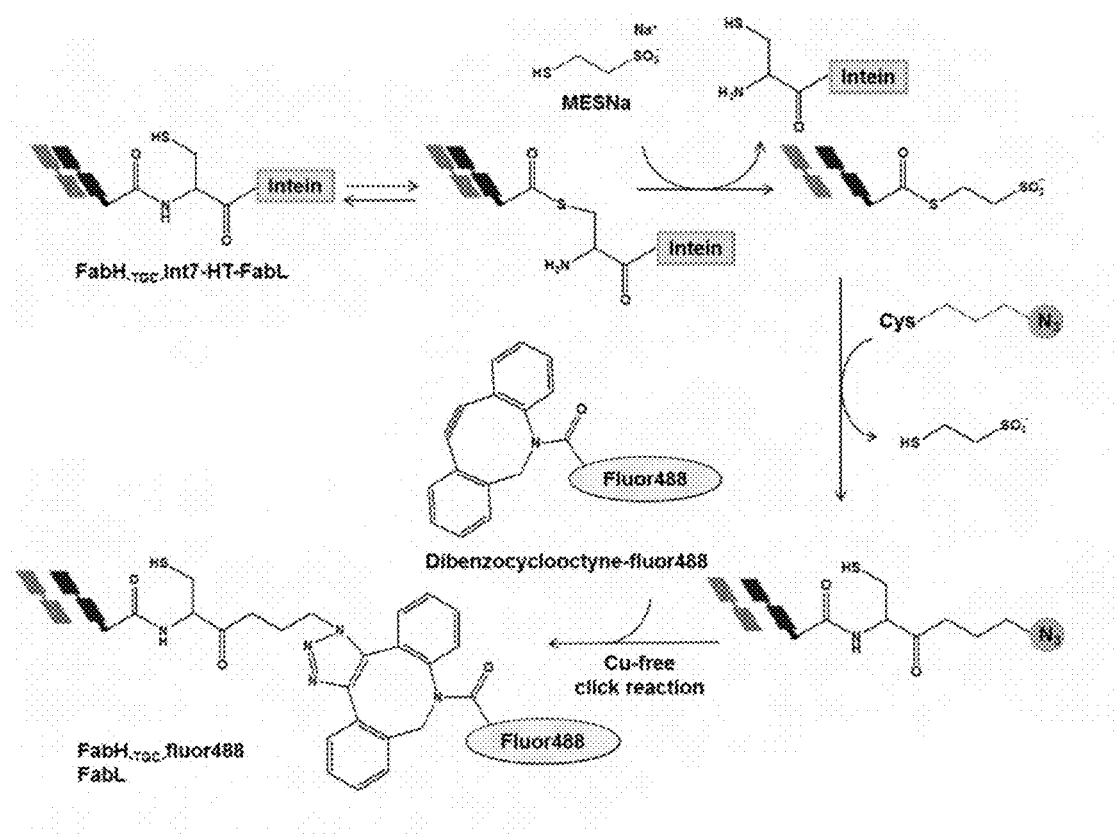
FIG. 36 shows the scheme for cleavage of intein from FabH-$_{TGC}$-Int7-HT-FabL, ligation to Cys-CH$_2$CH$_2$CH$_2$N$_3$ and reaction with dibenzocyclooctyne-fluor 488.
Figure 37:
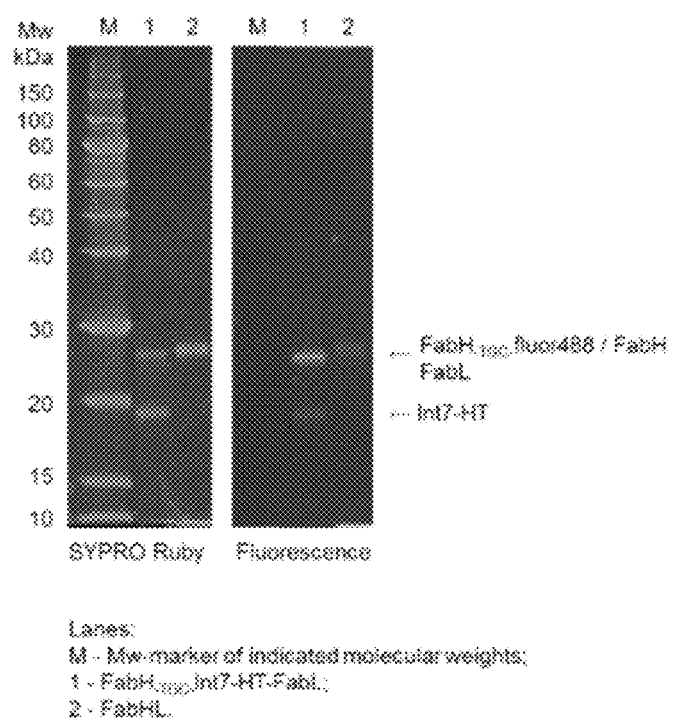
FIG. 37 shows the SDS-PAGE, Western blotting and fluorescent analysis of thiolysis of FabH-$_{TGC}$-Int7-HT-FabL, ligation to Cys-CH$_2$CH$_2$CH$_2$N$_3$ and reaction with dibenzocyclooctyne-fluor 488 (photograph).

The FabH-$_{TGC}$-Int7-HT-FabL protein solution was added to a reaction mixture {100 mM Tris-HCl pH 7.0, 500 mM NaCl, 1 mM EDTA pH 8.0, 1 mM TCEP pH 8.0, 50 mM MESNa pH 7.0 and 5 mM Cys-CH$_2$CH$_2$CH$_2$N$_3$ (see Auxiliary example 3)} to a final concentration of FabH-$_{TGC}$-Int7-HT-FabL 150 µg/mL and reacted in a volume of 100 µL at 37° C. for 42 hours. As a control experiment, the FabHL protein solution was added to a final concentration of 150 µg/mL and reacted under the same condition. The reaction scheme is shown on FIG. 36. After thiolysis and ligation, the reaction mixture was ultrafiltrated with Amicon Ultra-0.5 3 kDa (Millipore) to replace the buffer with 20 mM Tris-HCl pH 7.6. An aliquote (20 µL) of the obtained solution was mixed with sodium phosphate buffer pH 7.0 (final concentration 100 mM) and dibenzocyclooctyne-fluor 488 (Sigma Aldrich, FIG. 35) (final concentration 1 mM). The copper-free click reaction was conducted in a volume of 25 µL at 25° C. for 16 hours with shading. The reducing-condition SDS-PAGE was performed according to the method described in Example 5.2. The cleavage of intein from FabH-$_{TGC}$-Int7-HT-FabL, ligation of FabH to Cys- CH₂CH₂CH₂N₃ and reaction of the ligation product with dibenzocyclooctyne-fluor 488 was observed (FIG. 37).

Auxiliary Example 1

Construction of *C. glutamicum* Deficient in Penicillin-Binding Protein PBP1a

Construction of Vector pBSΔCgl0278 for Deleting Cgl0278 Gene Encoding PBP1a

The genome sequence of *C. glutamicum* ATCC13032 and the nucleotide sequence of the Cgl0278 gene encoding the penicillin-binding protein PBP1a have already been determined (GenBank accession BA000036 (version BA000036.3 GI: 42602314, locus_tag=«NCgl0274»). With reference to this sequence, the primers P27 (SEQ ID NO: 61), P28 (SEQ ID NO: 62), P29 (SEQ ID NO: 63), and P30 (SEQ ID NO: 64) were synthesized. By PCR using the chromosomal DNA of the *C. glutamicum* ATCC13869 strain prepared in a conventional manner (Saito H. and Miura K. I., *Biochim. Biophys. Acta,* 1963, 72:619-629) as a template, and the primers of P27 and P28, and P29 and P30, about 1 kbp of 5' side upstream region and about 1 kbp of 3' side downstream region of Cgl0278 encoding PBP1a were amplified, respectively. Then, by PCR using both the amplified DNA fragments as a template and primers P27 and P30, a DNA fragment of about 2 kbp consisting of both the fragments fused to each other was obtained. In the primers P27 and P30, recognition sequences for the restriction enzymes BamHI and XbaI were designed, respectively. For PCR, Pyrobest DNA Polymerase (produced by Takara Bio) was used, and the reaction conditions were those of the protocol recommended by the manufacturer. This DNA fragment was treated with the restriction enzymes BamHI and XbaI, and inserted into the BamHI-XbaI site of pBS4 described in WO2005/113744 to obtain a vector pBSΔCgl0278 for deleting the Cgl0278 gene. For the ligation reaction, DNA Ligation Kit Ver. 2.1 (produced by Takara Bio) was used, and the reaction conditions were those of the protocol recommended by the manufacturer.

Construction of PBP1a-Deficient Strain

The *C. glutamicum* YDK010 strain described in WO2004/029254 was transformed with the constructed vector pBSΔCgl0278. The *C. glutamicum* YDK010 strain is a cell surface layer protein PS2 deficient strain of the *C. glutamicum* AJ12036 strain (FERM BP-734) (WO2004/029254). Strain was selected from the obtained transformants according to the methods described in WO2005/113744 and WO2006/057450 to obtain YDK010ΔPBP1a strain deficient in the Cgl0278 gene.

Auxiliary Example 2

Synthesis of Cys-Lys(Biotin)

The biotin-labeled peptide Cys-Lys(Biotin) (also abbreviated as Cys-Lys(Biot)-NH₂) was chemically synthesized using ordinary methods according to the scheme shown on FIG. 38.

Auxiliary Example 3

3.1. Synthesis of Boc-Cys(Trt)-CH₂CH₂CH₂N₃

Figure 39:
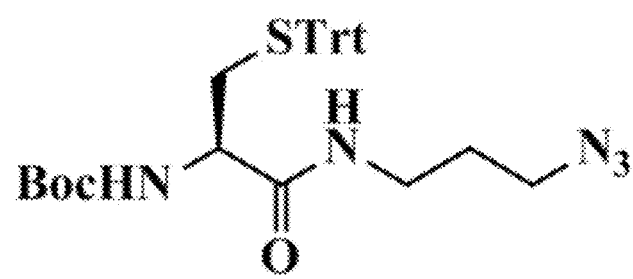
FIG. 39 shows the chemical structure for Boc-Cys(Trt)-CH$_2$CH$_2$CH$_2$N$_3$.

To a solution of Boc-Cys(Trt)-OH 1.39 g (3.0 mmoL) in dichloroethane (28 mL), 3-azido-1-propanamine 0.36 g (3.6 mmoL), 1-hydroxy-7-azabenzotriazole 0.52 g (3.8 mmoL), triethylamine 300 μL, and EDC-HCl salt (1-ethyl-3-[3-dimethylaminopropyl]carbodiimide hydrochloride) 0.73 g (3.8 mmoL) were added. The mixture was stirred at room temperature for 75 hours. The obtained reaction mixture was washed twice with saturated aqueous ammonium chloride solution (20 mL), and the organic phase was collected and concentrated. The resultant oil was purified using liquid column chromatography (column: 20 cm×3 cm I.D.; mobile phase: dichloromethane and methanol as 25:1, v/v; isocratic elution was applied.). Thus Boc-Cys(Trt)-CH₂CH₂CH₂N₃ was obtained (1.64 g, 3.0 mmoL; FIG. 39).

3.2. Synthesis of Cys-CH₂CH₂CH₂N₃

Figure 40:
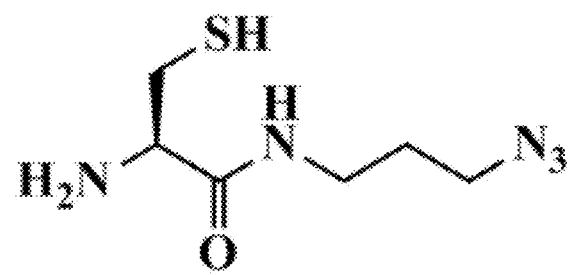
FIG. 40 shows the chemical structure for Cys-CH$_2$CH$_2$CH$_2$N$_3$.

To a mixture of trifluoroacetate (30 mL), triisopropylsilane (0.8 mL), and water (0.8 mL), Boc-Cys(Trt)-CH₂CH₂CH₂N₃ 1.64 g (3.0 mmoL) was added. The mixture was stirred at room temperature for 2 hours. After the solvent was evaporated under reduced pressure, dichloromethane (30 mL) and water (30 mL) were added to separate organic and aqueous layers. The aqueous phase was collected and washed with dichloromethane (30 mL) three times. The resultant aqueous phase was concentrated under reduced pressure, diluted with 0.05% (w/v) trifluoroacetate aqueous solution (10 mL), and purified using preparative liquid chromatography (column: Hydrosphere C18, 25 cm×2 cm I.D.; mobile phase: from 0.05% (v/v) TFA in H₂O to 0.05% (v/v) TFA in CH₃CN; linear gradient from 0%-50% CH₃CN with 0.05% TFA over 30 min; flow rate: 8 mL/min). The fractions containing Cys-CH₂CH₂CH₂N₃ were collected and lyophilized. Thus Cys-CH₂CH₂CH₂N₃ was obtained (0.46 g, 2.3 mmoL; FIG. 40).

¹H NMR (400 MHz, DMSO-d⁶): δ 1.68-1.72 (m, 2H), δ 2.89-2.93 (m, 2H), δ 3.10-3.30 (m, 2H), δ 3.35-3.45 (m, 2H), δ 3.88-3.92 (m, 1H), δ 8.15-8.35 (bs, 2H), δ 8.50-8.55 (m, 1H), δ 8.60-8.70 (bs, 1H).

While the invention has been described in detail with reference to preferred embodiments thereof, it will be apparent to one skilled in the art that various changes can be made, and equivalents employed, without departing from the scope of the invention. All the cited references herein are incorporated by reference as a part of this application.

TABLE 1

| Strain/Plasmid | Description | Reference |
| --- | --- | --- |
| pPK4 | Expression shuttle-vector | U.S. Pat. No. 6,090,597 A |
| pEXC1 | Expression shuttle-vector constructed by cloning the KpnI-EXC1-BamHI expression cassette (EXC1 contains promoter PS2 (cspB), multi-cloning site, and terminator of nusG gene) into pPK4/KpnI-BamHI vector. | This work |
| pEXC1-exe-MAG | The DNA-fragment containing the exenatide-MAG fusion gene was cloned into pEXC1 vector. | |
| pEXC1-exe-MAG-HT#2 | The C-terminus-His₆-tagged exenatide-MAG fusion gene cloned into pEXC1 vector. | |
| TG1 | *E. coli* supE hsdΔ5thi Δ(lac-proAB)F' [traD36 proAB⁺lacIᵍlacZΔM15] | Gibson, T. J. (1984) Studies on the Epstein-Barr virus genome. Ph. D. thesis, University of Cambridge, UK. |

TABLE 1-continued

| Strain/Plasmid | Description | Reference |
|---|---|---|
| JM109 | E. coli F (traD36, proAB+ lacIq, (lacZ)M15) endA1 recA1 hsdR17(rk −, mk+) mcrA supE44 λ− gyrA96 relA1(lac-proAB) thi-1 | Promega, catalog No. P9751 |
| YDK010 | C. glutamicum strain | WO2004/029254 |
| YDK010 [pEXC1] YDK010 [pEXC1-exe-MAG] YDK010 [pEXC1-exe-MAG-HT#2] | YDK010 harbouring plasmid designated in brackets. | This work |

TABLE 2

| Strain/Plasmid | Description | Reference |
|---|---|---|
| *Auxiliary plasmids* | | |
| pPKSherFabHL | Expression shuttle-vector harboring genes encoding trastuzumab Fab heavy chain (H) and light chain (L) (FabHL). | This work |
| pEXC1 | Expression shuttle-vector | This work |
| pEXC1-exe-MAG-HT#2 | The C-terminus-His$_6$-tagged exenatide-MAG fusion gene cloned into pEXC1 vector. | This work |
| pPKSherFabHL-XbaI/NheI | Auxiliary plasmid for cloning FabHL-G-MAG fusion gene. | This work |
| *Plasmids harboring genes encoding inteins* | | |
| pUC57-MAG pUC57-Int4 pUC57-Int5 pUC57-Int7 pUC57-iBLA(Int18) pUC57-iEKD(Int19) | Standard E. coli vector harboring chemically synthesized genes encoding Inteins MAG, Int4, Int5, Int7, Int18, and Int19. | ATG Service Gene |
| *Inteins fused with FabL (Trastuzumab)* | | |
| pPKSherFabH-FabL-$_{CGC}$-MAG-HT pPKSherFabH-FabL-$_{CGC}$-MAG pPKSherFabH-FabL-$_{CGC}$-Int4 pPKSherFabH-FabL-$_{CGC}$-Int5 pPKSherFabH-FabL-$_{CGC}$-Int7 | Shuttle-vectors harboring genes encoding trastuzumab Fab heavy chain (H) (FabH) and light chain (L) (FabL) fused with an intein or a His6-tagged (HT) intein through the Cys-Gly-Cys (CGC) linker. | This work |
| *Inteins fused with FabH (Trastuzumab)* | | |
| pPKSherFabH-$_{TGC}$-MAG-HT-FabL pPKSherFabH-$_{TGC}$-MAG-FabL pPKSherFabH-$_{TGC}$-Int4-HT-FabL pPKSherFabH-$_{TGC}$-Int5-HT-FabL pPKSherFabH-$_{TGC}$-Int7-HT-FabL pPKSherFabH-$_{TGC}$-Int18-HT-FabL pPKSherFabH-$_{TGC}$-Int19-HT-FabL | Shuttle-vectors harboring genes encoding trastuzumab Fab heavy chain (H) (FabH) fused with an intein or a His6-tagged (HT) intein through the Thr-Gly-Cys (TGC) linker and light chain (L) (FabL). | This work |

TABLE 3

| Strain/Plasmid | Description | Reference |
|---|---|---|
| YDK010 | C. glutamicum strain | WO2004/029254 |
| YDK010ΔPBP1a | C. glutamicum strain modified so that activity of a penicillin-binding protein is reduced | This work |
| YDK010ΔPBP1a [pPKSherFabH-$_{TGC}$-IntX(HT)-FabL]; X = 4, 5, 7, 18 or 19, or IntX = MAG, if X = 1 | All constructed plasmids were introduced into YDK010ΔPBP1a strain using electroporation | This work |
| YDK010ΔPBP1a [pPKSherFabH-FabL-$_{CGC}$-IntX(HT)]; X = 4, 5, 7, 18 or 19, or IntX = MAG, if X = 1 | All constructed plasmids were introduced into YDK010ΔPBP1a strain using electroporation | This work |

TABLE 4

| Intein | Primer PR1 | Primer PR2 | Template DNA | Time T1 (min:sec) | Time T2 (min:sec) |
|---|---|---|---|---|---|
| MAG | P4 | P5 | pUC57-MAG | 1:30 | 5:00 |
| MAG-HT | P3 | P6 | pPKSherFabH-$_{TGC}$-MAG-FabL | 5:00 | — |
| Int4-HT | P7 | P8 | pUC57-Int4 | 2:00 | 5:00 |
| Int5-HT | P9 | P10 | pUC57-Int5 | 2:00 | 5:00 |
| Int7-HT | P11 | P12 | pUC57-Int7 | 2:00 | 5:00 |
| Int18-HT | P13 | P15 | pUC57-iBLA(Int18) | 1:30 | 5:00 |
| Int19-HT | P14 | P15 | pUC57-iEKD(Int19) | 1:30 | 5:00 |

TABLE 5

| Intein | Primer PR3 | Primer PR4 | Template DNA | Time T3 (min:sec) | Time T4 (min:sec) |
|---|---|---|---|---|---|
| MAG | P19 | P20 | pEXC1-exe-MAG | 1:30 | 4:00 |
| Int4 | P21 | P22 | pUC57-Int4 | 1:30 | 4:20 |
| Int5 | P23 | P24 | pUC57-Int5 | 1:30 | 4:20 |
| Int7 | P25 | P26 | pUC57-Int7 | 1:30 | 4:20 |

TABLE 6

| Intein | Name/Prototype allele* | Abbreviation | Source |
|---|---|---|---|
| MAG | Mmag Magn8951 BIL | MAG | *Magnetospirillum magnetotacticum* MS-1 |
| Int4 | Pvu PRP8 | PVU | *Penicillium vulpinum* |
| Int5 | Aha DnaE-n | SSP | *Aphanothece halophytica* |
| Int7 | Pab Pol-II | PAB | *Pyrococcus abyssi* |
| Int18 | /Mmag Magn8951 BIL | iBLA | *Brevibacillus laterosporus* LMG 15441 |
| Int19 | /Mmag Magn8951 BIL | iEKD | *Uncultured bacterium* |

*Inteins' Names/Prototypes alleles are given in accordance with the intein database InBase (tools.neb.com/inbase/list.php).

TABLE 7 iBLA
Wall-associated protein [*Brevibacillus laterosporus* LMG 15441]
Sequence ID: ref|ZP_08642447.1|Length: 1897 Number of Matches: 1
Range 1: 1664 to 1795
Alignment statistics for match # 1

| Score | Expect | Method | Identities | Positives | Gaps | Frame |
|---|---|---|---|---|---|---|
| 54.7 bits (130) | 2e−06 | Composition-based stats | 51/151 (34%) | 73/151 (48%) | 30/151 (19%) | |

```
Query    1 CFVAGTPVRMADGSEKAIETVEIGEQV-QGTDGT----INEVIGFGRPRLDGRRLYALNS    55
           CF AGT V + D  EK IE +E+G++V   +D T      EV+G  + + D  ++Y ++
Sbjct 1664 CFTAGTKV-LTDEGEKPIEEIEVGDKVLSKSDETGVVAYKEVVGLFQKQSD--QIYNVHV 1720

Query   56 LD--FFVTADHPFLTSG-GWKSLDPDVTNRINPALNVTQLVIGDTLITVGGP-VDLRSIE  111
           D    TA+HPF  G GW               V L +GD L++  G + +  IE
Sbjct 1721 GDEVLEATAEHPFWVDGKGWTF-------------VKDLKVGDLLVSSSGTTLAIEKIE 1766

Query  112 SQDAPAETVVYNLHLIGNNTYVAS--GYYVH                             140 (SEQ ID NO: 37)
              AP ET VYN +   N+Y  S  G +VH
Sbjct 1767 K--APRETTVYNFEVKDFNSYFVSNLGIWVH                             1795 (SEQ ID NO: 41)
```

TABLE 8 iEKD
Hypothetical protein ACD_65C00277G0001, partial [uncultured bacterium]
Sequence ID: gb|EKD47815.1| Length: 1180 Number of Matches: 1
Range 1: 655 to 783
Alignment statistics for match # 1

| Score | Expect | Method | Identities | Positives | Gaps | Frame |
|---|---|---|---|---|---|---|
| 47.0 bits (110) | 0.001 | Composition-based stats | 41/142 (29%) | 67/142 (47%) | 15/142 (10%) | |

```
Query    1 CFVAGTPVRMADGSEKAIETVEIGEQVQGTDGTINEVIGFGRPRLDGRRLYALNSLDFFV   60
           CF  GT + M+DGS K IE + G+ ++        +E++  G         L + + V
Sbjct  655 CFKEGTKILMSDGSYKNIEDIVAGDLIKTRPNEFDEILVTGE---------VLKTYEHVV  705

Query   61 TADHPFLTSGGWKSLDPDVTNRINPALNVTQ-LVIGDTLITVGG-PVDLRSIESQDAPAE  118
           +       +GG   + P+    +N  ++ + L +GD LI + G V + S E+ +AP
Sbjct  706 ST--YISVNGGVLEVTPEHVIFLNDKWSLAENLKVGDYLINMDGEKVWVESAETINAP--  761

Query  119 TVVYNLHLIGNNTYVASGYYVH                                      140 (SEQ ID NO: 37)
           T VYN +   +TY A   YVH
Sbjct  762 TKVYNFEVEKYHTYFADNIYVH                                       783 (SEQ ID NO: 42)
```

TABLE 9

| Intein | Mw (kDa) | IP [1] | Ch [2] (pH 7) | Cys No. [3] | Fab Trastuzumab Light chain (FabL) | Fab Trastuzumab Heavy chain (FabH) |
|---|---|---|---|---|---|---|
| MAG | 15 | 4.61 | −7.7 | 1 | P/A [4] | P |
| Int4 (PVU) | 18 | 4.83 | −10.85 | 1 | nd | P/A |
| Int5 (SSP) | 14 | 4.35 | −13.96 | 2 | P | P |
| Int7 (PAB) | 21 | 4.98 | −10.76 | 1 | P/nt | P/A |
| Int18 (iBLA) | 15 | 4.66 | −9.95 | 1 | nt | P/A |
| Int19 (iEKD) | 15 | 4.64 | −10.87 | 1 | nt | P/A |

[1] IP—isoelectric point;
[2] Chprotein charge at pH 7;
[3] Cys—quantity of cysteine residues in protein;
[4] P—production of a fusion protein was detected in culture broth of the corresponding plasmid strain; A—activity of the fusion protein was detected by using band-shift assay; nd—the fusion protein was not detected in the culture broth; nt—not tested.

TABLE 10

| DNA-fragment | Primer PR5 | Primer PR6 | Template DNA |
|---|---|---|---|
| FabH-$_{TGC}$-Int7-CBD | P31 | P32 | pPKSherFabH-$_{TGC}$-Int7(HT)-FabL |
| FabH-$_{TGC}$-Int18-CBD | | P33 | pPKSherFabH-$_{TGC}$-Int18(HT)-FabL |

The invention claimed is:

1. A coryneform bacterium having an ability to produce a heterologous fusion protein by secretory production, wherein said bacterium has been modified to express a genetic construct that allows for secretory production of the heterologous fusion protein, wherein said genetic construct comprises a DNA encoding at least a heterologous fusion protein, wherein said heterologous fusion protein comprises an extein, and an intein having an activity of acyl rearrangement.

2. The coryneform bacterium according to claim 1, wherein said extein further comprises a target protein.

3. The coryneform bacterium according to claim 2, wherein said extein further comprises a linker, which is linked to the C-terminus of the target protein and is in between the target protein and the intein.

4. The coryneform bacterium according to claim 3, wherein said linker comprises a sequence of one or more amino acid residues.

5. The coryneform bacterium according to claim 4, wherein said linker has a —NH—CH(R1)-CO—NH-CH (R2)-CO— motif at the C-terminus, where R1 and R2 are a side-chain group of a proteinogenic L-amino acid of the same or different kinds.

6. The coryneform bacterium according to claim 5, wherein said R1 is the side-chain group of any proteinogenic L-amino acid or hydrogen, and R2 is the side-chain group of L-cysteine.

7. The coryneform bacterium according to claim 2, wherein said target protein is a heterologous protein for the coryneform bacterium.

8. The coryneform bacterium according to claim 7, wherein said target protein is selected from the group consisting of a bioactive protein, a receptor protein, an antigenic protein, and an enzyme.

9. The coryneform bacterium according to claim 8, wherein said bioactive protein is selected from the group consisting of a growth factor, a hormone, a cytokine, and an antibody-related molecule.

10. The coryneform bacterium according to claim 8, wherein said bioactive protein is an exenatide selected from the group consisting of:
 (A) a protein having the amino acid sequence of SEQ ID NO: 34, and
 (B) a protein having the amino acid sequence of SEQ ID NO: 34, but which includes substitution, deletion, insertion, or addition of one or several amino acid residues, and has an activity of the protein having the amino acid sequence of SEQ ID NO: 34.

11. The coryneform bacterium according to claim 9, wherein said antibody-related molecule is a protein selected from the group consisting of Fab, F(ab')2, an Fc-fusion protein, scFv, and combinations thereof.

12. The coryneform bacterium according to claim 11, wherein said Fab is a trastuzumab Fab having a heavy chain selected from the group consisting of:
 (C) a protein having the amino acid sequence of SEQ ID NO: 35, and
 (D) a protein having the amino acid sequence of SEQ ID NO: 35, but which includes substitution, deletion, insertion, or addition of one or several amino acid residues and has activity according to the amino acid sequence of SEQ ID NO: 35;
 and said trastuzumab Fab has a light chain selected from the group consisting of:
 (E) a protein having the amino acid sequence of SEQ ID NO: 36, and
 (F) a protein having the amino acid sequence of SEQ ID NO: 36, but which includes substitution, deletion, insertion, or addition of one or several amino acid residues and has activity according to the amino acid sequence of SEQ ID NO: 36.

13. The coryneform bacterium according to claim 10, wherein said intein is selected from the group consisting of:
 (G) an amino acid sequence of SEQ ID NO: 37, and
 (H) an amino acid sequence of SEQ ID NO: 37, but which includes substitution, deletion, insertion, or addition of one or several amino acid residues and has activity of acyl rearrangement.

14. The coryneform bacterium according to claim 12, wherein said intein is selected from the group consisting of:
 (I) an amino acid sequence of SEQ ID NO: 38, 40, 41 or 42, and
 (J) an amino acid sequence of SEQ ID NO: 38, 40, 41 or 42, but which includes substitution, deletion, insertion, or addition of one or several amino acid residues and has activity of acyl rearrangement.

15. The coryneform bacterium according to claim 12, wherein said intein is selected from the group consisting of:
 (K) an amino acid sequence of SEQ ID NO: 37, and
 (L) an amino acid sequence of SEQ ID NO: 37, but which includes substitution, deletion, insertion, or addition of one or several amino acid residues and has activity of acyl rearrangement.

16. The coryneform bacterium according to claim 1, wherein said bacterium has been modified further so that activity of a penicillin-binding protein is reduced.

17. The coryneform bacterium according to claim 16, wherein said activity of the penicillin-binding protein is reduced by attenuating expression of a gene encoding the penicillin-binding protein or disrupting the gene.

18. The coryneform bacterium according to claim 17, wherein said penicillin-binding protein is PBP1a or PBP1b.

19. The coryneform bacterium according to claim 18, wherein said penicillin-binding protein is selected from the group consisting of:
(M) an amino acid sequence of SEQ ID NO: 44 or 46, and
(N) a protein having the amino acid sequence of SEQ ID NO: 44 or 46, but which includes substitution, deletion, insertion, or addition of one or several amino acid residues and has activity that if the activity thereof is reduced in the coryneform bacterium, amount of the heterologous fusion protein produced by secretory production is increased compared with that observed for a non-modified strain.

20. The coryneform bacterium according to claim 16, wherein said bacterium has been modified further so that activity of a cell surface layer protein is reduced.

21. The coryneform bacterium according to claim 20, wherein said activity of the cell surface layer protein is reduced by attenuating expression of a gene encoding the cell surface layer protein or disrupting the gene.

22. The coryneform bacterium according to claim 21, wherein said cell surface layer protein is selected from the group consisting of PS1, CspB, and CspA.

23. The coryneform bacterium according to claim 22, wherein said cell surface layer protein is selected from the group consisting of:
(O) an amino acid sequence of SEQ ID NO: 56, 57 or 58, and
(P) a protein having the amino acid sequence of SEQ ID NO: 56, 57 or 58, but which includes substitution, deletion, insertion, or addition of one or several amino acid residues and has activity that if the activity thereof is reduced in the coryneform bacterium, amount of the heterologous fusion protein produced by secretory production is increased compared with that observed for a non-modified strain.

24. The coryneform bacterium according to claim 1, wherein said genetic construct for secretory production of the heterologous fusion protein further comprises a promoter that functions in the coryneform bacterium.

25. The coryneform bacterium according to claim 1, wherein said genetic construct for secretory production of the heterologous fusion protein further comprises a signal peptide that functions in the coryneform bacterium.

26. The coryneform bacterium according to claim 1, wherein said bacterium belongs to the genus *Corynebacterium* or *Brevibacterium*.

27. The coryneform bacterium according to claim 26, wherein said bacterium is *Corynebacterium glutamicum*.

28. A method for producing a heterologous fusion protein by secretory production, comprising:
cultivating the bacterium of claim 1 in a culture medium; and
collecting the heterologous fusion protein produced by secretory production.

29. A method for producing a protein ligated to a substance, comprising:
producing a heterologous fusion protein by the method of claim 28, and
reacting the heterologous fusion protein with a reactant, wherein the reactant comprises the substance, or the method further comprises modifying the reactant with the substance.

30. The method according to claim 29, wherein the heterologous fusion protein comprises a thioester or an ester bond in between the extein and the intein, and said thioester or said ester bond is cleaved by reacting the heterologous fusion protein with a reactant comprising a nucleophilic group selected from amino group, thiol group and hydroxyl group.

31. The method according to claim 29, wherein the heterologous fusion protein comprises a thioester bond in between the extein and the intein, and said thioester bond is cleaved by reacting the heterologous fusion protein with the reactant comprising thiol group.

32. The method according to claim 31, wherein the heterologous fusion protein is reacted with the reactant in the presence of 2-mercaptoethansulfonic acid.

33. The method according to claim 29, wherein the reactant comprises a toxin.

34. The method according to claim 29, wherein the reactant comprises a drug.

35. The method according to claim 29, wherein the reactant comprises a polyethylene glycol, a radioisotope-labeled compound, or a second polypeptide.

36. A method for producing a peptide or a protein, which is amidated at the C-terminus, comprising:
producing a heterologous fusion protein by the method of claim 28, and
reacting the heterologous fusion protein with ammonia or a salt thereof.

37. The method according to claim 36,
wherein the heterologous fusion protein is reacted with ammonia or a salt thereof, in the presence of a compound containing a nucleophilic thiol group.

* * * * *

SEQUENCE LISTING

<160> NUMBER OF SEQ ID NOS: 75

<210> SEQ ID NO 1
<211> LENGTH: 810
<212> TYPE: DNA
<213> ORGANISM: Artificial Sequence
<220> FEATURE:
<223> OTHER INFORMATION: EXC1 DNA-fragment

<400> SEQUENCE: 1

```
ggtacccgct gtgttcctgt gaattagctg atttagtact tttcgggggt gctcattctt    60
accaaagtgt caagttgtgg gtagggtcac ttgaataata attgcaccgc acaggtgata   120
catgcttacc tcctcaagta gcccgaggtt aagtctattt taggtgaaca aatttcagtt   180
tcaggtagaa aactttcgac ctgcttcaga gtttctatta ggaaatctga caccacttga   240
ttaaataacc tacccccgaa ttgggggagg ggttattttt tgctgtgaac gtagttttgg   300
tgcagatgac ctgcgtttat aaagaaatgt aaacgtgatc agatcgatat aaaagaaaca   360
gtttgtactc aggtttgaag cattttctcc gattcgcctg gcaagaatct caattgtcgc   420
ttacagtttt tctcaacgac aggctgctaa gctgctagtt cggtggccta gtgagtggcg   480
tttacttgaa tgaaaagtaa tcccatgtcg tgatcagcca atttgggttg tttccatagc   540
aatccaaagg tttcgtcttt cgatacctat tcaaggagac cctcgcccat atgtttaaca   600
accgtatccg cactgcagct ctcgctggtg caatcgcaat ctccaccgca gcttccggcg   660
tagctatccc agcattcgct caggagacca acccaaccgg cgcctcagat ctacgcgtac   720
tagtgtaagc ggccgcctaa actgcaccac ttaccccgca tttcctaggc cacatataag   780
ggctttggtg atgcgggggtt ttgcggatcc                                    810
```

<210> SEQ ID NO 2
<211> LENGTH: 603
<212> TYPE: DNA
<213> ORGANISM: Artificial Sequence
<220> FEATURE:
<223> OTHER INFORMATION: MAG DNA-fragment

<400> SEQUENCE: 2

```
agatctcagc ggtggtagcg gtggtggcgc cgaaaacctg tacttccagc acggcgaggg    60
aaccttcacg tctgatctgt ctaagcagat ggaggaagag gcagttcgcc tgttcattga   120
gtggctgaaa aatggcggtc cttctagcgg tgcacctccc ccctcctgct cgtcgccgg    180
aactcccgtc cgcatggctg acggcagcga aaggcaatt gaaaccgtgg agattggtga   240
gcaggtccaa gggacggacg gcaccatcaa cgaggttatc ggattcgggc gtccgcgcct   300
cgacgggcgt cggctctatg cgcttaacag tctggatttc ttcgtgacgg cggaccatcc   360
tttcctgacg agcggaggct ggaagtccct cgatccggac gtaaccaacc ggatcaatcc   420
ggccctgaat gtcactcaac ttgtcatcgg tgacaccctg atcaccgtcg gcggcccggt   480
cgatctgcgt tccatcgagt cacaagacgc gcctgccgaa acggtggtct acaacctcca   540
tctaatcggg aacaatacct acgtcgccag cggctattac gtgcattaag cggccgcgaa   600
ttc                                                                  603
```

<210> SEQ ID NO 3
<211> LENGTH: 60
<212> TYPE: DNA
<213> ORGANISM: Artificial Sequence
<220> FEATURE:
<223> OTHER INFORMATION: primer P1

<400> SEQUENCE: 3

```
gaattcgcgg ccgcttagtg gtggtggtgg tgatgcacgt aatagccgct ggcgacgtag    60
```

<210> SEQ ID NO 4
<211> LENGTH: 20
<212> TYPE: DNA
<213> ORGANISM: Artificial Sequence
<220> FEATURE:
<223> OTHER INFORMATION: primer P2

<400> SEQUENCE: 4

```
ctccgattcg cctggcaaga                                                 20
```

<210> SEQ ID NO 5
<211> LENGTH: 663
<212> TYPE: DNA
<213> ORGANISM: Artificial Sequence
<220> FEATURE:
<223> OTHER INFORMATION: Int4 DNA-fragment

<400> SEQUENCE: 5

```
agatctcagc ggtggtagcg gtggtggcgc cgaaaacctg tacttccagc acggcgaggg    60
aaccttcacg tctgatctgt ctaagcagat ggaggaagag gcagttcgcc tgttcattga   120
gtggctgaaa aatggcggtc cttctagcgg tgcacctccc ccctcctgcc tcgctaaggg   180
aacccgtctg ttgcgatacg atgggaccga gatcaacgtc gaggatgtgc gtgaaggtga   240
ccaacttttg ggtcccgatg gagagcctcg ccgtgcattc aacatcgtga gtggtatcga   300
ccgcctgtac cgcgtcaaga tcggcggtga gaaagaagac ctggtagtca cgccgaatca   360
cattctggtg ttttaccgag agggcccctc cgatggtcct gaaaatgcgg aaaggcaaac   420
ggtggagatt actgctgccg agtttgctac cctttctacc gaggaacgaa gcctgtatag   480
tgccttcaca tcccctgcag ttgagaaggg agccgaaggt tcagctgctc aaatgcatag   540
tttcaaggtc gaggacatta gtctcgaatc tgagaagacg gagtgggctg gtttccgagt   600
cgacaaagat cagctttacc tgcgccatga ctaccttgtc ctgcactaag cggccgcgaa   660
ttc                                                                 663
```

<210> SEQ ID NO 6
<211> LENGTH: 552
<212> TYPE: DNA
<213> ORGANISM: Artificial Sequence
<220> FEATURE:
<223> OTHER INFORMATION: Int5 DNA-fragment

<400> SEQUENCE: 6

```
agatctcagc ggtggtagcg gtggtggcgc cgaaaacctg tacttccagc acggcgaggg    60
aaccttcacg tctgatctgt ctaagcagat ggaggaagag gcagttcgcc tgttcattga   120
gtggctgaaa aatggcggtc cttctagcgg tgcacctccc ccctcctgcc tcagttttgg   180
caccgaaatt ttaaccgttg agtacggccc attgcccatt ggcaaaattg tgagtgaaga   240
aattaattgc tctgtgtaca gtgttgatcc agaagggagc gtttacaccc aggcgatcgc   300
ccaatggcat gaccggggag agcaggaagt attggaatat gaattggaag atggttcagt   360
aatccgagct acctctgacc accgcttttt aaccaccgat tatcaactgt tggcgatcga   420
agaaattttt gctaggcaac tggacttgtt gactttagaa aatattaagc aaactgaaga   480
agctcttgac aaccatcgtc ttcccttttcc attacttgac gctgggacaa ttaaataagc   540
```

```
ggccgcgaat tc                                                          552

<210> SEQ ID NO 7
<211> LENGTH: 735
<212> TYPE: DNA
<213> ORGANISM: Artificial Sequence
<220> FEATURE:
<223> OTHER INFORMATION: Int7 DNA-fragment

<400> SEQUENCE: 7
agatctcagc ggtggtagcg gtggtggcgc cgaaaacctg tacttccagc acggcgaggg      60
aaccttcacg tctgatctgt ctaagcagat ggaggaagag gcagttcgcc tgttcattga     120
gtggctgaaa aatggcggtc cttctagcgg tgcacctccc ccctcctgct tcccgggtga     180
tactaggatt ctcgtccaaa tcgatggagt tccacagaag atcactctaa gggagctgta     240
tgagctgttc gaagatgaaa ggtacgaaaa tatggtttac gttaggaaga gcccaagag      300 ggaaattaag gtttattcca ttgacctcga aactggcaaa gttgtattga cggatatcga     360
ggatgtcatc aaggctccgg ccacggatca tttgatcagg ttcgagcttg aagatggaag     420
cagttttgaa accaccgtag atcatccagt tttagtttat gaaaacggca gctttattga     480
gaaaagggcc tttgaagtta aggaggggga taaagtactc gtctctgagc tcgagttagt     540
tgaacaatca agctcgtccc aggataaccc caagaacgag aacttaggtt cccctgagca     600
tgaccaactc ttagagatca agaatatcaa atacgttagc gctaatgatg actttgtgtt     660
ctctcttaat gctaagaaat accataacgt tatcatcaat gagaatattg taacgcatta     720
agcggccgcg aattc                                                      735

<210> SEQ ID NO 8
<211> LENGTH: 453
<212> TYPE: DNA
<213> ORGANISM: Artificial Sequence
<220> FEATURE:
<223> OTHER INFORMATION: Int18 DNA-fragment

<400> SEQUENCE: 8
ttcaaccgcg gtgaatgcgg ctgtttact gccggcacca agtgctaac cgatgaaggc        60 gagaagccga tcgaagaaat tgaagtgggc gataaggtgc tatctaagtc tgacgagacc     120
ggtgtggtcg cgtacaaaga ggtcgtgggg ttgttccaaa aacaatctga ccaaatctac     180
aacgttcacg tcggcgacga ggtgctggaa gctacagcgg aacacccttt ctgggtcgac     240
ggaaaaggtt ggaccttcgt gaaggacctc aaagtcggcg acctcctggt gtcgagttcg     300
ggcaccaccc tcgcgattga aaagatcgaa aaagcacctc gcgaaacgac tgtttacaac     360
ttcgaagtca aggatttcaa ctcctacttc gtgtctaacc ttggcatttg ggttcatcac     420
caccaccacc actaagcggc cgcgctagag tcg                                  453

<210> SEQ ID NO 9
<211> LENGTH: 444
<212> TYPE: DNA
<213> ORGANISM: Artificial Sequence
<220> FEATURE:
<223> OTHER INFORMATION: Int19 DNA-fragment

<400> SEQUENCE: 9
ttcaaccgcg gtgaatgcgg ctgctttaag gaaggaacaa aaatcctgat gtctgatggc      60
agttacaaaa acatcgagga catcgttgcc ggcgatctga ttaaaacccg tccaaatgag     120
ttcgatgaaa tccttgtaac tggcgaagtt ctgaagacct atgaacacgt tgtgtccaca     180
```

```
tacatctccg tgaacggggg cgtcttggaa gttactccag agcacgtaat cttccttaat      240
gataagtggt ccttagccga aaacctcaag gttggggact acctgatcaa tatggatgga      300
gagaaggttt gggtcgagtc cgccgaaaca atcaacgcgc taccaaagt gtacaacttt       360 gaggtggaga ataccacac ctactttgca gataatatct acgttcatca ccaccaccac       420
cactaagcgg ccgcgctaga gtcg                                              444
```

```
<210> SEQ ID NO 10
<211> LENGTH: 40
<212> TYPE: DNA
<213> ORGANISM: Artificial Sequence
<220> FEATURE:
<223> OTHER INFORMATION: primer P3

<400> SEQUENCE: 10
gagctcggta cccaaattcc tgtgaattag ctgatttagt                              40

<210> SEQ ID NO 11
<211> LENGTH: 40
<212> TYPE: DNA
<213> ORGANISM: Artificial Sequence
<220> FEATURE:
<223> OTHER INFORMATION: primer P4

<400> SEQUENCE: 11
tgcatggatc cttaatgcac gtaatagccg ctggcgacgt                              40

<210> SEQ ID NO 12
<211> LENGTH: 70
<212> TYPE: DNA
<213> ORGANISM: Artificial Sequence
<220> FEATURE:
<223> OTHER INFORMATION: primer P5

<400> SEQUENCE: 12
gaaggtggag ccgaagtcct gcgacaagac ccacaccggc tgcttcgtcg ccggaactcc       60
cgtccgcatg                                                              70

<210> SEQ ID NO 13
<211> LENGTH: 55
<212> TYPE: DNA
<213> ORGANISM: Artificial Sequence
<220> FEATURE:
<223> OTHER INFORMATION: primer P6

<400> SEQUENCE: 13
tgcatggatc cttagtggtg gtggtggtga tgcacgtaat agccgctggc gacgt             55

<210> SEQ ID NO 14
<211> LENGTH: 70
<212> TYPE: DNA
<213> ORGANISM: Artificial Sequence
<220> FEATURE:
<223> OTHER INFORMATION: primer P7

<400> SEQUENCE: 14
gaaggtggag ccgaagtcct gcgacaagac ccacaccggc tgcctcgcta agggaacccg       60
tctgttgcga                                                              70

<210> SEQ ID NO 15
<211> LENGTH: 58
<212> TYPE: DNA
```

```
<213> ORGANISM: Artificial Sequence
<220> FEATURE:
<223> OTHER INFORMATION: primer P8

<400> SEQUENCE: 15
tgcatggatc cttagtggtg gtggtggtgg tgcaggacaa ggtagtcatg gcgcaggt         58

<210> SEQ ID NO 16
<211> LENGTH: 70
<212> TYPE: DNA
<213> ORGANISM: Artificial Sequence
<220> FEATURE:
<223> OTHER INFORMATION: primer P9

<400> SEQUENCE: 16
gaaggtggag ccgaagtcct gcgacaagac ccacaccggc tgcctcagtt ttggcaccga       60
aattttaacc                                                             70

<210> SEQ ID NO 17
<211> LENGTH: 54
<212> TYPE: DNA
<213> ORGANISM: Artificial Sequence
<220> FEATURE:
<223> OTHER INFORMATION: primer P10

<400> SEQUENCE: 17
tgcatggatc cttagtggtg gtggtggtgt ttaattgtcc cagcgtcaag taat             54

<210> SEQ ID NO 18
<211> LENGTH: 70
<212> TYPE: DNA
<213> ORGANISM: Artificial Sequence
<220> FEATURE:
<223> OTHER INFORMATION: primer P11

<400> SEQUENCE: 18
gaaggtggag ccgaagtcct gcgacaagac ccacaccggc tgcttcccgg gtgatactag       60
gattctcgtc                                                             70

<210> SEQ ID NO 19
<211> LENGTH: 54
<212> TYPE: DNA
<213> ORGANISM: Artificial Sequence
<220> FEATURE:
<223> OTHER INFORMATION: primer P12

<400> SEQUENCE: 19
tgcatggatc cttagtggtg gtggtggtga tgcgttacaa tattctcatt gatg             54

<210> SEQ ID NO 20
<211> LENGTH: 70
<212> TYPE: DNA
<213> ORGANISM: Artificial Sequence
<220> FEATURE:
<223> OTHER INFORMATION: primer P13

<400> SEQUENCE: 20
gaaggtggag ccgaagtcct gcgacaagac ccacaccggc tgtttactg ccggcaccaa        60 agtgctaacc                                                             70

<210> SEQ ID NO 21
<211> LENGTH: 70
<212> TYPE: DNA
<213> ORGANISM: Artificial Sequence
```

<220> FEATURE:
<223> OTHER INFORMATION: primer P14

<400> SEQUENCE: 21
gaaggtggag ccgaagtcct gcgacaagac ccacaccggc tgctttaagg aaggaacaaa    60
aatcctgatg                                                            70

<210> SEQ ID NO 22
<211> LENGTH: 29
<212> TYPE: DNA
<213> ORGANISM: Artificial Sequence
<220> FEATURE:
<223> OTHER INFORMATION: primer P15

<400> SEQUENCE: 22
tgcatggatc cttagtggtg gtggtggtg                                       29

<210> SEQ ID NO 23
<211> LENGTH: 60
<212> TYPE: DNA
<213> ORGANISM: Artificial Sequence
<220> FEATURE:
<223> OTHER INFORMATION: primer P16

<400> SEQUENCE: 23
gaattcgcgg ccgcttagtg gtggtggtgg tgatgcacgt aatagccgct ggcgacgtag    60

<210> SEQ ID NO 24
<211> LENGTH: 43
<212> TYPE: DNA
<213> ORGANISM: Artificial Sequence
<220> FEATURE:
<223> OTHER INFORMATION: primer P17

<400> SEQUENCE: 24
atgcgctagc agatctcaaa ttcctgtgaa ttagctgatt tag                      43

<210> SEQ ID NO 25
<211> LENGTH: 43
<212> TYPE: DNA
<213> ORGANISM: Artificial Sequence
<220> FEATURE:
<223> OTHER INFORMATION: primer P18

<400> SEQUENCE: 25
gcatgctagc gcggccgctt agcattcacc gcggttgaag gac                      43

<210> SEQ ID NO 26
<211> LENGTH: 46
<212> TYPE: DNA
<213> ORGANISM: Artificial Sequence
<220> FEATURE:
<223> OTHER INFORMATION: primer P19

<400> SEQUENCE: 26
gcatgctagc gcggccgctt aatgcacgta atagccgctg gcgacg                   46

<210> SEQ ID NO 27
<211> LENGTH: 70
<212> TYPE: DNA
<213> ORGANISM: Artificial Sequence
<220> FEATURE:
<223> OTHER INFORMATION: primer P20

<400> SEQUENCE: 27

```
ctccccagtc accaagtcct tcaaccgcgg tgaatgcggc tgcttcgtcg ccggaactcc    60
cgtccgcatg                                                          70

<210> SEQ ID NO 28
<211> LENGTH: 70
<212> TYPE: DNA
<213> ORGANISM: Artificial Sequence
<220> FEATURE:
<223> OTHER INFORMATION: primer P21

<400> SEQUENCE: 28
ctccccagtc accaagtcct tcaaccgcgg tgaatgcggc tgcctcgcta agggaacccg    60
tctgttgcga                                                          70

<210> SEQ ID NO 29
<211> LENGTH: 40
<212> TYPE: DNA
<213> ORGANISM: Artificial Sequence
<220> FEATURE:
<223> OTHER INFORMATION: primer P22

<400> SEQUENCE: 29
cggttgcggc cgcttagtgc aggacaaggt agtcatggcg                          40

<210> SEQ ID NO 30
<211> LENGTH: 70
<212> TYPE: DNA
<213> ORGANISM: Artificial Sequence
<220> FEATURE:
<223> OTHER INFORMATION: primer P23

<400> SEQUENCE: 30
ctccccagtc accaagtcct tcaaccgcgg tgaatgcggc tgcctcagtt ttggcaccga    60
aattttaacc                                                          70

<210> SEQ ID NO 31
<211> LENGTH: 40
<212> TYPE: DNA
<213> ORGANISM: Artificial Sequence
<220> FEATURE:
<223> OTHER INFORMATION: primer P24

<400> SEQUENCE: 31
cggttgcggc cgcttatttaattgtcccag cgtcaagtaa                           40

<210> SEQ ID NO 32
<211> LENGTH: 70
<212> TYPE: DNA
<213> ORGANISM: Artificial Sequence
<220> FEATURE:
<223> OTHER INFORMATION: primer P25

<400> SEQUENCE: 32
ctccccagtc accaagtcct tcaaccgcgg tgaatgcggc tgcttcccgg gtgatactag    60
gattctcgtc                                                          70

<210> SEQ ID NO 33
<211> LENGTH: 40
<212> TYPE: DNA
<213> ORGANISM: Artificial Sequence
<220> FEATURE:
<223> OTHER INFORMATION: primer P26

<400> SEQUENCE: 33
```

```
gcattgcggc cgcttaatgc gttacaatat tctcattgat                              40
```

<210> SEQ ID NO 34
<211> LENGTH: 39
<212> TYPE: PRT
<213> ORGANISM: Heloderma suspectum

<400> SEQUENCE: 34

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 35
<211> LENGTH: 228
<212> TYPE: PRT
<213> ORGANISM: Artificial sequence
<220> FEATURE:
<223> OTHER INFORMATION: Synthesized

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225

<210> SEQ ID NO 36
<211> LENGTH: 214
<212> TYPE: PRT

<213> ORGANISM: Artificial sequence
<220> FEATURE:
<223> OTHER INFORMATION: Synthesized

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 140
<212> TYPE: PRT
<213> ORGANISM: Magnetospirillum magnetotacticum

<400> SEQUENCE: 37

Cys Phe Val Ala Gly Thr Pro Val Arg Met Ala Asp Gly Ser Glu Lys
1               5                   10                  15

Ala Ile Glu Thr Val Glu Ile Gly Glu Gln Val Gln Gly Thr Asp Gly
            20                  25                  30

Thr Ile Asn Glu Val Ile Gly Phe Gly Arg Pro Arg Leu Asp Gly Arg
        35                  40                  45

Arg Leu Tyr Ala Leu Asn Ser Leu Asp Phe Phe Val Thr Ala Asp His
    50                  55                  60

Pro Phe Leu Thr Ser Gly Gly Trp Lys Ser Leu Asp Pro Asp Val Thr
65                  70                  75                  80

Asn Arg Ile Asn Pro Ala Leu Asn Val Thr Gln Leu Val Ile Gly Asp
                85                  90                  95

Thr Leu Ile Thr Val Gly Gly Pro Val Asp Leu Arg Ser Ile Glu Ser
            100                 105                 110

Gln Asp Ala Pro Ala Glu Thr Val Val Tyr Asn Leu His Leu Ile Gly
        115                 120                 125

```
Asn Asn Thr Tyr Val Ala Ser Gly Tyr Tyr Val His
130                 135                 140

<210> SEQ ID NO 38
<211> LENGTH: 161
<212> TYPE: PRT
<213> ORGANISM: Penicillium vulpinum

<400> SEQUENCE: 38

Cys Leu Ala Lys Gly Thr Arg Leu Leu Arg Tyr Asp Gly Thr Glu Ile
1               5                   10                  15

Asn Val Glu Asp Val Arg Glu Gly Asp Gln Leu Leu Gly Pro Asp Gly
                20                  25                  30

Glu Pro Arg Arg Ala Phe Asn Ile Val Ser Gly Ile Asp Arg Leu Tyr
            35                  40                  45

Arg Val Lys Ile Gly Gly Glu Lys Glu Asp Leu Val Val Thr Pro Asn
50                  55                  60

His Ile Leu Val Phe Tyr Arg Glu Gly Pro Ser Asp Gly Pro Glu Asn
65                  70                  75                  80

Ala Glu Arg Gln Thr Val Glu Ile Thr Ala Ala Glu Phe Ala Thr Leu
                85                  90                  95

Ser Thr Glu Glu Arg Ser Leu Tyr Ser Ala Phe Thr Ser Pro Ala Val
            100                 105                 110

Glu Lys Gly Ala Glu Gly Ser Ala Ala Gln Met His Ser Phe Lys Val
        115                 120                 125

Glu Asp Ile Ser Leu Glu Ser Glu Lys Thr Glu Trp Ala Gly Phe Arg
130                 135                 140

Val Asp Lys Asp Gln Leu Tyr Leu Arg His Asp Tyr Leu Val Leu His
145                 150                 155                 160

Ala

<210> SEQ ID NO 39
<211> LENGTH: 123
<212> TYPE: PRT
<213> ORGANISM: Aphanothece halophytica

<400> SEQUENCE: 39

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
                20                  25                  30

Val Asp Pro Glu Gly Arg Val Tyr Thr Gln Ala Ile Ala Gln Trp His
            35                  40                  45

Asp Arg Gly Glu Gln Glu Val Leu Glu Tyr Glu Leu Glu Asp Gly Ser
50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120

<210> SEQ ID NO 40
<211> LENGTH: 185
```

<212> TYPE: PRT
<213> ORGANISM: Pyrococcus abyssi

<400> SEQUENCE: 40

Cys Phe Pro Gly Asp Thr Arg Ile Leu Val Gln Ile Asp Gly Val Pro
1               5                   10                  15

Gln Lys Ile Thr Leu Arg Glu Leu Tyr Glu Leu Phe Glu Asp Glu Arg
            20                  25                  30

Tyr Glu Asn Met Val Tyr Val Arg Lys Lys Pro Lys Arg Glu Ile Lys
        35                  40                  45

Val Tyr Ser Ile Asp Leu Glu Thr Gly Lys Val Val Leu Thr Asp Ile
50                  55                  60

Glu Asp Val Ile Lys Ala Pro Ala Thr Asp His Leu Ile Arg Phe Glu
65                  70                  75                  80

Leu Glu Asp Gly Arg Ser Phe Glu Thr Thr Val Asp His Pro Val Leu
                85                  90                  95

Val Tyr Glu Asn Gly Arg Phe Ile Glu Lys Arg Ala Phe Glu Val Lys
            100                 105                 110

Glu Gly Asp Lys Val Leu Val Ser Glu Leu Glu Leu Val Glu Gln Ser
        115                 120                 125

Ser Ser Ser Gln Asp Asn Pro Lys Asn Glu Asn Leu Gly Ser Pro Glu
130                 135                 140

His Asp Gln Leu Leu Glu Ile Lys Asn Ile Lys Tyr Val Arg Ala Asn
145                 150                 155                 160

Asp Asp Phe Val Phe Ser Leu Asn Ala Lys Lys Tyr His Asn Val Ile
                165                 170                 175

Ile Asn Glu Asn Ile Val Thr His Ala
            180                 185

<210> SEQ ID NO 41
<211> LENGTH: 132
<212> TYPE: PRT
<213> ORGANISM: Brevibacillus laterosporus

<400> SEQUENCE: 41

Cys Phe Thr Ala Gly Thr Lys Val Leu Thr Asp Glu Gly Glu Lys Pro
1               5                   10                  15

Ile Glu Glu Ile Glu Val Gly Asp Lys Val Leu Ser Lys Ser Asp Glu
            20                  25                  30

Thr Gly Val Val Ala Tyr Lys Glu Val Gly Leu Phe Gln Lys Gln
        35                  40                  45

Ser Asp Gln Ile Tyr Asn Val His Val Gly Asp Glu Val Leu Glu Ala
50                  55                  60

Thr Ala Glu His Pro Phe Trp Val Asp Gly Lys Gly Trp Thr Phe Val
65                  70                  75                  80

Lys Asp Leu Lys Val Gly Asp Leu Leu Val Ser Ser Gly Thr Thr
                85                  90                  95

Leu Ala Ile Glu Lys Ile Glu Lys Ala Pro Arg Glu Thr Thr Val Tyr
            100                 105                 110

Asn Phe Glu Val Lys Asp Phe Asn Ser Tyr Phe Val Ser Asn Leu Gly
        115                 120                 125

Ile Trp Val His
130

<210> SEQ ID NO 42
<211> LENGTH: 129

```
<212> TYPE: PRT
<213> ORGANISM: Artificial sequence
<220> FEATURE:
<223> OTHER INFORMATION: Synthesized

<400> SEQUENCE: 42

Cys Phe Lys Glu Gly Thr Lys Ile Leu Met Ser Asp Gly Ser Tyr Lys
1               5                   10                  15

Asn Ile Glu Asp Ile Val Ala Gly Asp Leu Ile Lys Thr Arg Pro Asn
            20                  25                  30

Glu Phe Asp Glu Ile Leu Val Thr Gly Glu Val Leu Lys Thr Tyr Glu
        35                  40                  45

His Val Val Ser Thr Tyr Ile Ser Val Asn Gly Val Leu Glu Val
    50                  55                  60

Thr Pro Glu His Val Ile Phe Leu Asn Asp Lys Trp Ser Leu Ala Glu
65              70                  75                  80

Asn Leu Lys Val Gly Asp Tyr Leu Ile Asn Met Asp Gly Glu Lys Val
                85                  90                  95

Trp Val Glu Ser Ala Glu Thr Ile Asn Ala Pro Thr Lys Val Tyr Asn
            100                 105                 110

Phe Glu Val Glu Lys Tyr His Thr Tyr Phe Ala Asp Asn Ile Tyr Val
        115                 120                 125

His

<210> SEQ ID NO 43
<211> LENGTH: 2388
<212> TYPE: DNA
<213> ORGANISM: Corynebacterium glutamicum

<400> SEQUENCE: 43
```

| | | | | | |
|---|---|---|---|---|---|
| gtgtccacca | cgaattctct | gacaaagctc | gttgcatcta | cagtcgccgc | tggcgtcctt | 60 |
| ggtgcgctcg | cacttgtgcc | tttcgctagt | ctttctggcg | ttgcggttgc | gcgtaccaat | 120 |
| gacacgatgc | agaccaacct | ttcagatctg | acggatggtc | gcgggccggg | cgtcacgacg | 180 |
| attactgatt | ccactgacca | gccgattgct | tatatttatg | cgcagcggcg | gtttgaggtt | 240 |
| gggggtgatc | agatttctac | gtcgatgaag | gatgcgatcg | tttcgattga | ggatcgcagg | 300 |
| ttctatgagc | atgatggtgt | ggatttgcag | gcctttggtc | gtgcaatcct | gacgaacctg | 360 |
| gctgcgggtg | gcgtggagca | gggtgcttcg | acgattaacc | agcagtatgt | gaagaacttc | 420 |
| ttgctgttgg | tggaagctga | tgatgaggcg | gagcaggctg | ctgctgtgga | aacctccatc | 480 |
| cctcgtaagc | tccgtgagat | gaagatggcg | tctgatttgg | aaaagacgtt | gtcgaaggat | 540 |
| gagattctga | ctcgttatct | caacattgtt | ccttttggta | atggtgctta | tggtgttgag | 600 |
| gctgcggcgc | ggacgtattt | cggtacgtcg | gctgccgagt | taaccattcc | acagtctgcg | 660 |
| atgctcgcgg | gcattgtgca | gtcttcgtct | tatctcaatc | catacaccaa | tcacgatgct | 720 |
| gtgtttgagc | gtcgtaatac | tgttttgggc | gctatggctg | atgctggcgc | gatttcccca | 780 |
| gacgaggctt | cggctttcca | gcaggaacct | ttgggtgtcc | tggaaacccc | gcaaggctta | 840 |
| tccaatggtt | gtatcggcgc | tggcgatcgt | ggtttcttct | gcgattacgc | tctgcaatat | 900 |
| ctttctgagc | agggaatcac | ccaagatatg | ctggcgaagg | actcctacac | catcaaattg | 960 |
| actttggatc | cagatgttca | ggatgcagcg | cacaatgcgg | tgtcctccca | cgttgatcca | 1020 |
| accaccccag | gtgtcgctga | agttgtgaac | gtcattgagc | ctggcgagaa | ctcccgcgat | 1080 |
| attttggcta | ttacttcttc | ccgcaactac | ggccttgacc | tggatgctgg | tgaaacgatg | 1140 |

```
ctgcctcagg caacgtcccg tgtgggtaat ggtgccggtt ccattttcaa gatctttacc   1200
gccgctgcag ccattcagca gggcgctggc ctagacacca tgttggatgt tccttctcga   1260
tatgaggtca agggcatggg ctccggcggt gccgcgaact gtcccgcaaa tacttactgc   1320
gtggaaaacg caggatccta cgcgcctcgc atgactctgc aggacgctct cgcgcagtcc   1380
cccaacactg cattcgttga atgatcgag caggttggcg tggacaccgt tgtggatctt   1440
tcagtaaagc tgggcctgcg aagctacacc gatgaaggtt ccttcgacgg cgaaagctca   1500
atcgcggact acatgaagga caacaacctc ggttcttaca ctcttggacc taccgctgtt   1560
aaccctcttg aattgtccaa tgttgctgca accattgcat ccggtggcat gtggtgcgaa   1620
cccaatccca tcgccagcgt ccatgaccgt gaaggcaacg aagtctacat tgaccgccct   1680
gcatgtgagc gcgccatcga tgccgaaacg gcttcagctt tggccgtcgg catgagcaag   1740
gatacggtca gcggaactgc ggcctctgca gccagcatgt acggatggtc cttgccaacc   1800
gcagcgaaga ccggtaccac cgagtccaac cagtcctcag catttatggg cttcaacagc   1860
aactttgccg cagctccata catctacaat gacggcacct ccaccacccc actgtgcagc   1920
ggccccgtcc gccagtgcag cagcggtaac ctcttcggcg gtaacgaacc agctcaaaca   1980
tggtttaaca tggcaagcaa cgtccccgca gcttcgcaag gaacactgcc atccagcagc   2040
gattcattcc gcctcggcac ttccggcgaa ctcctcaacc aggttgtcgg ccaaagcgaa   2100
gcctccgctc gacgcaccct cgaagccaaa ggctacaagg tcaccacgcg ttcagtctcc   2160
ggcgccggca gcgcgcgcgg caccgtagtc agcgcaaccc ctcagggtgc agtgcttatc   2220
gacggtggaa ccgtcatttt ggacatctcc gacggcacaa gccctgcccc cgctgccacc   2280
aacaatgatg acagcgacga tggagacacc cctgctccat caacaaacaa ccgcggaaca   2340
accattgaag acgccatcaa tgacgccatc aaccagttct ccgctag            2388
```

<210> SEQ ID NO 44
<211> LENGTH: 795
<212> TYPE: PRT
<213> ORGANISM: Corynebacterium glutamicum

<400> SEQUENCE: 44

```
Met Ser Thr Thr Asn Ser Leu Thr Lys Leu Val Ala Ser Thr Val Ala
1               5                   10                  15

Ala Gly Val Leu Gly Ala Leu Ala Leu Val Pro Phe Ala Ser Leu Ser
            20                  25                  30

Gly Val Ala Val Ala Arg Thr Asn Asp Thr Met Gln Thr Asn Leu Ser
        35                  40                  45

Asp Leu Thr Asp Gly Arg Gly Pro Gly Val Thr Thr Ile Thr Asp Ser
    50                  55                  60

Thr Asp Gln Pro Ile Ala Tyr Ile Tyr Ala Gln Arg Arg Phe Glu Val
65                  70                  75                  80

Gly Gly Asp Gln Ile Ser Thr Ser Met Lys Asp Ala Ile Val Ser Ile
                85                  90                  95

Glu Asp Arg Arg Phe Tyr Glu His Asp Gly Val Asp Leu Gln Gly Phe
            100                 105                 110

Gly Arg Ala Ile Leu Thr Asn Leu Ala Ala Gly Val Glu Gln Gly
        115                 120                 125

Ala Ser Thr Ile Asn Gln Gln Tyr Val Lys Asn Phe Leu Leu Leu Val
    130                 135                 140

Glu Ala Asp Asp Glu Ala Glu Gln Ala Ala Ala Val Glu Thr Ser Ile
145                 150                 155                 160
```

-continued

Pro Arg Lys Leu Arg Glu Met Lys Met Ala Ser Asp Leu Glu Lys Thr
            165                 170                 175

Leu Ser Lys Asp Glu Ile Leu Thr Arg Tyr Leu Asn Ile Val Pro Phe
            180                 185                 190

Gly Asn Gly Ala Tyr Gly Val Glu Ala Ala Arg Thr Tyr Phe Gly
            195                 200                 205

Thr Ser Ala Ala Glu Leu Thr Ile Pro Gln Ser Ala Met Leu Ala Gly
            210                 215                 220

Ile Val Gln Ser Ser Ser Tyr Leu Asn Pro Tyr Thr Asn His Asp Ala
225                 230                 235                 240

Val Phe Glu Arg Arg Asn Thr Val Leu Gly Ala Met Ala Asp Ala Gly
            245                 250                 255

Ala Ile Ser Pro Asp Glu Ala Ser Ala Phe Gln Gln Glu Pro Leu Gly
            260                 265                 270

Val Leu Glu Thr Pro Gln Gly Leu Ser Asn Gly Cys Ile Gly Ala Gly
            275                 280                 285

Asp Arg Gly Phe Phe Cys Asp Tyr Ala Leu Gln Tyr Leu Ser Glu Gln
            290                 295                 300

Gly Ile Thr Gln Asp Met Leu Ala Lys Asp Ser Tyr Thr Ile Lys Leu
305                 310                 315                 320

Thr Leu Asp Pro Asp Val Gln Asp Ala Ala His Asn Ala Val Ser Ser
            325                 330                 335

His Val Asp Pro Thr Thr Pro Gly Val Ala Glu Val Val Asn Val Ile
            340                 345                 350

Glu Pro Gly Glu Asn Ser Arg Asp Ile Leu Ala Ile Thr Ser Ser Arg
            355                 360                 365

Asn Tyr Gly Leu Asp Leu Asp Ala Gly Glu Thr Met Leu Pro Gln Ala
            370                 375                 380

Thr Ser Arg Val Gly Asn Gly Ala Gly Ser Ile Phe Lys Ile Phe Thr
385                 390                 395                 400

Ala Ala Ala Ala Ile Gln Gln Gly Ala Gly Leu Asp Thr Met Leu Asp
                    405                 410                 415

Val Pro Ser Arg Tyr Glu Val Lys Gly Met Gly Ser Gly Gly Ala Ala
            420                 425                 430

Asn Cys Pro Ala Asn Thr Tyr Cys Val Glu Asn Ala Gly Ser Tyr Ala
            435                 440                 445

Pro Arg Met Thr Leu Gln Asp Ala Leu Ala Gln Ser Pro Asn Thr Ala
            450                 455                 460

Phe Val Glu Met Ile Glu Gln Val Gly Val Asp Thr Val Val Asp Leu
465                 470                 475                 480

Ser Val Lys Leu Gly Leu Arg Ser Tyr Thr Asp Glu Gly Ser Phe Asp
            485                 490                 495

Gly Glu Ser Ser Ile Ala Asp Tyr Met Lys Asp Asn Leu Gly Ser
            500                 505                 510

Tyr Thr Leu Gly Pro Thr Ala Val Asn Pro Leu Glu Leu Ser Asn Val
            515                 520                 525

Ala Ala Thr Ile Ala Ser Gly Gly Met Trp Cys Glu Pro Asn Pro Ile
            530                 535                 540

Ala Ser Val His Asp Arg Glu Gly Asn Glu Val Tyr Ile Asp Arg Pro
545                 550                 555                 560

Ala Cys Glu Arg Ala Ile Asp Ala Glu Thr Ala Ser Ala Leu Ala Val
                    565                 570                 575

Gly Met Ser Lys Asp Thr Val Ser Gly Thr Ala Ala Ser Ala Ala Ser
            580                 585                 590

Met Tyr Gly Trp Ser Leu Pro Thr Ala Ala Lys Thr Gly Thr Thr Glu
            595                 600                 605

Ser Asn Gln Ser Ser Ala Phe Met Gly Phe Asn Ser Asn Phe Ala Ala
            610                 615                 620

Ala Pro Tyr Ile Tyr Asn Asp Gly Thr Ser Thr Pro Leu Cys Ser
625                 630                 635                 640

Gly Pro Val Arg Gln Cys Ser Ser Gly Asn Leu Phe Gly Gly Asn Glu
                645                 650                 655

Pro Ala Gln Thr Trp Phe Asn Met Ala Ser Asn Val Pro Ala Ala Ser
            660                 665                 670

Gln Gly Thr Leu Pro Ser Ser Ser Asp Ser Phe Arg Leu Gly Thr Ser
            675                 680                 685

Gly Glu Leu Leu Asn Gln Val Val Gly Gln Ser Glu Ala Ser Ala Arg
            690                 695                 700

Arg Thr Leu Glu Ala Lys Gly Tyr Lys Val Thr Thr Arg Ser Val Ser
705                 710                 715                 720

Gly Ala Gly Ser Ala Arg Gly Thr Val Val Ser Ala Thr Pro Gln Gly
                725                 730                 735

Ala Val Leu Ile Asp Gly Gly Thr Val Ile Leu Asp Ile Ser Asp Gly
            740                 745                 750

Thr Ser Pro Ala Pro Ala Ala Thr Asn Asn Asp Asp Ser Asp Asp Gly
            755                 760                 765

Asp Thr Pro Ala Pro Ser Thr Asn Asn Arg Gly Thr Thr Ile Glu Asp
            770                 775                 780

Ala Ile Asn Asp Ala Ile Asn Gln Phe Phe Arg
785                 790                 795

<210> SEQ ID NO 45
<211> LENGTH: 2163
<212> TYPE: DNA
<213> ORGANISM: Corynebacterium glutamicum

<400> SEQUENCE: 45
ttgacgaata gtaaaaatcc tcctgccaaa aagagcagcg gcaaaaggcg cttaaagagc      60
gactctaagg gctacgctgt aagaaacacc atcattggtg ccattgttgc tgtcattttg     120
attccagtaa tggtcttcat gggtgcttac atcatggttg atgttccaga accggaagag     180
ttggtttcac cccaggtttc gcagatttac gcatctgacg tgagactga attggcacgc      240 atcgttcctc cagaaggcaa ccgccagatg gtgacgatcg atcaggtgcc tgacactgtg     300
aaaaatgcgg tggtggctgc ggaagaccga gagttttaca caaacccggg ttttccatt     360 actggctatg cccgagcagc acttggcgta atcactggtg attcttcagc gggtggtggt     420
tccaccatta tcagcagta tgtgaagaag gctgtggttg gtgatgagcg ttcgctgatc     480
cgtaaggcta aggaattggt ctattccgcg aagatggcca atgagtggtc taaggacgag     540
gtccttgagg cttatctcaa cactgtgtac ttcggtcgaa atgcctatgg tgtgcaggct      600
gcagctcatg cattctttga taagccagta gaagagctca cggctgctga gggcgcagtg      660
ctggcggcca gtattcagct gccaagccag ttggatcctt ggacaaatcc agttgaggcg     720
gaaacgcgtt ggaactatgt catggacggc ctggtggaaa ttggcgctat ctcggcagag     780
gagcgcgcag ttgctaccta cccctgaaacc actgaccctg cgtccaacag tgcgtacacc     840
gaagccaccg gcactaatgg tttgattaag aaccaagtga tggcggagtt gtctgagctt     900

```
ggtatcactg aggatgatgt gcaaacccgt ggtttgcagg tcaccaccac cattgatcca    960
aagactcagg aaggtgccgt tgaagcggta caaaaccagt tggatcttct gtctgagaac   1020
aaccgtgcag cggtagtctc cattgatcct ctaatggtg cggttcgtgc ttattacggc    1080
ggcgaggatg cgactggttg ggactttgca acgctccgc ttcagaccgg ttctacattc    1140
aagatctttg gtctggcagc agcacttcag caaggtattc cactgtctca gccatacagc   1200
tctgcgccgg tgactgtggg tgatgctcaa atcggaaacg tcggtggcag cggttgtggt   1260
tcctgttcca tcgagcaggc gttgttgcat tcttacaaca ccagcttcat tcgtttgcag   1320
caggatctgg aaaatggttc acaggatact gcggacatgg cgcatgcttt gggtatcgcg   1380
aagtctttgc caactatccc tgagacactg actgaaaacg agagaccccc ttatgagggc   1440
atcatcttgg gtcagtatga gtcccgccca cttgatatgg cttctgcgat ggcaactatc   1500
gctaatgaag gtgtctggca ccgcccgcac ttcgtgtcca aggtggagac tgtcagcggt   1560
gaggttctct acgagttcga ggatggcgac ggcgagcgtc gtgtttctga aaaggttgca   1620
ctgaatctgc tcaaggccat ggggccaatc gctgcatact ccaacggaaa cgctctggct   1680
gatggccagg tttctgcatc caagactggt accactcagc ttggtgatac cggtgcaaac   1740
aaggatgcgt ggatgttggg tgcggcacct cagctagcta ctgcggtgtg ggtcggaact   1800
gctgataaca ctgcattgta taacacctgg ggtggcagta tgtatggttc taactcccct   1860
gccacgatct ggaagcagac catggataac gccctcgaga actcccctct cgaaacttgg   1920
gatatcgctc cagcattggg gtacggtaac ccaccagttc cggaatatgt gtggactcca   1980
agtccaaaca tcgcgactaa tgatccagaa ggagcaaccg aggaagctcc agtggaggat   2040
ccaaatgcag taatcgatac ccctgctgta gatcccactg cacctgcaga ggagaccggt   2100
aacggtcagg tagaaatcct gccggggctg actatcccgg gagatctctt agggatcggc   2160
taa                                                                 2163
```

<210> SEQ ID NO 46
<211> LENGTH: 720
<212> TYPE: PRT
<213> ORGANISM: Corynebacterium glutamicum

<400> SEQUENCE: 46

```
Met Thr Asn Ser Lys Asn Pro Pro Ala Lys Lys Ser Ser Gly Lys Arg
1               5                   10                  15

Arg Leu Lys Ser Asp Ser Lys Gly Tyr Ala Val Arg Asn Thr Ile Ile
            20                  25                  30

Gly Ala Ile Val Ala Val Ile Leu Ile Pro Val Met Val Phe Met Gly
        35                  40                  45

Ala Tyr Ile Met Val Asp Val Pro Glu Pro Glu Leu Val Ser Pro
    50                  55                  60

Gln Val Ser Gln Ile Tyr Ala Ser Asp Gly Glu Thr Glu Leu Ala Arg
65                  70                  75                  80

Ile Val Pro Pro Glu Gly Asn Arg Gln Met Val Thr Ile Asp Gln Val
                85                  90                  95

Pro Asp Thr Val Lys Asn Ala Val Val Ala Ala Glu Asp Arg Glu Phe
            100                 105                 110

Tyr Thr Asn Pro Gly Phe Ser Ile Thr Gly Tyr Ala Arg Ala Ala Leu
        115                 120                 125

Gly Val Ile Thr Gly Asp Ser Ser Ala Gly Gly Ser Thr Ile Thr
    130                 135                 140
```

```
Gln Gln Tyr Val Lys Lys Ala Val Val Gly Asp Glu Arg Ser Leu Ile
145                 150                 155                 160

Arg Lys Ala Lys Glu Leu Val Tyr Ser Ala Lys Met Ala Asn Glu Trp
            165                 170                 175

Ser Lys Asp Glu Val Leu Glu Ala Tyr Leu Asn Thr Val Tyr Phe Gly
        180                 185                 190

Arg Asn Ala Tyr Gly Val Gln Ala Ala His Ala Phe Phe Asp Lys
    195                 200                 205

Pro Val Glu Glu Leu Thr Ala Ala Glu Gly Ala Val Leu Ala Ala Ser
210                 215                 220

Ile Gln Leu Pro Ser Gln Leu Asp Pro Trp Thr Asn Pro Val Glu Ala
225                 230                 235                 240

Glu Thr Arg Trp Asn Tyr Val Met Asp Gly Leu Val Glu Ile Gly Ala
            245                 250                 255

Ile Ser Ala Glu Glu Arg Ala Val Ala Thr Tyr Pro Glu Thr Thr Asp
            260                 265                 270

Pro Ala Ser Asn Ser Ala Tyr Thr Glu Ala Thr Gly Thr Asn Gly Leu
        275                 280                 285

Ile Lys Asn Gln Val Met Ala Glu Leu Ser Leu Gly Ile Thr Glu
        290                 295                 300

Asp Asp Val Gln Thr Arg Gly Leu Gln Val Thr Thr Ile Asp Pro
305                 310                 315                 320

Lys Thr Gln Glu Gly Ala Val Glu Ala Val Gln Asn Gln Leu Asp Leu
                325                 330                 335

Leu Ser Glu Asn Asn Arg Ala Ala Val Val Ser Ile Asp Pro Ser Asn
            340                 345                 350

Gly Ala Val Arg Ala Tyr Tyr Gly Gly Glu Asp Ala Thr Gly Trp Asp
        355                 360                 365

Phe Ala Asn Ala Pro Leu Gln Thr Gly Ser Thr Phe Lys Ile Phe Gly
370                 375                 380

Leu Ala Ala Ala Leu Gln Gln Gly Ile Pro Leu Ser Gln Pro Tyr Ser
385                 390                 395                 400

Ser Ala Pro Val Thr Val Gly Asp Ala Gln Ile Gly Asn Val Gly Gly
            405                 410                 415

Ser Gly Cys Gly Ser Cys Ser Ile Glu Gln Ala Leu Leu His Ser Tyr
        420                 425                 430

Asn Thr Ser Phe Ile Arg Leu Gln Gln Asp Leu Glu Asn Gly Ser Gln
        435                 440                 445

Asp Thr Ala Asp Met Ala His Ala Leu Gly Ile Ala Lys Ser Leu Pro
        450                 455                 460

Thr Ile Pro Glu Thr Leu Thr Glu Asn Gly Glu Thr Pro Tyr Glu Gly
465                 470                 475                 480

Ile Ile Leu Gly Gln Tyr Glu Ser Arg Pro Leu Asp Met Ala Ser Ala
            485                 490                 495

Met Ala Thr Ile Ala Asn Glu Gly Val Trp His Arg Pro His Phe Val
        500                 505                 510

Ser Lys Val Glu Thr Val Ser Gly Glu Val Leu Tyr Glu Phe Glu Asp
        515                 520                 525

Gly Asp Gly Glu Arg Arg Val Ser Glu Lys Val Ala Leu Asn Leu Leu
        530                 535                 540

Lys Ala Met Gly Pro Ile Ala Ala Tyr Ser Asn Gly Asn Ala Leu Ala
545                 550                 555                 560
```

```
Asp Gly Gln Val Ser Ala Ser Lys Thr Gly Thr Thr Gln Leu Gly Asp
                565                 570                 575
Thr Gly Ala Asn Lys Asp Ala Trp Met Leu Gly Ala Ala Pro Gln Leu
            580                 585                 590
Ala Thr Ala Val Trp Val Gly Thr Ala Asp Asn Thr Ala Leu Tyr Asn
        595                 600                 605
Thr Trp Gly Gly Ser Met Tyr Gly Ser Asn Ser Pro Ala Thr Ile Trp
    610                 615                 620
Lys Gln Thr Met Asp Asn Ala Leu Glu Asn Ser Pro Leu Glu Thr Trp
625                 630                 635                 640
Asp Ile Ala Pro Ala Leu Gly Tyr Gly Asn Pro Val Pro Glu Tyr
                645                 650                 655
Val Trp Thr Pro Ser Pro Asn Ile Ala Thr Asn Asp Pro Glu Gly Ala
            660                 665                 670
Thr Glu Glu Ala Pro Val Glu Asp Pro Asn Ala Val Ile Asp Thr Pro
        675                 680                 685
Ala Val Asp Pro Thr Ala Pro Ala Glu Glu Thr Gly Asn Gly Gln Val
    690                 695                 700
Glu Ile Leu Pro Gly Leu Thr Ile Pro Gly Asp Leu Leu Gly Ile Gly
705                 710                 715                 720
```

<210> SEQ ID NO 47
<211> LENGTH: 423
<212> TYPE: DNA
<213> ORGANISM: Magnetospirillum magnetotacticum

<400> SEQUENCE: 47

```
tgcttcgtcg ccggaactcc cgtccgcatg gctgacggca gcgagaaggc aattgaaacc      60
gtggagattg gtgagcaggt ccaagggacg acggcacca tcaacgaggt tatcggattc     120
gggcgtccgc gcctcgacgg cgtcggctc tatgcgctta acagtctgga tttcttcgtg     180
acggcggacc atcctttcct gacgagcgga ggctggaagt ccttggatcc ggacgtaacc     240
aaccggatca atccggccct gaatgtcact caacttgtca tcggtgacac cctgatcacc     300
gtcggcggcc cggtcgatct gcgttccatc gagtcacaag acgcgcctgc cgaaacggtg     360
gtctacaacc tccatctaat cgggaacaat acctacgtcg ccagcggcta ttacgtgcat     420
aat                                                                   423
```

<210> SEQ ID NO 48
<211> LENGTH: 483
<212> TYPE: DNA
<213> ORGANISM: Penicillium vulpinum

<400> SEQUENCE: 48

```
tgtctcgcta agggaacccg tctgttgcga tacgatggga ccgagatcaa cgtcgaggat      60
gtgcgtgaag gtgaccaact tttgggtccc gatggagagc ctcgccgtgc attcaacata     120
gtgagtggta tcgaccgcct gtaccgcgtc aagatcggcg tgagaaaga agatctggta     180
gtcacgccga atcacattct ggtgttttac cgagagggcc cctccgatgg tcctgaaaat     240
gcggaaaggc aaacggtgga gattactgct gccgagtttg ctacccttc taccgaggaa     300
cgaagcctgt atagtgcctt cacatcccct gcagttgaga agggcgccga aggttcagct     360
gctcaaatgc atagtttcaa ggtcgaggac attagtctcg aatctgagaa acgagtgg      420
gctggtttcc gagtcgacaa agatcagctt tacctgcgcc atgactacct tgtcctgcac     480
aac                                                                   483
```

<210> SEQ ID NO 49
<211> LENGTH: 369
<212> TYPE: DNA
<213> ORGANISM: Aphanothece halophytica

<400> SEQUENCE: 49

```
tgcctcagtt ttggcaccga aattttaacc gttgagtacg gcccattgcc cattggcaaa      60
attgtgagtg aagaaattaa ttgttctgtg tacagtgttg atccagaagg gagagtttac     120
acccaggcga tcgcccaatg gcatgaccgg ggagagcagg aagtattgga atatgaattg     180
gaagatggtt cagtaatccg agctacctct gaccaccgct ttttaaccac cgattatcaa     240
ctgttggcga tcgaagaaat ttttgctagg caactggact tgttgacttt agaaaatatt     300
aagcaaactg aagaagctct tgacaaccat cgtcttccct ttccattact tgacgctggg     360
acaattaaa                                                             369
```

<210> SEQ ID NO 50
<211> LENGTH: 555
<212> TYPE: DNA
<213> ORGANISM: Pyrococcus abyssi

<400> SEQUENCE: 50

```
tgcttcccgg gtgatactag gattctcgtc caaatagatg gagttccaca gaagataact      60
ctaagggagc tgtatgagct gttcgaggat gaaaggtacg aaaatatggt ttacgttagg     120
aagaagccca gagggaaat taaggtttat tccattgacc tcgaaactgg caaagttgta     180
ttgacggata tagaggatgt cataaaggct ccggccacgg atcatttgat aaggttcgag     240
cttgaagatg gaagaagttt tgaaaccacc gtagatcatc cagttttagt ttatgaaaac     300
ggcagattta ttgagaaaag ggcctttgaa gttaaggagg gggataaagt actcgtctct     360
gagctcgagt tagttgaaca atcaagctcg tcccaggata accccaagaa cgagaactta     420
ggatcccctg agcatgacca actcttagag atcaagaata tcaaatacgt tagagctaat     480
gatgactttg tgttctctct taatgctaag aaataccata acgttataat aaatgagaat     540
attgtaacgc atcaa                                                      555
```

<210> SEQ ID NO 51
<211> LENGTH: 399
<212> TYPE: DNA
<213> ORGANISM: Brevibacillus laterosporus

<400> SEQUENCE: 51

```
tgctttacag caggtacaaa ggtattgact gacgaagggg agaaacctat tgaggaaatt      60
gaggtagggg ataaagttct ctctaaatca gatgaaactg gagtagtggc atataaagaa     120
gtcgtggggc tgtttcaaaa acagtctgat caaatctata atgtacacgt cggggatgaa     180
gttttagagc tactgcggna acatcctttt tgggtggatg caagggttg gacgtttgtt     240
aaagacctaa aagttggaga cttacttgtt tcgagtagtg ggactacatt ggcaatagaa     300
aagattgaga aagcaccaag agaaacgaca gtatacaact ttgaagttaa ggactttaat     360
tcttactttg tttcaaacct aggcatttgg gtgcataac                            399
```

<210> SEQ ID NO 52
<211> LENGTH: 387
<212> TYPE: DNA
<213> ORGANISM: Artificial sequence
<220> FEATURE:

<223> OTHER INFORMATION: Synthesized

<400> SEQUENCE: 52

| tgtttcatag | ccgggacttt | aataaagatg | gccgacggaa | gtacaaaaaa | aattgaaaac | 60 |
| attcaaaaag | gagatatcat | cttgacgcga | aaagacgaat | ggagcaataa | aaaaatagac | 120 |
| gccgaagtga | cgcaaacttt | tgaaaaaaag | gttggagaat | atctgtggat | caatgaaaat | 180 |
| cttggaatca | cggaggaaca | tatcctcttt | gtgaatgggc | aatggcagtt | agccggtgaa | 240 |
| attaaaatcg | gagatactct | catcaatgaa | tccggcaagt | cggtaacaat | cacatcgatt | 300 |
| gaacaaaaaa | gaaaatccat | aatggtctat | aacttcacgg | tggccgacca | tcacacctat | 360 |
| ttcgccaacg | gaatttatgt | ccacaac | | | | 387 |

<210> SEQ ID NO 53
<211> LENGTH: 117
<212> TYPE: DNA
<213> ORGANISM: Heloderma suspectum

<400> SEQUENCE: 53

| catggtgaag | gaacatttac | cagtgacttg | tcaaaacaga | tggaagagga | ggcagtgcgg | 60 |
| ttatttattg | agtggcttaa | gaacggagga | ccaagtagcg | gggcacctcc | gccatcg | 117 |

<210> SEQ ID NO 54
<211> LENGTH: 687
<212> TYPE: DNA
<213> ORGANISM: Artificial sequence
<220> FEATURE:
<223> OTHER INFORMATION: Synthesized

<400> SEQUENCE: 54

| gaagtgcagc | tggtcgagtc | cggcggtggc | ctggtgcagc | ctggtggctc | cctgcgtctc | 60 |
| tcctgcgcag | cttccggctt | caacatcaag | gatacctaca | tccactgggt | gcgtcaggca | 120 |
| ccaggcaagg | gcctggaatg | ggtcgctcgt | atctacccta | ccaacggtta | cacccgctac | 180 |
| gccgattccg | tgaagggccg | tttcaccatc | tccgccgaca | cctccaagaa | caccgcgtac | 240 |
| ctgcagatga | actccctccg | cgcagaggac | accgctgtct | actactgctc | ccgttggggt | 300 |
| ggcgatggct | tctacgcaat | ggactactgg | ggtcagggca | ccctggttac | cgtgtcctcc | 360 |
| gcatccacca | agggtccatc | cgtcttcccg | ctcgctccat | cctccaagtc | cacctccggt | 420 |
| ggcaccgctg | ctctgggttg | cctggttaag | gattacttcc | cagaacctgt | caccgtttcc | 480 |
| tggaactccg | gtgctctcac | ctccggtgtc | cacaccttcc | cagctgttct | ccagtcctcc | 540 |
| ggtctgtact | ccctctcctc | cgtggtcacc | gttccatcct | cctccctggg | cacccagacc | 600 |
| tacatctgca | acgtgaacca | caagccttcc | aacaccaagg | ttgataagaa | ggtggagccg | 660 |
| aagtcctgcg | acaagaccca | cacctgc | | | | 687 |

<210> SEQ ID NO 55
<211> LENGTH: 642
<212> TYPE: DNA
<213> ORGANISM: Artificial sequence
<220> FEATURE:
<223> OTHER INFORMATION: Synthesized

<400> SEQUENCE: 55

| gatatccaga | tgacccagtc | cccatcctcc | ctgtccgcat | ccgttggtga | tcgtgtgacc | 60 |
| atcacctgcc | gcgcttccca | ggatgtcaac | accgcagttg | cgtggtatca | gcagaagcct | 120 |
| ggcaaggcac | cgaagctgct | catctactcc | gcttccttcc | tctactccgg | tgttccatcc | 180 |

```
cgcttctccg gctcccgttc cggcaccgat tcacccctga ccatctcctc cctccagcct      240
gaagacttcg caacctacta ctgccagcag cactacacca ccccacctac cttcggccag      300
ggcaccaagg tcgaaatcaa gcgcaccgtt gcagctccgt ccgtgttcat cttcccgcca      360
tccgatgagc agctgaagtc cggcaccgct tccgtggtct gcctgctcaa caacttctac      420
ccacgtgagg ccaaggtgca gtggaaggtc gacaacgcgc tgcagtccgg taactcccag      480
gaatccgtga ccgagcagga ttccaaggac tccacctact ccctctcctc caccctgacc      540
ctctccaagg cagactacga aaagcacaag gtctacgctt gcgaggttac ccaccagggc      600
ctgtcctccc cagtcaccaa gtccttcaac cgcggtgaat gc                        642
```

<210> SEQ ID NO 56
<211> LENGTH: 43
<212> TYPE: PRT
<213> ORGANISM: Corynebacterium glutamicum

<400> SEQUENCE: 56

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
        35                  40

<210> SEQ ID NO 57
<211> LENGTH: 30
<212> TYPE: PRT
<213> ORGANISM: Corynebacterium glutamicum

<400> SEQUENCE: 57

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 58
<211> LENGTH: 25
<212> TYPE: PRT
<213> ORGANISM: Corynebacterium ammoniagenes

<400> SEQUENCE: 58

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 59
<211> LENGTH: 90
<212> TYPE: DNA
<213> ORGANISM: Corynebacterium glutamicum

<400> SEQUENCE: 59

```
atgtttaaca accgtatccg cactgcagct ctcgctggtg caatcgcaat ctccaccgca      60
gcttccggcg tagctatccc agcattcgct                                      90
```

<210> SEQ ID NO 60
<211> LENGTH: 8282
<212> TYPE: DNA
<213> ORGANISM: Artificial sequence
<220> FEATURE:
<223> OTHER INFORMATION: Synthesized

<400> SEQUENCE: 60

| | | | | | |
|---|---|---|---|---|---|
| gaattcgagc | tcggtacccg | gggatcccaa | attcctgtga | attagctgat | ttagtacttt | 60 |
| tcggaggtgt | ctattcttac | caaatcgtca | agttgtgggt | agagtcacct | gaatattaat | 120 |
| tgcaccgcac | gggtgatata | tgcttatttg | ctcaagtagt | tcgaggttaa | gtgtatttta | 180 |
| ggtgaacaaa | tttcagcttc | gggtagaaga | ctttcgatgc | gcttcagagc | ttctattggg | 240 |
| aaatctgaca | ccacttgatt | aaatagccta | ccccgaatt | ggggattgg | tcattttttg | 300 |
| ctgtgaaggt | agttttgatg | catatgacct | gcgtttataa | agaaatgtaa | acgtgatcag | 360 |
| atcgatataa | aagaaacagt | ttgtactcag | gtttgaagca | ttttctccga | ttcgcctggc | 420 |
| aaaaatctca | attgtcgctt | acagtttttc | tcaacgacag | gctgctaagc | tgctagttcg | 480 |
| gtggcctagt | gagtggcgtt | tacttggata | aagtaatcc | catgtcgtga | tcagccattt | 540 |
| tgggttgttt | ccatagcaat | ccaaaggttt | cgtctttcga | tacctattca | aggagcctta | 600 |
| tgaaacgcat | gaaatcgctg | gctgcggcgc | tcaccgtcgc | tggggccatg | ctggccgcac | 660 |
| ctgtggcaac | ggcagaagtg | cagctggtcg | agtccggcgg | tggcctggtg | cagcctggtg | 720 |
| gctccctgcg | tctctcctgc | gcagcttccg | gcttcaacat | caaggatacc | tacatccact | 780 |
| gggtgcgtca | ggcaccaggc | aagggcctgg | aatgggtcgc | tcgtatctac | cctaccaacg | 840 |
| gttacacccg | ctacgccgat | tccgtgaagg | gccgtttcac | catctccgcc | gacacctcca | 900 |
| agaacaccgc | gtacctgcag | atgaactccc | tccgcgcaga | ggacaccgct | gtctactact | 960 |
| gctcccgttg | gggtggcgat | ggcttctacg | caatggacta | ctggggtcag | ggcaccctgg | 1020 |
| ttaccgtgtc | ctccgcatcc | accaagggtc | catccgtctt | cccgctcgct | ccatcctcca | 1080 |
| agtccacctc | cggtggcacc | gctgctctgg | gttgcctggt | taaggattac | ttcccagaac | 1140 |
| ctgtcaccgt | ttcctggaac | tccggtgctc | tcacctccgg | tgtccacacc | ttcccagctg | 1200 |
| ttctccagtc | ctccggtctg | tactccctct | cctccgtggt | caccgttcca | tcctcctccc | 1260 |
| tgggcaccca | gacctacatc | tgcaacgtga | accacaagcc | ttccaacacc | aaggttgata | 1320 |
| agaaggtgga | gccgaagtcc | tgcgacaaga | cccacacctg | ctaaggatcc | tctagacaaa | 1380 |
| ttcctgtgaa | ttagctgatt | tagtactttt | cggaggtgtc | tattcttacc | aaatcgtcaa | 1440 |
| gttgtgggta | gagtcacctg | aatattaatt | gcaccgcacg | ggtgatatat | gcttatttgc | 1500 |
| tcaagtagtt | cgaggttaag | tgtattttag | gtgaacaaat | ttcagcttcg | ggtagaagac | 1560 |
| tttcgatgcg | cttcagagct | tctattggga | aatctgacac | cacttgatta | aatagcctac | 1620 |
| ccccgaattg | ggggattggt | cattttttgc | tgtgaaggta | gttttgatgc | atatgacctg | 1680 |
| cgtttataaa | gaaatgtaaa | cgtgatcaga | tcgatataaa | agaaacagtt | tgtactcagg | 1740 |
| tttgaagcat | tttctccgat | tcgcctggca | aaaatctcaa | ttgtcgctta | cagttttct | 1800 |
| caacgacagg | ctgctaagct | gctagttcgg | tggcctagtg | agtggcgttt | acttggataa | 1860 |
| aagtaatccc | atgtcgtgat | cagccatttt | gggttgtttc | catagcaatc | caaaggtttc | 1920 |
| gtctttcgat | acctattcaa | ggagccttcg | cctctatgaa | acgcatgaaa | tcgctggctg | 1980 |
| cggcgctcac | cgtcgctggg | gccatgctgg | ccgcacctgt | ggcaacggca | gatatccaga | 2040 |
| tgacccagtc | cccatcctcc | ctgtccgcat | ccgttggtga | tcgtgtgacc | atcacctgcc | 2100 |
| gcgcttccca | ggatgtcaac | accgcagttg | cgtggtatca | gcagaagcct | ggcaaggcac | 2160 |
| cgaagctgct | catctactcc | gcttccttcc | tctactccgg | tgttccatcc | cgcttctccg | 2220 |

```
gctcccgttc cggcaccgat ttcaccctga ccatctcctc cctccagcct gaagacttcg    2280
caacctacta ctgccagcag cactacacca ccccacctac cttcggccag ggcaccaagg    2340
tcgaaatcaa gcgcaccgtt gcagctccgt ccgtgttcat cttcccgcca tccgatgagc    2400
agctgaagtc cggcaccgct tccgtggtct gcctgctcaa caacttctac ccacgtgagg    2460
ccaaggtgca gtggaaggtc gacaacgcgc tgcagtccgg taactcccag gaatccgtga    2520
ccgagcagga ttccaaggac tccacctact ccctctcctc caccctgacc ctctccaagg    2580
cagactacga aaagcacaag gtctacgctt gcgaggttac ccaccagggc ctgtcctccc    2640
cagtcaccaa gtccttcaac cgcggtgaat gctaatctag agtcgacctg cagcgatccg    2700
gtgtatgccg cagcaggcat gagcagcccg aatatgcgcc tgctggctgc aacgaccgag    2760
gaaatgaccc gcgttttcgg cgctgaccag gcttttcac ataggctgag ccggtggcca    2820
ctgcacgtct ccgacgatcc caccgcgtac cgctggcatg cccagcacaa tcgcgtggat    2880
cgcctagctg atcccgaaaa agttttttgcc ttttgtaaaa aacttctcgg tcgccccgca    2940
aattttcgat tccagatttt ttaaaaacca agccagaaat acgacacacc gtttgcagat    3000
aatctgtctt tcggaaaaat caagtgcgat acaaaatttt tagcacccct gagctgcgca    3060
aagtcccgct tcgtgaaaat tttcgtgccg cgtgattttc cgccaaaaac tttaacgaac    3120
gttcgttata tggtgtcat gaccttcacg acgaagtacc aaaattggcc cgaatcatca    3180 gctatgatc tctctgatgt cgcgctggag tccgacgcgc tcgatgctgc cgtcgattta    3240
aaaacggtga tcggattttt ccgagctctc gatacgacgg acgcgccagc atcacgagac    3300
tgggccagtg ccgcgagcga cctagaaact ctcgtggcgg atcttgagga gctggctgac    3360
gagctgcgtg ctcggcagcg ccaggaggac gcacagtagt ggaggatcga atcagttgcg    3420
cctactgcgg tggcctgatt cctccccggc ctgacccgcg aggacggcgc gcaaaatatt    3480
gctcagatgc gtgtcgtgcc gcagccagcc gcgagcgcgc caacaaacgc cacgccgagg    3540
agctggaggc ggctaggtcg caaatggcgc tggaagtgcg tcccccgagc gaaattttgg    3600
ccatggtcgt cacagagctg gaagcggcag cgagaattat ccgcgatcgt ggcgcggtgc    3660
ccgcaggcat gacaaacatc gtaaatgccg cgtttcgtgt ggccgtggcc gcccaggacg    3720
tgtcagcgcc gccaccacct gcaccgaatc ggcagcagcg tcgcgcgtcg aaaaagcgca    3780
caggcggcaa gaagcgataa gctgcacgaa tacctgaaaa atgttgaacg ccccgtgagc    3840
ggtaactcac agggcgtcgg ctaaccccca gtccaaacct gggagaaagc gctcaaaaat    3900
gactctagcg gattcacgag acattgacac accggcctgg aaattttccg ctgatctgtt    3960
cgacacccat cccgagctcg cgctgcgatc acgtggctgg acgagcgaag accgccgcga    4020
attcctcgct cacctgggca gagaaaattt ccagggcagc aagacccgcg acttcgccag    4080
cgcttggatc aaagacccgg acacgggaga aacacagccg aagttatacc gagttggttc    4140
aaaatcgctt gcccggtgcc agtatgttgc tctgacgcac gcgcagcacg cagccgtgct    4200
tgtcctggac attgatgtgc cgagccacca ggccggcggg aaaatcgagc acgtaaaccc    4260
cgaggtctac gcgattttgg agcgctgggc acgcctggaa aaagcgccag cttggatcgg    4320
cgtgaatcca ctgagcggga atgccagct catctggctc attgatccgg tgtatgccgc    4380
agcaggcatg agcagcccga atatgcgcct gctggctgca acgaccgagg aaatgacccg    4440
cgttttcggc gctgaccagg cttttttcaca taggctgagc cggtggccac tgcacgtctc    4500
cgacgatccc accgcgtacc gctggcatgc ccagcacaat cgcgtggatc gcctagctga    4560
tcttatggag gttgctcgca tgatctcagg cacagaaaaa cctaaaaaac gctatgagca    4620
```

```
ggagttttct agcggacggg cacgtatcga agcggcaaga aaagccactg cggaagcaaa    4680
agcacttgcc acgcttgaag caagcctgcc gagcgccgct gagcgtctgg agagctgatc    4740
gacggcgtcc gtgtcctctg gactgctcca gggcgtgccg cccgtgatga gacggctttt    4800
cgccacgctt tgactgtggg ataccagtta aaagcggctg gtgagcgcct aaaagacacc    4860
aagatcatcg acgcctacga gcgtgcctac accgtcgctc aggcggtcgg agcagacggc    4920
cgtgagcctg atctgccgcc gatgcgtgac cgccagacga tggcgcgacg tgtgcgcggc    4980
tacgtcgcta aaggccagcc agtcgtccct gctcgtcaga cagagacgca gagcagccga    5040
gggcgaaaag ctctggccac tatgggaaga cgtggcggta aaaaggccgc agaacgctgg    5100
aaagacccaa acagtgagta cgcccgagca cagcgagaaa aactagctaa gtccagtcaa    5160
cgacaagcta ggaaagctaa aggaaatcgc ttgaccattg caggttggtt tatgactgtt    5220
gagggagaga ctggctcgtg gccgacaatc aatgaagcta tgtctgaatt tagcgtgtca    5280
cgtcagaccg tgaatagagc acttaagtct gcgggcattg aacttccacg aggacgccgt    5340
aaagcttccc agtaaatgtg ccatctcgta ggcagaaaac ggttccccc gtagggtct    5400 ctctcttggc ctccttcta ggtcgggctg attgctcttg aagctctcta gggggctca    5460 caccataggc agataacggt tccccaccgg ctcacctcgt aagcgcacaa ggactgctcc    5520
caaagatcgc ctagctgatc ttatggaggt tgctcgcatg atccttttg ataatctcat    5580 gaccaaaatc ccttaacgtg agttttcgtt ccactgagcg tcagaccccg tagaaaagat    5640
ccccgggctg caggcatgca agcttggcac tggccgtcgt tttacaacgt cgtgactggg    5700
aaaaccctgg cgttacccaa cttaatcgcc ttgcagcaca tccccctttc gccagctggc    5760
gtaatagcga agaggcccgc accgatcgcc cttcccaaca gttgcgcagc ctgaatggcg    5820
aatgcgattt attcaacaaa gccgccgtcc cgtcaagtca gcgtaatgct ctgccagtgt    5880
tacaaccaat taaccaattc tgattagaaa aactcatcga gcatcaaatg aaactgcaat    5940
ttattcatat caggattatc aataccatat ttttgaaaaa gccgtttctg taatgaagga    6000
gaaaactcac cgaggcagtt ccataggatg caagatcct ggtatcggtc tgcgattccg    6060
actcgtccaa catcaataca acctattaat ttcccctcgt caaaaataag gttatcaagt    6120
gagaaatcac catgagtgac gactgaatcc ggtgagaatg gcaaaagctt atgcatttct    6180
ttccagactt gttcaacagg ccagccatta cgctcgtcat caaaatcact cgcatcaacc    6240
aaaccgttat tcattcgtga ttgcgcctga gcgagacgaa atacgcgatc gctgttaaaa    6300
ggacaattac aaacaggaat cgaatgcaac cggcgcagga acactgccag cgcatcaaca    6360
atattttcac ctgaatcagg atattcttct aatacctgga atgctgtttt cccggggatc    6420
gcagtggtga gtaaccatgc atcatcagga gtacggataa aatgcttgat ggtcggaaga    6480
ggcataaatt ccgtcagcca gtttagtctg accatctcat ctgtaacatc attggcaacg    6540
ctacctttgc catgtttcag aaacaactct ggcgcatcgg gcttcccata caatcgatag    6600
attgtcgcac ctgattgccc gacattatcg cgagcccatt tatacccata taatcagca    6660 tccatgttgg aatttaatcg cggcttcgag caagacgttt cccgttgaat atggctcata    6720
acaccccttg tattactgtt tatgtaagca gacagtttta ttgttcatga tgatatattt    6780
ttatcttgtg caatgtaaca tcagagattt tgagacacaa cgtggctttg ttgaataaat    6840
cgaacttttg ctgagttgaa ggatcagatc acgcatcttc ccgacaacgc agaccgttcc    6900
gtggcaaagc aaaagttcaa aatcaccaac tggtccacct acaacaaagc tctcatcaac    6960
```

-continued

```
cgtggctccc tcactttctg gctggatgat ggggcgattc aggcctggta tgagtcagca      7020
acaccttctt cacgaggcag acctctcgac ggagttccac tgagcgtcag accccgtaga      7080
aaagatcaaa ggatcttctt gagatccttt ttttctgcgc gtaatctgct gcttgcaaac      7140
aaaaaaacca ccgctaccag cggtggtttg tttgccggat caagagctac caactctttt      7200
tccgaaggta actggcttca gcagagcgca gataccaaat actgttcttc tagtgtagcc      7260
gtagttaggc caccacttca agaactctgt agcaccgcct acatacccg ctctgctaat      7320 cctgttacca gtggctgctg ccagtggcga taagtcgtgt cttaccgggt tggactcaag      7380
acgatagtta ccggataagg cgcagcggtc gggctgaacg gggggttcgt gcacacagcc      7440
cagcttggag cgaacgacct acaccgaact gagataccta cagcgtgagc tatgagaaag      7500
cgccacgctt cccgaaggga aaaggcgga caggtatccg gtaagcggca gggtcggaac      7560
aggagagcgc acgagggagc ttccaggggg aaacgcctgg tatctttata gtcctgtcgg      7620
gtttcgccac ctctgacttg agcgtcgatt tttgtgatgc tcgtcagggg gcggagcct      7680 atggaaaaac gccagcaacg cggccttttt acggttcctg ccttttgct ggccttttgc      7740 tcacatgttc tttcctgcgt tatcccctga ttctgtggat aaccgtatta ccgcctttga      7800
gtgagctgat accgctcgcc gcagccgaac gaccgagcgc agcgagtcag tgagcgagga      7860
agcggaagaa gctcgcacat tcagcagcgt ttttcagcgc gttttcgatc aacgtttcaa      7920
tgttggtatc aacaccaggt ttaactttga acttatcggc actgacggtt actgattttg      7980
aacttttgct tgccacgga acggtctgcg ttgtcgggaa gatgcgtgat ctgatccttc      8040
aactcagcaa aagttcgcca atacgcaaac cgcctctccc cgcgcgttgg ccgattcatt      8100
aatgcagctg gcacgacagg tttcccgact ggaaagcggg cagtgagcgc aacgcaatta      8160
atgtgagtta gctcactcat taggcacccc aggctttaca ctttatgctt ccggctcgta      8220
tgttgtgtgg aattgtgagc ggataacaat ttcacacagg aaacagctat gaccatgatt      8280
ac                                                                     8282
```

<210> SEQ ID NO 61
<211> LENGTH: 30
<212> TYPE: DNA
<213> ORGANISM: Artificial Sequence
<220> FEATURE:
<223> OTHER INFORMATION: primer P27

<400> SEQUENCE: 61
gtcggatccg ccccctgag ccaaatattc                                         30

<210> SEQ ID NO 62
<211> LENGTH: 54
<212> TYPE: DNA
<213> ORGANISM: Artificial Sequence
<220> FEATURE:
<223> OTHER INFORMATION: primer P28

<400> SEQUENCE: 62
tttctagcgg aagaactggt tgatggcgtc gagctttgtc agagaattcg tggt            54

<210> SEQ ID NO 63
<211> LENGTH: 52
<212> TYPE: DNA
<213> ORGANISM: Artificial Sequence
<220> FEATURE:
<223> OTHER INFORMATION: primer P29

<400> SEQUENCE: 63

```
gtgtccacca cgaattctct gacaaagctc gacgccatca accagttctt cc          52
```

<210> SEQ ID NO 64
<211> LENGTH: 31
<212> TYPE: DNA
<213> ORGANISM: Artificial Sequence
<220> FEATURE:
<223> OTHER INFORMATION: primer P30

<400> SEQUENCE: 64

```
agtatctaga ttcgagtcgc ttttggttgg c                                 31
```

<210> SEQ ID NO 65
<211> LENGTH: 221
<212> TYPE: DNA
<213> ORGANISM: Artificial Sequence
<220> FEATURE:
<223> OTHER INFORMATION: CBD DNA-fragment

<400> SEQUENCE: 65

```
ggtaccgcgg ccgcgcttgc ggcgcccagc ctggcaccgg tctgaactcc ggcctcacca   60
ccaacccggg tgtctctgca tggcaggtta acaccgctta caccgccggc cagcttgtga  120
cctacaacgg caagacctac aaatgtttgc agcctcacac ctctttggcg ggttgggagc  180
cttctaacgt tccggcactc tggcagcttc agtaaggatc c                      221
```

<210> SEQ ID NO 66
<211> LENGTH: 52
<212> TYPE: PRT
<213> ORGANISM: Artificial Sequence
<220> FEATURE:
<223> OTHER INFORMATION: chitin binding domain

<400> SEQUENCE: 66

Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln
    50

<210> SEQ ID NO 67
<211> LENGTH: 52
<212> TYPE: DNA
<213> ORGANISM: Artificial Sequence
<220> FEATURE:
<223> OTHER INFORMATION: primer P31

<400> SEQUENCE: 67

```
gagctcggta ccgcggccgc caaattcctg tgaattagct gatttagtac tt          52
```

<210> SEQ ID NO 68
<211> LENGTH: 46
<212> TYPE: DNA
<213> ORGANISM: Artificial Sequence
<220> FEATURE:
<223> OTHER INFORMATION: primer P32

<400> SEQUENCE: 68

```
gctgggcgcc gcaagcatgc gttacaatat tctcattgat gataac                 46
```

<210> SEQ ID NO 69
<211> LENGTH: 46
<212> TYPE: DNA
<213> ORGANISM: Artificial Sequence
<220> FEATURE:
<223> OTHER INFORMATION: primer P33

<400> SEQUENCE: 69
gctgggcgcc gcaagcatga acccaaatgc caaggttaga cacgaa          46

<210> SEQ ID NO 70
<211> LENGTH: 74
<212> TYPE: DNA
<213> ORGANISM: Artificial Sequence
<220> FEATURE:
<223> OTHER INFORMATION: primer P34

<400> SEQUENCE: 70
caaccggcgc caccctcgcg gccgcagaaa acctgtactt ccagcacggc gagggaacct    60
tcacgtctga tctg                                                     74

<210> SEQ ID NO 71
<211> LENGTH: 41
<212> TYPE: DNA
<213> ORGANISM: Artificial Sequence
<220> FEATURE:
<223> OTHER INFORMATION: primer P35

<400> SEQUENCE: 71
ctctagagga tccttactga agctgccaga gtgccggaac g                41

<210> SEQ ID NO 72
<211> LENGTH: 40
<212> TYPE: DNA
<213> ORGANISM: Artificial Sequence
<220> FEATURE:
<223> OTHER INFORMATION: primer P36

<400> SEQUENCE: 72
ccaaccggcg cccacccaga aacgctggtg aaagtaaaag              40

<210> SEQ ID NO 73
<211> LENGTH: 45
<212> TYPE: DNA
<213> ORGANISM: Artificial Sequence
<220> FEATURE:
<223> OTHER INFORMATION: primer P37

<400> SEQUENCE: 73
gcacgcagcg gccgcccaat gcttaatcag tgaggcacct atctc            45

<210> SEQ ID NO 74
<211> LENGTH: 7215
<212> TYPE: DNA
<213> ORGANISM: Artificial Sequence
<220> FEATURE:
<223> OTHER INFORMATION: plasmid pEXC1-CspB(50)-exe-MAG-CBD

<400> SEQUENCE: 74
tcgacggatc gttccactga gcgtcagacc ccgtagaaaa gatcaaagga tcttcttgag    60
atcctttttt tctgcgcgta atctgctgct tgcaaacaaa aaaaccaccg ctaccagcgg   120
tggtttgttt gccggatcaa gagctaccaa ctctttttcc gaaggtaact ggcttcagca   180
gagcgcagat accaaatact gtccttctag tgtagccgta gttaggccac cacttcaaga   240

-continued

```
actctgtagc accgcctaca tacctcgctc tgctaatcct gttaccagtg gctgctgcca      300
gtggcgataa gtcgtgtctt accgggttgg actcaagacg atagttaccg gataaggcgc      360
agcggtcggg ctgaacgggg ggttcgtgca cacagcccag cttggagcga acgacctaca      420
ccgaactgag atacctacag cgtgagcatt gagaaagcgc cacgcttccc gaagggagaa      480
aggcggacag gtatccggta agcggcaggg tcggaacagg agagcgcacg agggagcttc      540
cagggggaaa cgcctggtat ctttatagtc ctgtcgggtt tcgccacctc tgacttgagc      600
gtcgattttt gtgatgctcg tcagggggc ggagcctatg gaaaaacgcc agcaacgcgg       660
ccttttacg gttcctggcc ttttgctggc cttttgctca catgttcttt cctgcgttat       720
cccctgattc tgtggataac cgtattaccg cctttgagtg agctgatacc gctcgccgca     780
gccgaacgac cgagcgcagc gagtcagtga gcgaggaagc ggaagaagct cgcacattca     840
gcagcgtttt tcagcgcgtt ttcgatcagc gtttcaatgt tggtatcaac accaggttta     900
actttgaact tatcggcact gacgttact gattttgaac ttttgctttg ccacggaacg      960
gtctgcgttg tcgggaagat gcgtgatctg atccttcaac tcagcaaaag ttcgccaata     1020
cgcaaaccgc ctctccccgc gcgttggccg attcattaat gcagctggca cgacaggttt     1080
cccgactgga aagcgggcag tgagcgcaac gcaattaatg tgagttagct cactcattag     1140
gcacccagg ctttacactt tatgcttccg gctcgtatgt tgtgtggaat tgtgagcgga      1200
taacaatttc acacaggaaa cagctatgac catgattacg ccgaattcga gctcggtacc     1260
cgctgtgttc ctgtgaatta gctgatttag tacttttcgg gggtgctcat tcttaccaaa     1320
gtgtcaagtt gtgggtaggg tcacttgaat aataattgca ccgcacaggt gatacatgct     1380
tacctcctca agtagcccga ggttaagtct attttaggtg aacaaatttc agtttcaggt     1440
agaaaacttt cgacctgctt cagagtttct attaggaaat ctgacaccac ttgattaaat     1500
aacctacccc cgaattgggg gaggggttat ttttgctgt gaacgtagtt ttggtgcaga      1560
tgacctgcgt ttataaagaa atgtaaacgt gatcagatcg atataaaaga aacagtttgt     1620
actcaggttt gaagcatttt ctccgattcg cctggcaaga atctcaattg tcgcttacag     1680
tttttctcaa cgacaggctg ctaagctgct agttcggtgg cctagtgagt ggcgtttact     1740
tgaatgaaaa gtaatcccat gtcgtgatca gccaatttgg gttgtttcca tagcaatcca     1800
aaggtttcgt ctttcgatac ctattcaagg agacccgtcgc ccatatgttt aacaaccgta     1860
tccgcactgc agctctcgct ggtgcaatcg caatctccac cgcagcttcc ggcgtagcta     1920
tcccagcatt cgctcaggag accaacccaa ccttcaacat caacaacggc ttcaacgatg     1980
ctgatggatc caccatccag ccagttgagc cagttaacca caccgaggaa accctccgcg     2040
acctgactga ctccaccggc gcttacctgg aagagttcca gtacgaaaac ctgtacttcc     2100
agcacggcga gggaaccttc acgtctgatc tgtctaagca gatggaggaa gaggcagttc     2160
gcctgttcat tgagtggctg aaaaatggcg gtccttctag cggtgcacct ccccctcct     2220
gcttcgtcgc cggaactccc gtccgcatgg ctgacggcag cgagaaggca attgaaaccg     2280
tggagattgg tgagcaggtc caagggacgg acggcaccat caacgaggtt atcggattcg     2340
ggcgtccgcg cctcgacggg cgtcggctct atgcgcttaa cagtctggat ttcttcgtga     2400
cggcggacca tccttttcctg acgagcggag gctggaagtc cctcgatccg gacgtaacca     2460
accggatcaa tccggccctg aatgtcactc aacttgtcat cggtgacacc ctgatcaccg     2520
tcggcggccc ggtcgatctg cgttccatcg agtcacaaga cgcgcctgcc gaaacggtgg     2580
```

```
tctacaacct ccatctaatc gggaacaata cctacgtcgc cagcggctat tacgtgcatg    2640
catacggtga acagcctggc accggtctga actccggcct caccaccaac ccgggtgtct    2700
ctgcatggca ggttaacacc gcttacaccg ccggccagct tgtgacctac aacggcaaga    2760
cctacaaatg tttgcagcct cacacctctt tggcggggtt ggagccttct aacgttccgg    2820
cactctggca gcttcagtaa gatcctctag agtcgacctg cagcgatccg gtgtatgccg    2880
cagcaggcat gagcagcccg aatatgcgcc tgctggctgc aacgaccgag gaaatgaccc    2940
gcgttttcgg cgctgaccag gcttttcac ataggctgag ccggtggcca ctgcacgtct    3000
ccgacgatcc caccgcgtac cgctggcatg cccagcacaa tcgcgtggat cgcctagctg    3060
atcccgaaaa agttttttgcc ttttgtaaaa aacttctcgg tcgccccgca aattttcgat    3120
tccagatttt ttaaaaacca agccagaaat acgacacacc gtttgcagat aatctgtctt    3180
tcggaaaaat caagtgcgat acaaaatttt tagcacccct gacgtgcgca aagtcccgct    3240
tcgtgaaaat tttcgtgccg cgtgattttc cgccaaaaac tttaacgaac gttcgttata    3300
atggtgtcat gaccttcacg acgaagtacc aaaattggcc cgaatcatca gctatggatc    3360
tctctgatgt cgcgctggag tccgacgcgc tcgatgctgc cgtcgattta aaaacggtga    3420
tcggattttt ccgagctctc gatacgacgg acgcgccagc atcacgagac tgggccagtg    3480
ccgcgagcga cctagaaact ctcgtggcgg atcttgagga gctggctgac gagctgcgtg    3540
ctcggcagcg ccaggaggac gcacagtagt ggaggatcga atcagttgcg cctactgcgg    3600
tggcctgatt cctccccggc ctgacccgcg aggacggcgc gcaaaatatt gctcagatgc    3660
gtgtcgtgcc gcagccagcc gcgagcgcgc caacaaacgc cacgccgagg agctggaggc    3720
ggctaggtcg caaatggcgc tggaagtgcg tcccccgagc gaaattttgg ccatggtcgt    3780
cacagagctg gaagcggcag cgagaattat ccgcgatcgt ggcgcggtgc ccgcaggcat    3840
gacaaacatc gtaaatgccg cgtttcgtgt ggccgtggcc gcccaggacg tgtcagcgcc    3900
gccaccacct gcaccgaatc ggcagcagcg tcgcgcgtcg aaaaagcgca caggcggcaa    3960
gaagcgataa gctgcacgaa tacctgaaaa atgttgaacg ccccgtgagc ggtaactcac    4020
agggcgtcgg ctaaccccca gtccaaacct gggagaaagc gctcaaaaat gactctagcg    4080
gattcacgag acattgacac accggcctgg aaatttttccg ctgatctgtt cgacacccat    4140
cccgagctcg cgctgcgatc acgtggctgg acgagcgaag accgccgcga attcctcgct    4200
cacctgggca gagaaaattt ccagggcagc aagacccgcg acttcgccag cgcttggatc    4260
aaagacccgg acacgggaga acacagccg aagttatacc gagttggttc aaaatcgctt    4320
gcccggtgcc agtattgttg ccttgacgca cgcgcagcac gcagccgtgc ttgtcctgga    4380
cattgatgtg ccgagccacc aggccggcgg gaaaatcgag cacgtaaacc ccgaggtcta    4440
cgcgattttg gagcgctggg cacgcctgga aaaagcgcca gcttggatcg gcgtgaatcc    4500
actgagcggg aaatgccagc tcatctggct cattgatccg gtgtatgccg cagcaggcat    4560
gagcagcccg aatatgcgcc tgctggctgc aacgaccgag gaaatgaccc gcgttttcgg    4620
cgctgaccag gcttttcac ataggctgag ccggtggcca ctgcacgtct ccgacgatcc    4680
caccgcgtac cgctggcatg cccagcacaa tcgcgtggat cgcctagctg atcttatgga    4740
ggttgctcgc atgatctcag gcacagaaaa acctaaaaaa cgctatgagc aggagttttc    4800
tagcggacgg gcacgtatcg aagcggcaag aaaagccact gcggaagcaa aagcacttgc    4860
cacgcttgaa gcaagcctgc cgagcgccgc tgaagcgtct ggagagctga tcgacggcgt    4920
ccgtgtcctc tggactgctc cagggcgtgc cgcccgtgat gagacggctt ttcgccacgc    4980
```

```
tttgactgtg ggataccagt taaaagcggc tggtgagcgc ctaaaagaca ccaagatcat    5040
cgacgcctac gagcgtgcct acaccgtcgc tcaggcggtc ggagcagacg gccgtgagcc    5100
tgatctgccg ccgatgcgtg accgccagac gatggcgcga cgtgtgcgcg gctacgtcgc    5160
taaaggccag ccagtcgtcc ctgctcgtca gacagagacg cagagcagcc gagggcgaaa    5220
agctctggcc actatgggaa gacgtggcgg taaaaaggcc gcagaacgct ggaaagaccc    5280
aaacagtgag tacgcccgag cacagcgaga aaaactagct aagtccagtc aacgacaagc    5340
taggaaagct aaaccaaatc gcttgaccat tgcaggttgg tttatgactg ttgagggaga    5400
gactggctcg tggccgacaa tcaatgaagc tatgtctgaa tttagcgtgt cacgtcagac    5460
cgtgaataga gcacttaagt ctgcgggcat tgaacttcca cgaggacgcc gtaaagcttc    5520
ccagtaaatg tgccatctcg taggcagaaa acggttcccc ccgtaggtct ctctcttggc    5580
ctcctttcta ggtcgggctg attgctcttg aagctctcta gggggctca caccataggc     5640 agataacggt tccccaccgg ctcacctcgt aacgcgacaa ggactgctcc caagatcgc     5700 ctagctgatc ttatggaggt tgctcgcatg atcctttttg ataatctcat gaccaaaatc    5760
ccttaacgtg agttttcgtt ccactgagcg tcagaccccg tagaaaagat ccccgggctg    5820
caggcatgca agcttggcac tggccgtcgt tttacaacgt cgtgactggg aaaaccctgg    5880
cgttacccaa cttaatcgcc ttgcagcaca tcccccttc gccagctggc gtaatagcga    5940
agaggcccgc accgatcgcc cttcccaaca gttgcgcagc ctgaatggcg aatgcgattt    6000
attcaacaaa gccgccgtcc cgtcaagtca gcgtaatgct ctgccagtgt tacaaccaat    6060
taaccaattc tgattagaaa aactcatcga gcatcaaatg aaactgcaat ttattcatat    6120
caggattatc aataccatat ttttgaaaaa gccgtttctg taatgaagga gaaaactcac    6180
cgaggcagtt ccataggatg gcaagatcct ggtatcggtc tgcgattccg actcgtccaa    6240
catcaataca accattaat ttcccctcgt caaaaataag gttatcaagt gagaaatcac    6300
catgagtgac gactgaatcc ggtgagaatg gcaaaagctt atgcatttct ttccagactt    6360
gttcaacagg ccagccatta cgctcgtcat caaaatcact cgcatcaacc aaaccgttat    6420
tcattcgtga ttgcgcctga gcgagacgaa atacgcgatc gctgttaaaa ggacaattac    6480
aaacaggaat cgaatgcaac cggcgcagga acactgccag cgcatcaaca atattttcac    6540
ctgaatcagg atattcttct aatacctgga atgctgtttt cccggggatc gcagtggtga    6600
gtaaccatgc atcatcagga gtacggataa aatgcttgat ggtcggaaga ggcataaatt    6660
ccgtcagcca gtttagtctg accatctcat ctgtaacatc attggcaacg ctacctttgc    6720
catgtttcag aaacaactct ggcgcatcgg gcttcccata caatcgatag attgtcgcac    6780
ctgattgccc gacattatcg cgagcccatt tatacccata taaatcagca tccatgttgg    6840
aatttaatcg cggcttcgag caagacgttt cccgttgaat atggctcata cacccccttg    6900
tattactgtt tatgtaagca gacagtttta ttgttcatga tgatatattt ttatcttgtg    6960
caatgtaaca tcagagattt tgagacacaa cgtggctttg ttgaataaat cgaacttttg    7020
ctgagttgaa ggatcagatc acgcatcttc ccgacaacgc agaccgttcc gtggcaaagc    7080
aaaagttcaa aatcaccaac tggtccacct acaacaaagc tctcatcaac cgtggctccc    7140
tcactttctg gctggatgat ggggcgattc aggcctggta tgagtcagca acaccttctt    7200
cacgaggcag acctc                                                     7215
```

<210> SEQ ID NO 75

-continued

```
<211> LENGTH: 23
<212> TYPE: PRT
<213> ORGANISM: Escherichia coli
<220> FEATURE:
<223> OTHER INFORMATION: leader peptide of beta-lactamase

<400> SEQUENCE: 75

Met Ser Ile Gln His Phe Arg Val Ala Leu Ile Pro Phe Phe Ala Ala
1               5                   10                  15

Phe Cys Leu Pro Val Phe Ala
            20
```